(12) United States Patent
Pomper et al.

(10) Patent No.: US 11,021,450 B2
(45) Date of Patent: Jun. 1, 2021

(54) PSMA TARGETED FLUORESCENT AGENTS FOR IMAGE GUIDED SURGERY

(71) Applicant: The Johns Hopkins University, Baltimore, MD (US)

(72) Inventors: Martin G. Pomper, Baltimore, MD (US); Ronnie C. Mease, Fairfax, VA (US); Ying Chen, Timonium, MD (US); Sangeeta Ray, Ellicott City, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 16/820,052

(22) Filed: Mar. 16, 2020

(65) Prior Publication Data

US 2020/0216402 A1    Jul. 9, 2020

Related U.S. Application Data

(60) Continuation of application No. 16/704,137, filed on Dec. 5, 2019, which is a continuation of application No. 15/618,788, filed on Jun. 9, 2017, now abandoned, which is a continuation-in-part of application No. 14/243,535, filed on Apr. 2, 2014, now Pat. No. 9,776,977, which is a division of application No. 13/257,499, filed as application No. PCT/US2010/028020 on Mar. 19, 2010, now Pat. No. 9,056,841.

(60) Provisional application No. 61/248,067, filed on Oct. 2, 2009, provisional application No. 61/161,484, filed on Mar. 19, 2009, provisional application No. 61/161,485, filed on Mar. 19, 2009, provisional application No. 61/248,934, filed on Oct. 6, 2009, provisional application No. 62/324,097, filed on Apr. 18, 2016.

(51) Int. Cl.

| | |
|---|---|
| A61K 51/00 | (2006.01) |
| A61M 36/14 | (2006.01) |
| C07D 257/02 | (2006.01) |
| C07D 311/20 | (2006.01) |
| A61K 51/04 | (2006.01) |
| C07D 311/82 | (2006.01) |
| C07D 213/04 | (2006.01) |
| C07D 209/14 | (2006.01) |
| C07D 249/04 | (2006.01) |
| C07F 13/00 | (2006.01) |
| C07D 209/12 | (2006.01) |
| C07D 255/02 | (2006.01) |
| A61K 49/00 | (2006.01) |
| G01N 33/50 | (2006.01) |
| C07D 311/14 | (2006.01) |
| C07F 5/02 | (2006.01) |
| C07D 209/24 | (2006.01) |

(52) U.S. Cl.
CPC ........ *C07D 257/02* (2013.01); *A61K 49/0032* (2013.01); *A61K 49/0052* (2013.01); *A61K 51/044* (2013.01); *A61K 51/0421* (2013.01); *A61K 51/0446* (2013.01); *A61K 51/0453* (2013.01); *A61K 51/0472* (2013.01); *C07D 209/12* (2013.01); *C07D 209/14* (2013.01); *C07D 209/24* (2013.01); *C07D 213/04* (2013.01); *C07D 249/04* (2013.01); *C07D 255/02* (2013.01); *C07D 311/14* (2013.01); *C07D 311/20* (2013.01); *C07D 311/82* (2013.01); *C07F 5/027* (2013.01); *C07F 13/005* (2013.01); *G01N 33/5091* (2013.01); *G01N 2800/342* (2013.01)

(58) Field of Classification Search
None
See application file for complete search history.

(56) References Cited

U.S. PATENT DOCUMENTS

| | | | |
|---|---|---|---|
| 6,159,657 | A | 12/2000 | Fleming et al. |
| 6,392,036 | B1 | 5/2002 | Karlsson et al. |
| 6,887,854 | B2 | 5/2005 | Achilefu et al. |
| 8,169,469 | B2 | 5/2012 | Miyake et al. |
| 9,044,468 | B2 | 6/2015 | Pomper et al. |
| 9,056,841 | B2 | 6/2015 | Pomper et al. |
| 9,776,977 | B2 | 10/2017 | Pomper et al. |
| 2004/0054190 | A1 | 3/2004 | Pomper et al. |
| 2010/0183509 | A1 | 7/2010 | Babich et al. |
| 2010/0324008 | A1 | 12/2010 | Low et al. |
| 2011/0200677 | A1 | 8/2011 | Chandran et al. |
| 2012/0009121 | A1 | 1/2012 | Pomper et al. |
| 2018/0283384 | A1 | 1/2018 | Pomper et al. |

FOREIGN PATENT DOCUMENTS

| | | |
|---|---|---|
| WO | WO 02/41925 | 5/2002 |
| WO | WO 03/060523 | 7/2003 |
| WO | WO 2009/002529 | 12/2008 |

(Continued)

OTHER PUBLICATIONS

Al-Muhammed, "In-vivo studies on desamethasone sodium phosphate liposomes," J. Microencapsul., 1996, 13:293-306.

(Continued)

*Primary Examiner* — Michael G. Hartley
*Assistant Examiner* — Melissa J Perreira
(74) *Attorney, Agent, or Firm* — Casimir Jones, S.C.; Jeffrey W. Childers

(57) ABSTRACT

Compositions and methods for visualizing tissue under illumination with near-infrared radiation, including compounds comprising near-infrared, closed chain, sulfo-cyanine dyes and prostate specific membrane antigen ligands are disclosed.

21 Claims, 17 Drawing Sheets
(1 of 17 Drawing Sheet(s) Filed in Color)

(56) References Cited

FOREIGN PATENT DOCUMENTS

| | | |
|---|---|---|
| WO | WO 2009/026177 | 2/2009 |
| WO | WO 2010/108125 | 9/2010 |

OTHER PUBLICATIONS

Antunes et al., "Influence of different spacers on the biological profile of a DOTA-somatostatin analogue," Bioconjug Chem., vol. 18, pp. 84-92, 2007.
Arndt-Jovin et al., "Tumor-targeted quantum dots can help surgeons find tumor boundaries," IEEE Trans Nanobioscience, vol. 8, No. 1, pp. 65-71, Mar. 2009.
Baccala et al., "Expression of prostate-specific membrane antigen in tumor-associated neovasculature of renal neoplasms," Urology, vol. 70, pp. 385-390, 2007.
Banerjee et al., "Synthesis and evaluation of technetium-99m- and rhenium-labeled inhibitors of the prostate-specific membrane antigen (PSMA)," J. Med. Chem., vol. 51, pp. 4504-4517, 2008.
Barinka et al., "Interactions between human glutamate carboxypeptidase II and urea-based inhibitors: Structural Characterizations," J. Med. Chem, vol. 51, pp. 7737-7743, 2008.
Byun et al., "Recent Development of Therapeutic and Diagnostic Agents Targeting Glutamate Carboxypeptidase II (GCP II)" In: Drug Design of Zinc-Enzyme Inhibitors, Supuran, C. ed. Hoboken, N.J.: John Wley & Sons, pp. 881-910, 2009.
Chandran et al., "Characterization of a targeted nanoparticle functionalized with a urea-based inhibitor of prostate-specific membrane antigen (PSMA)," Cancer Biol. Ther., vol. 7, pp. 974-982, 2008.
Chang et al., "Five different anti-prostate-specific membrane antigen (PSMA) antibodies confirm PSMA expression in tumor-associated neovasculature," Cancer Research, vol. 59, pp. 3192-3198, 1999.
Chang et al., "Metastatic renal cell carcinoma neovasculature expresses prostate-specific membrane antigen," Urology, vol. 57, pp. 801-805, 2001.
Chang et al., "Prostate-specific membrane antigen is produced in tumor-associated neovasculature," Clin. Cancer Res., vol. 5, pp. 2674-2681, 1999.
Chang et al., "Prostate-specific membrane antigen: Much more than a prostate cancer marker," Mol. Urol., vol. 3 No. 3, pp. 313-320, 1999.
Chen et al., "Synthesis and biological evaluation of low molecular weight fluorescent imaging agents for the prostate-specific membrane antigen," Bioconjug Chem, 2012, 23: 2377-85.
Chen et al., "A low molecular weight PSMA-based fluorescent imaging agent for cancer," Biochem Biophys Res. Commun., 2009, 390: 624-629.
Chen et al., "Radiohalogenated prostate-specific membrane antigen (PSMA)-based ureas as imaging agents for prostate cancer," J. Med. Chem. vol. 51, pp. 7933-7943, 2008.
Cheng et al., "Relationship between the inhibition constant (K1) and the concentration of inhibitor which causes 50 percent inhibition (150) of an enzymatic reaction," Biochem. Pharmcol., vol. 22, pp. 3099-3108, 1973.
Chonn, "Recent advances in liposomal drug-delivery systems," Curr. Opin. Biotechnol., 1995, 6:698-708.
Clarke, "Stabilities of trivalent metal ion complexes of the tetraacetate derivatives of 12-, 13-, and 14-membered tetraazamacrocycles," Inorg. Chim. Acta, vol. 190, pp. 37-46, 1992.
De Leon-Rodriguez et al., "Solid-Phase Synthesis of DOTA-Peptides," Chem Eur J 2004, 10, 1149-115.
Extended European Search Report for Application No. 17169052.2 dated Jun. 20, 2017 (9 pages).
Extended European Search Report issued in counterpart European Application No. 10754194.8 dated Aug. 14, 2012.
Eyles, "Oral Delivery and Fate of Poly(lactic acid) Microsphere-encapsulated Interferon in Rats," J. Pharm. Pharmacol., 1997, 49:669-674.

Fani et al., "$^{68}$Ga-PET: a powerful generator-based alternative to cyclotron-based PET radiopharmaceuticals," Contrast Media Mol. Imaging, vol. 3, pp. 53-63, 2008.
Foss et al., "Radiolabeled small-molecule ligands for prostate-specific membrane antigen: in vivo imaging in experimental models of prostate cancer," Clin. Cancer Res., vol. 11, No. 11, pp. 4022-4028, 2005.
Galsky et al., "Phase I trial of the prostate-specific membrane antigen-directed immunoconjugate MLN2704 in patients with progressive metastatic castration-resistant prostate cancer," Journal of Clinical Oncology, vol. 26, pp. 2147-2154, 2008.
Ghose et al., "Prediction of hydrophobic (lipophilic) properties of small organic molecules using fragmental methods: an analysis of ALOGP and CLOGP methods," J. Phys. Chem. A, vol. 102, pp. 3762-3772, 1998.
Ghosh et al., "Tumor target prostate specific membrane antigen (PSMA) and its regulation in prostate cancer," J. Cell. Biochem., vol. 91, pp. 528-539, 2004.
Gong et al., "Prostate-specific membrane antigen (PSMA)-specific monoclonal antibodies in the treatment of prostate and other cancers," Cancer Metastasis Rev., vol. 18, pp. 483-490, 1999.
Gotoh et al., "A novel image-guided surgery of hepatocellular carcinoma by indocyanine green fluorescence imaging navigation," J. Surg. Oncol., pp. 75-79, 2009.
Guilarte et al., "Dysregulation of glutamate carboxypeptidase II in psychiatric disease," Schizophr Res., vol. 99, pp. 324-332, 2008.
Guilarte et al., "Glutamate Carboxypeptidase II Levels in Rodent Brain using [125I]DCIT Quantitative Autoradiography," Neurosci Lett., vol. 387, pp. 141-144, 2005.
Hamachi et al., "Single- or Dual-Mode Switching of Semisynthetic Ribonuclease S' with an Iminodiacetic Acid Moiety in Response to the Copper(II) Concentration," Chem. Eur., vol. 5, pp. 1503-1511,1999.
Haseman et al., "Capromab Pendetide imaging of prostate cancer," Cancer Biother. Radiopharm., vol. 15, pp. 131-140, 2001.
Henderson, et al., "An electrospray mass spectrometric investigation of gallium trihalide and indium trihalide solutions," Inorg. Chim. Acta., vol. 277, pp. 26-30, 1998.
Hillier et al., "Preclinical evaluation of novel glutamate-urea-lysine analogues that target prostate-specific membrane antigen as molecular imaging pharmaceuticals for prostate cancer," Cancer Res., vol. 69, pp. 6932-6940, 2009.
Humblet et al., "High-affinity near-infrared fluorescent small-molecule contrast agents for in vivo imaging of prostate-specific membrane antigen," Mol. Imaging, vol. 4, pp. 448-462, 2005.
Humblet et al., "Multivalent scaffolds for affinity maturation of small molecule cell surface binders and their application to prostate tumor targeting," J. Med. Chem., vol. 52, pp. 544-550, 2009.
International Preliminary Report on Patentability issued in counterpart International Application No. PCT/US2010/028020 dated Sep. 20, 2011.
Jackson et al., "Design, synthesis, and biological activity of a potent inhibitor of the neuropeptidase N-acetylated alpha-linked acidic dipeptidase," J. Med. Chem., vol. 39, pp. 619-622, 1996.
Kaiser et al., "Color test for detection of free terminal amino groups in the solid-phase synthesis of peptides," Anal. Biochem., vol. 34, pp. 595-598, 1970.
Kaushal et al., "Fluorophore-conjugated anti-CEA antibody for the intraoperative imaging of pancreatic and colorectal cancer," J. Gastrointest. Surg., vol. 12, pp. 1938-1950, 2008.
Khan et al., "Clinical indications for Gallium-68 positron emission tomography imaging," Eur. J. Surg. Oncol., vol. 35, pp. 561-567, 2009.
Kilbourn et al., "From Cyclotron to Patient via HPLC," Anal Chromat Tech Radiopharm Chem 1986, 251-260.
Kinoshita et al., "Expression of prostate-specific membrane antigen in normal and malignant human tissues," World J. Surg., vol. 30, pp. 628-636, 2006.
Kozikowski et al., "Synthesis of urea-based inhibitors as active site probes of glutamate carboxypeptidase II: efficacy as analgesic agents," J. Med. Chem., vol. 47, pp. 1729-1738, 2004.

(56) References Cited

OTHER PUBLICATIONS

Kularante et al., "Prostate-specific membrane antigen (PSMA)-targeted imaging and therapy of prostate cancer using a PSMA inhibitor as a homing ligand," Molecular Pharmaceutics, vol. 6, pp. 780-789, 2009.
Kularatne et al., "Design, synthesis, and preclinical evaluation of prostate-specific membrane antigen targeted (99m)Tc-radioimaging agents," Mol. Pharm., vol. 6, pp. 790-800, 2009.
Lange, "Prostascint scan for staging prostate cancer," Urology, vol. 57, pp. 402-406, 2001.
Lapi et al., "Assessment of an .sup.18F-labeled phosphoramidate peptidomimetic as a new prostate-specific membrane antigen-targeted imaging agent for prostate cancer," J. Nucl. Med., vol. 50, pp. 2042-2048, 2009.
Lee et al., "A Steroid-Conjugated Contrast Agent for Magnetic Resonance Imaging of Cell Signaling," JACS 2005, 127, 13164-13166.
Liu et al., "Cell-Surface labeling and internalization by a fluorescent inhibitor of prostate-specific membrane antigen," Prostate, vol. 68, pp. 955-964, 2008.
Maresca et al., "A Series of Halogenated Heterodimeric Inhibitors of Prostate Specific Membrane Antigen (PSMA) as Radiolabeled Probes for Targeting Prostate Cancer," J. Med. Chem., 2009, vol. 52, pp. 347-357.
Matsui et al., "Real-time intraoperative near-infrared fluorescence angiography for perforator identification and flap design," Plast. Reconstr. Surg., vol. 123, pp. 125e-127e, 2009.
Mease et al., "Synthesis and in vivo evaluation of N-[N-[(S)-1,3-Dicarboxypropyl]Carbamoyl]-4-[18F]Fluorobenzyl-L-Cysteine, [18F]DCFBC: A New Imaging Probe for Prostate Cancer," Clin. Cancer Res., vol. 14, pp. 3036-3043, 2008.
Milowsky et al., "Vascular targeted therapy with anti-prostate-specific membrane antigen monoclonal antibody J591 in advanced solid tumors," J. Clin. Oncol., vol. 25, pp. 540-547, Feb. 2007.
Mindt et al., "'Click to Chelate': Synthesis and Installation of Metal Chelates into Biomolecules in a Single Step," JACS, 2006, 128, 15096-15097.
Minto, "Pharmacokinetics and pharmacodynamics of nandrolone esters in oil vehicle: effects of ester, injection site and injection volume," J. Pharmacol. Exp. Ther., 1997, 281:93-102.
Misra et al., "Production of multimeric prostate-specific membrane antigen small-molecule radiotracers using a solid-phase 99mTc preloading strategy," J. Nucl. Med., vol. 48, pp. 1379-1389, 2007.
Murphy et al., "Measurement of serum prostate-specific membrane antigen, a new prognostic marker for prostate cancer," Urology, vol. 51, pp. 89-97, 1998.
Okuda et al., "Metastatic brain tumor surgery using fluorescein sodium: technical note," Minim. Invasive Neurosurg., vol. 50, pp. 382-384, 2007.
Ostro, "Use of liposomes as injectable drug delivery systems," Am. J. Hosp. Pharm., 1989, 46:1576-1587.
Pomper et al., ".sup.11C-MCG: Synthesis, uptake selectivity and primate PET of a probe for glutamate carboxypeptidase II (NAALADase.)," Mol. Imaging, vol. 1, pp. 96-101, 2002.
Ra et al., In Vivo Imaging of Human and Mouse Skin With a Handheld Dual-Axis Confocal Fluorescence Microscope. J Invest Dermatol . May 2011;131(5):1061-6.
Rao, "Recent developments of collagen-based materials for medical applications and drug delivery systems," J. Biomater Sci. Polym. Ed., 1995, 7:623-645.
Reubi et al., "Peptide-based probes for cancer imaging," J. Nucl. Med., vol. 49, pp. 1735-1738, 2008.
Rohatagi et al., "Pharmacokinetic and Pharmacodynamic Evaluation of Triamcinolone Acetonide After Intravenous, Oral, and Inhaled Administration," J. Clin. Pharmacol., 1995, 35:1187-1193.
Rosenthal et al., "Utility of Capromab Pendetide (ProstaScint) Imaging in the Management of Prostate Cancer," Tech. Urol., vol. 7, pp. 27-37, 2001.
Rowe et al., "Imaging of metastatic clear cell renal cell carcinoma with PSMA-targeted 18F-DCFPyL PET/CT," Ann. Nucl. Med., 2015, 29(10) 877-882.
Sanchez-Crespo et al., "Positron flight in human tissues and its influence on PET image spatial resolution," Eur. J. Nucl. Med. Mol. Imaging, vol. 31, pp. 44-51, 2004.
Sevick-Muraca et al., "Fluorescence and absorption contrast mechanisms for biomedical optical imaging using frequency-domain techniques," Photochem. Photobiol., vol. 66, pp. 55-64, 1997.
Sheth et al., "Improved detection of ovarian cancer metastases by intraoperative quantitative fluorescence protease imaging in a preclinical model," Gynecol. Oncol., vol. 112, pp. 616-622, 2009.
Silver et al., "Prostate-specific membrane antigen expression in normal and malignant human tissues," Clinical Cancer Research, vol. 3, pp. 81-85, 1997.
Slusher et al., "Immunocytochemical localization of the N-acetyl-aspartyl-glutamate (NAAG) hydrolyzing enzyme N-acetylated alpha-linked acidic dipeptidase (NAALADase)," J.Comp. Neuro., vol. 315, pp. 217-229, 1992.
Stummer et al., "Fluorescence-guided surgery with 5-aminolevulinic acid for resection of malignant glioma: a randomised controlled multicentre phase III trial," Lancet Oncol., vol. 7, pp. 392-401, 2006.
Su et al., "Microfluidic Cell Culture and Its Application in High Throughput Drug Screening: Cardiotoxicity Assay for hERG Channels," J. Biomol Screen, 2011, 16, 101-111.
Tasch et al., "A unique folate hydrolase, prostate-specific membrane antigen (PSMA): a target for immunotherapy?," Crit. Rev. Immunol., vol. 21, pp. 249-261, 2001.
Tjwa, "Budesonide inhaled via Turbuhaler: a more effective treatment for asthma than beclomethasone dipropionate via Rotahaler," Ann. Allery Asthma Immunol., 1995, 75:107-111.
Toda, "Intraoperative navigation and fluorescence imagings in malignant glioma surgery," Keio J. Med., vol. 57, pp. 155-161, 2008.
Wang et al., "Methods for MAG3 conjugation and .sup.99mTc radiolabeling of biomolecules," Nature Protocols, vol. 1, pp. 1477-1480, 2006.
Zhang et al., "Novel synthesis of [1-$^{11}$C]γ-vinyl-γ-aminobutyric acid ([1-$^{11}$C]GVG) for pharmacokinetic studies of addiction treatment," J label Compd Radiopharm 2002, 45, 199-211.
Zhernosekov et al., "Processing of generator-produced .sup.68Ga for medical application," J. Nucl. Med., vol. 48, pp. 1741-1748, 2007.
Zhou et al., "NAAG Peptidase inhibitors and their potential for diagnosis and therapy," Nat. Rev. Drug Discov., vol. 4, pp. 1015-1026, 2005.

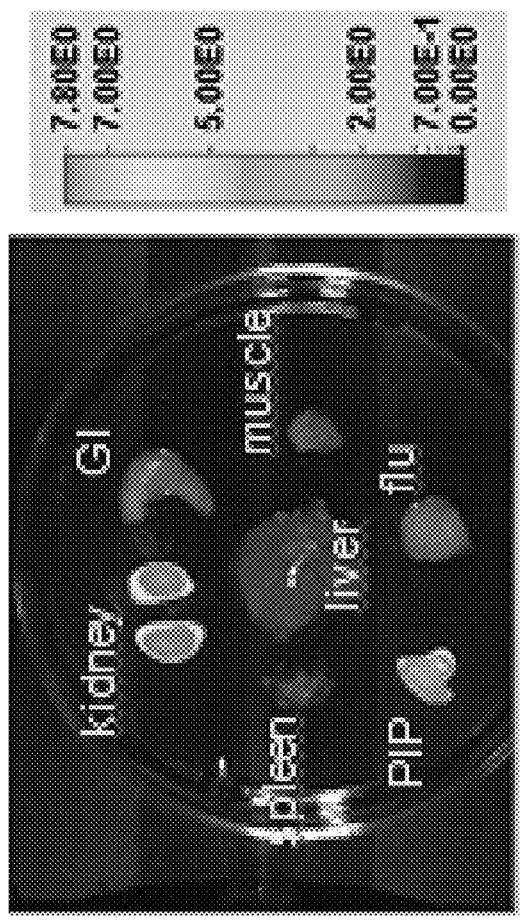
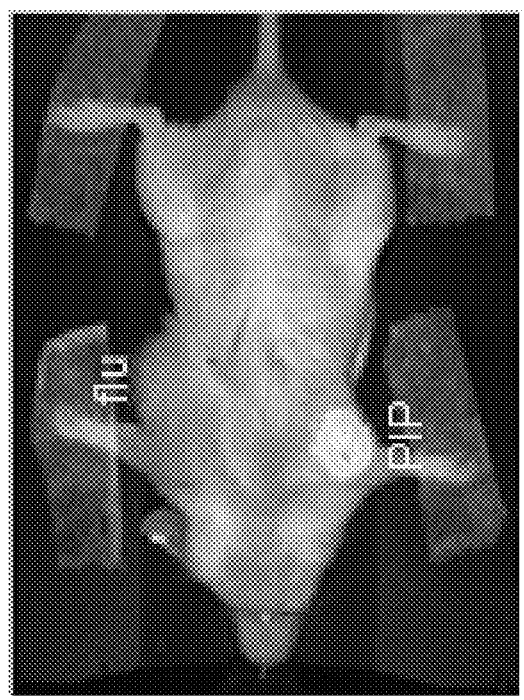
Fig. 1

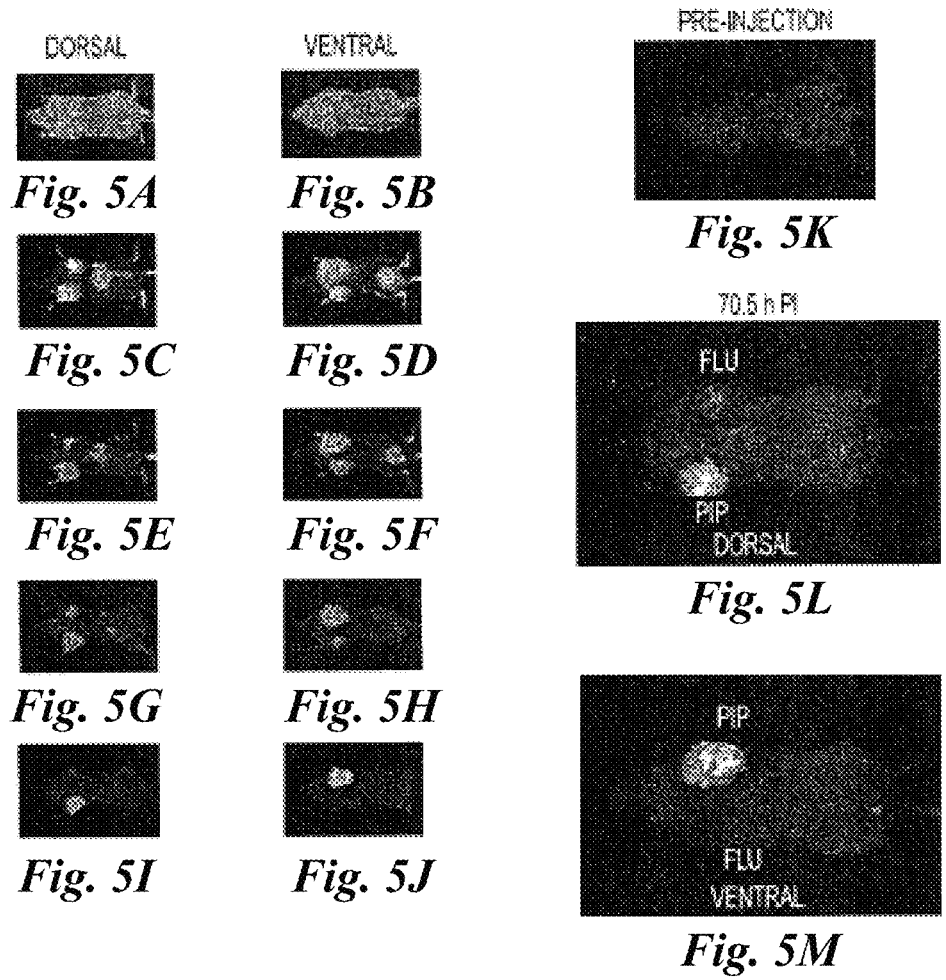
Fig. 5A Fig. 5B
Fig. 5C Fig. 5D
Fig. 5E Fig. 5F
Fig. 5G Fig. 5H
Fig. 5I Fig. 5J
Fig. 5K
Fig. 5L
Fig. 5M
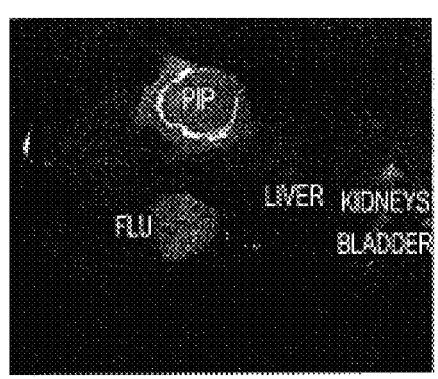
Fig. 5N
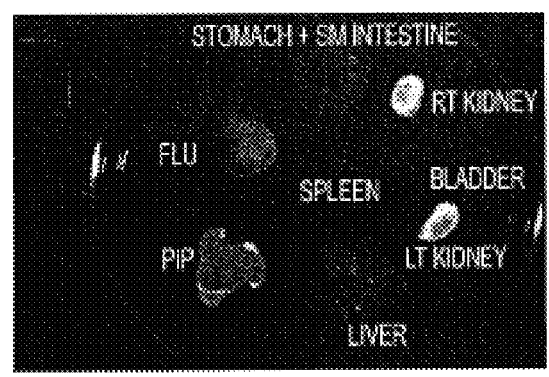
Fig. 5O

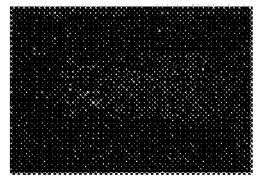 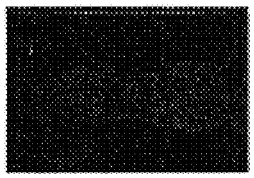 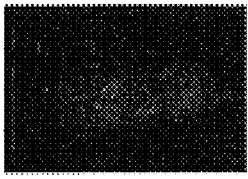 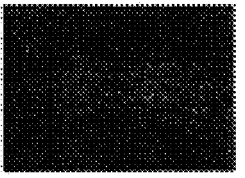
*Fig. 6A*  *Fig. 6B*  *Fig. 6K*  *Fig. 6L*
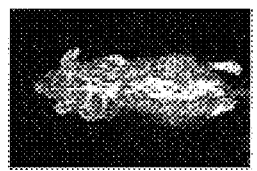 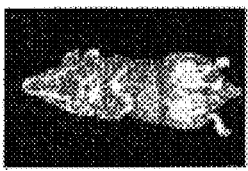 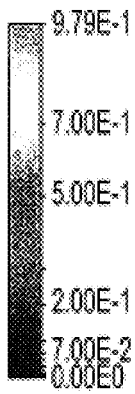 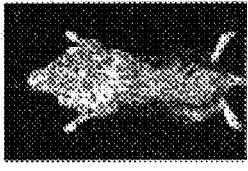 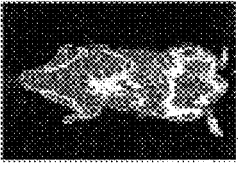
*Fig. 6C*  *Fig. 6D*  *Fig. 6M*  *Fig. 6N*
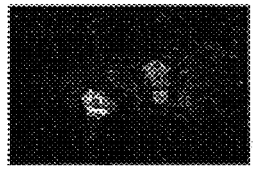 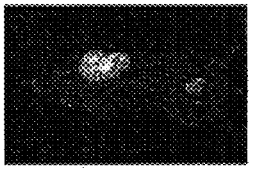 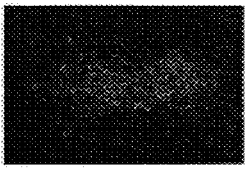 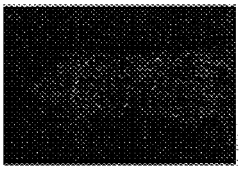
*Fig. 6E*  *Fig. 6F*  *Fig. 6O*  *Fig. 6P*
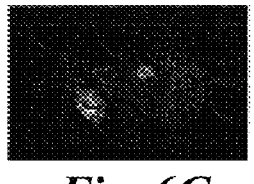 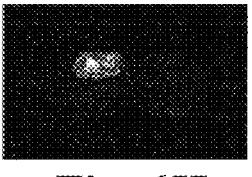 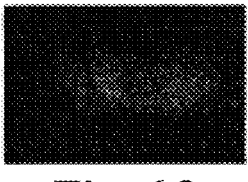 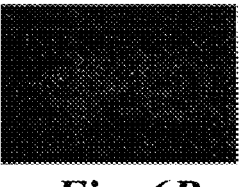
*Fig. 6G*  *Fig. 6H*  *Fig. 6Q*  *Fig. 6R*
  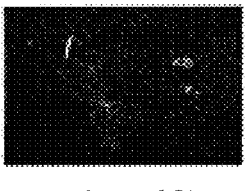 
*Fig. 6I*  *Fig. 6J*  *Fig. 6S*  *Fig. 6T*

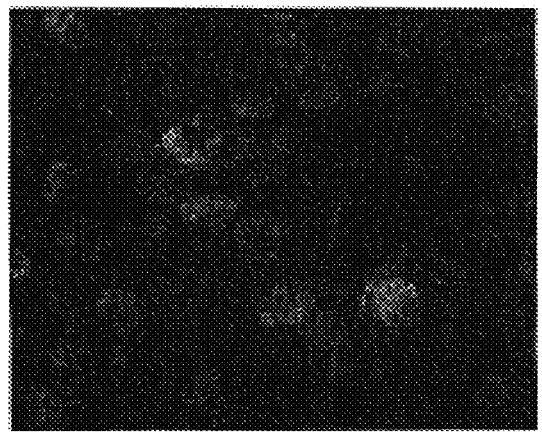
0 MIN
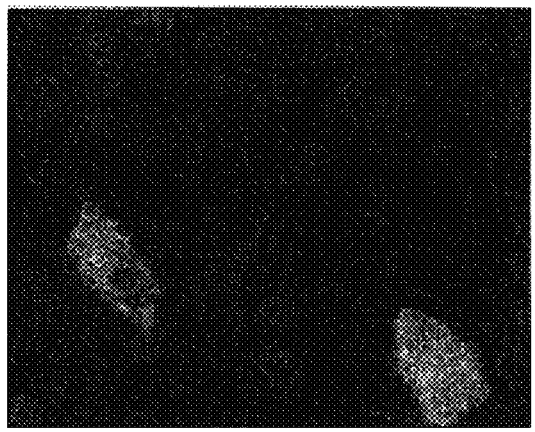
10 MIN
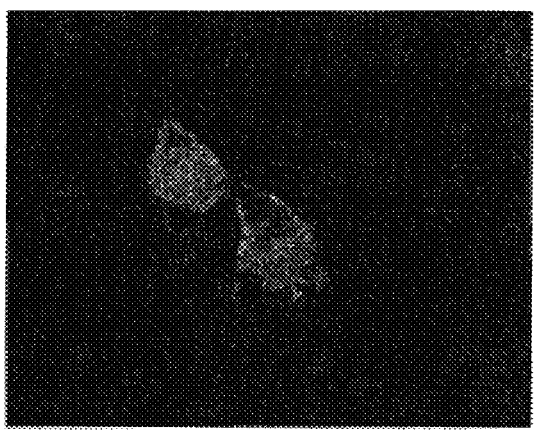
30 MIN
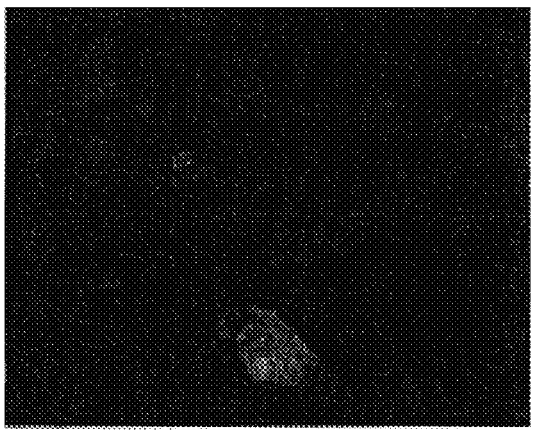
60 MIN
*Fig. 9*

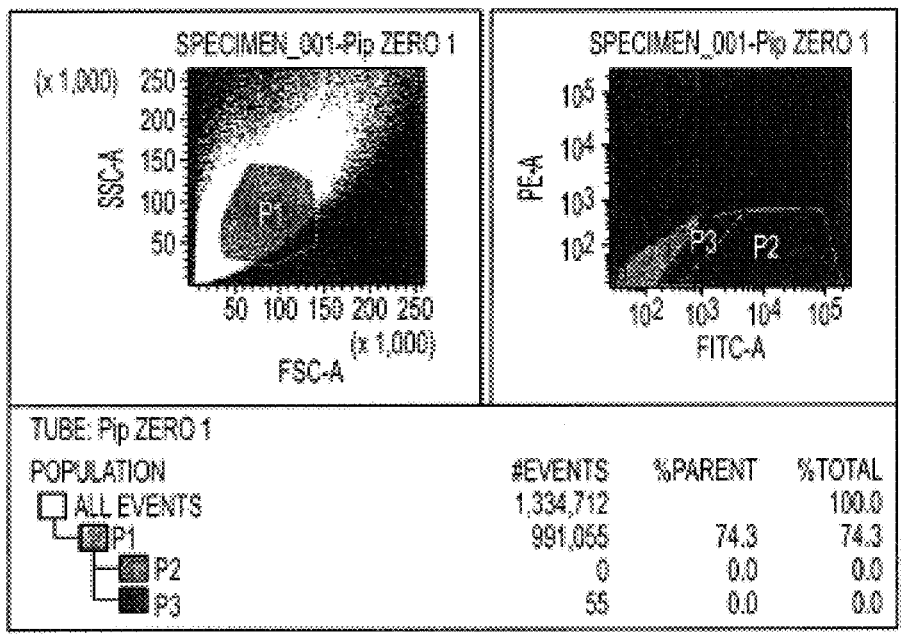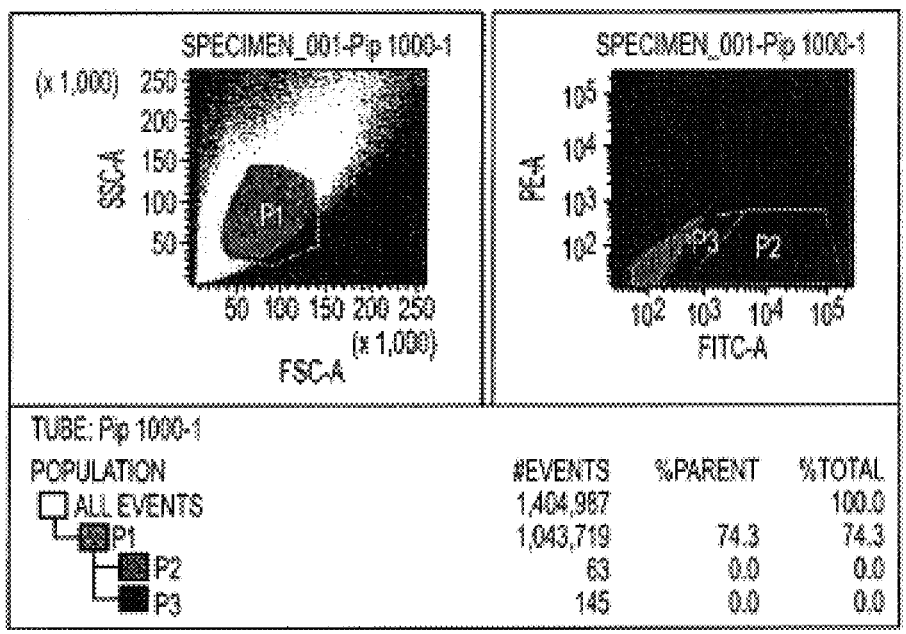
*Fig. 15A*

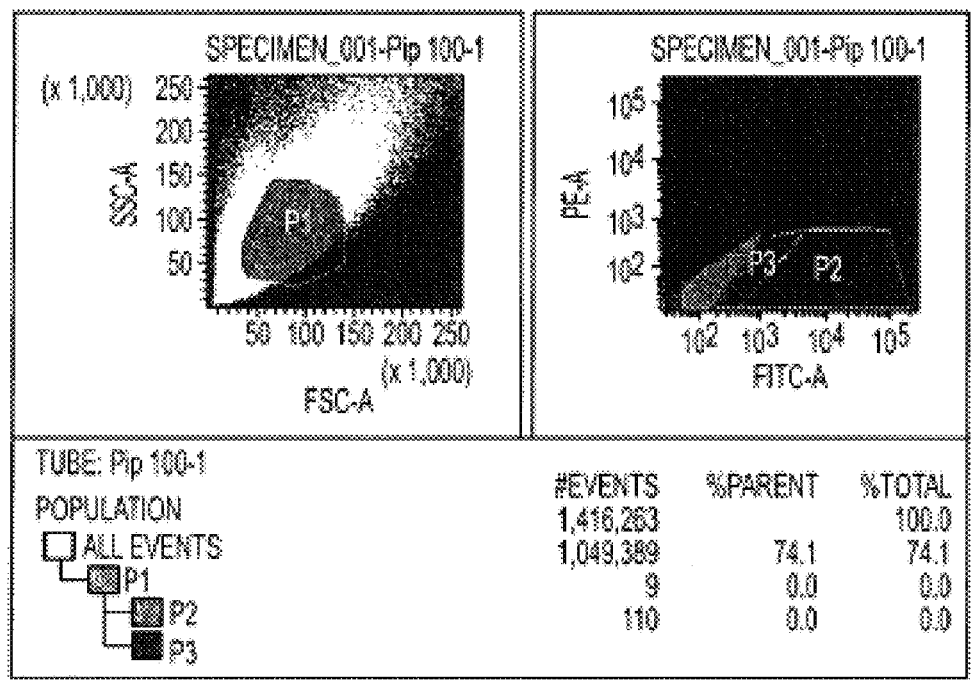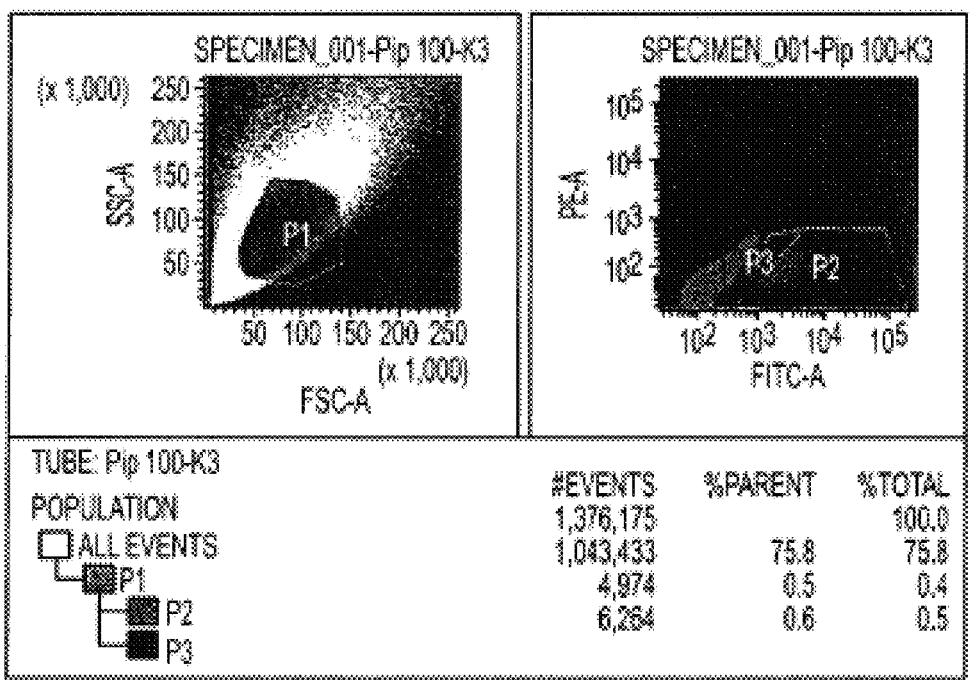
Fig. 15C

PSMA TARGETED FLUORESCENT AGENTS FOR IMAGE GUIDED SURGERY

CROSS-REFERENCE TO RELATED APPLICATIONS

This application is a continuation of U.S. patent application Ser. No. 16/704,137, filed Dec. 5, 2019, which is a continuation of U.S. patent application Ser. No. 15/618,788, filed Jun. 9, 2017, now abandoned, which claims the benefit of U.S. Provisional Application No. 62/324,097, filed Apr. 18, 2016, and is a continuation-in-part of U.S. patent application Ser. No. 14/243,535, filed Apr. 2, 2014, now U.S. Pat. No. 9,776,977 issued Oct. 3, 2017, which is a divisional of U.S. patent application Ser. No. 13/257,499 filed Sep. 19, 2011, and now U.S. Pat. No. 9,056,841 issued Jun. 16, 2015, which is a 35 U.S.C. § 371 National Stage Entry of International Application No. PCT/US2010/028020 having an international filing date of Mar. 19, 2010, which claims the benefit of U.S. Provisional Application No. 61/248,934 filed Oct. 6, 2009, U.S. Provisional Application No. 61/248,067 filed Oct. 2, 2009, U.S. Provisional Application No. 61/161,484 filed Mar. 19, 2009, and U.S. Provisional Application No. 61/161,485 filed Mar. 19, 2009, each of which is incorporated herein by reference in its entirety.

STATEMENT OF GOVERNMENTAL INTEREST

This invention was made with government support under CA092871 awarded by the National Institutes of Health. The government has certain rights in the invention.

BACKGROUND

Prostate cancer (PCa) is the most commonly diagnosed malignancy and the second leading cause of cancer-related death in men in the United States. Only one half of tumors due to PCa are clinically localized at diagnosis and one half of those represent extracapsular spread. Localization of that spread, as well as determination of the total body burden of PCa, has important implications for therapy.

Prostate-specific membrane antigen (PSMA) is a marker for androgen-independent disease that also is expressed on solid (nonprostate) tumor neovasculature. Complete detection and eradication of primary tumor and metastatic foci are required to effect a cure in patients with cancer; however, current preoperative assessment often misses small metastatic deposits. Accordingly, more sensitive imaging techniques are required, including those that can allow visualization of the tumor during surgery.

SUMMARY

In some aspects, the presently disclosed subject matter provides the following compound:

(3)

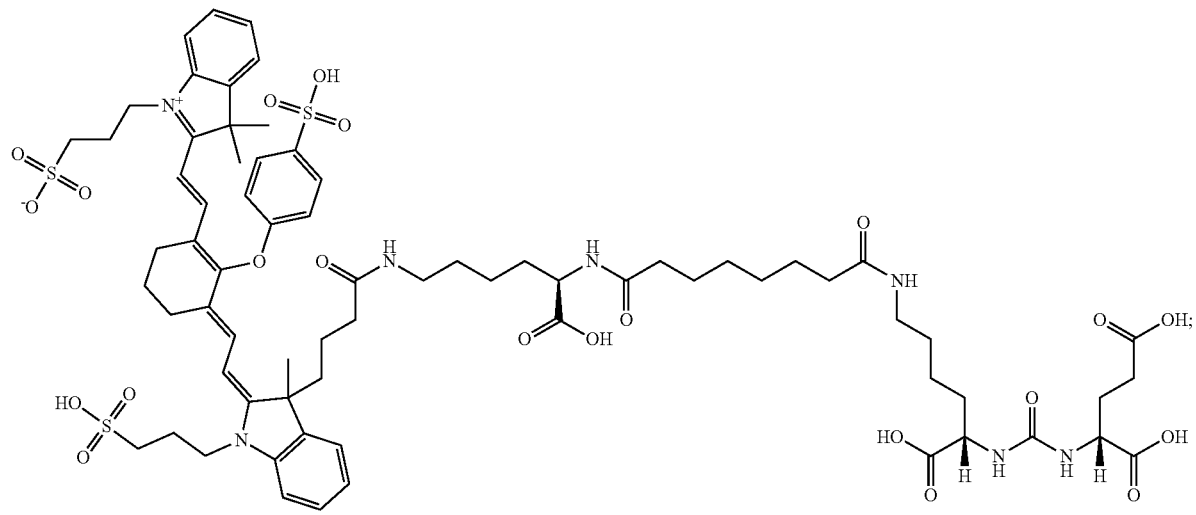

or a pharmaceutically acceptable salt thereof.

In other aspects, the presently disclosed subject matter provides a composition comprising compound (3), as provided immediately hereinabove, wherein the composition is adapted for visualization of tissue under illumination with near-infrared radiation. In certain aspects, the composition is adapted for administration to a subject. In yet more certain aspects, the composition comprises a unit dosage form of compound (3). In particular aspects, the unit dosage form delivers to the subject an amount of compound (3) between about 0.01 and about 8 mg/kg. In more particular aspects, the unit dosage form delivers to the subject an amount of compound (3) of about 0.01 mg/kg, about 0.05 mg/kg, about 0.10 mg/kg, about 0.20 mg/kg, about 0.3 mg/kg, about 0.35 mg/kg, about 0.40 mg/kg, about 0.45 mg/kg, about 0.50 mg/kg, about 0.55 mg/kg, about 0.60 mg/kg, about 0.65 mg/kg, about 0.70 mg/kg, about 0.75 mg/kg, about 0.80 mg/kg, about 0.90 mg/kg, about 1 mg/kg, about 2, mg/kg, about 4 mg/kg, about 6 mg/kg, or about 8 mg/kg. In particular aspects, the composition is in a single dose form.

In certain aspects, the composition is in dry form. In more certain aspects, the composition is lyophilized in a sterile container. In particular aspects, the composition is contained within a sterile container. In yet more particular aspects, the sterile container comprises a machine detectable identifier.

In some aspects, the composition further comprises one or more pharmaceutically acceptable excipients in an oral dosage form. In other aspects, the composition further comprises one or more pharmaceutically acceptable carriers in an injectable dosage form. In certain aspects, the composition further comprises one or more pharmaceutically acceptable excipients in a dosage form for direct delivery to a surgical site.

In other aspects, the presently disclosed subject matter provides for the use of a composition comprising compound (3) for administration to a subject to obtain visualization of tissue expressing PSMA under illumination with near-infrared radiation. In certain aspects, the subject is a human subject.

In other aspects, the presently disclosed subject matter provides a method for visualization of tissue expressing PSMA, the method comprising administering to a subject a composition comprising compound (3), wherein compound (3) is administered in an amount sufficient for imaging tissue under illumination with near-infrared radiation; imaging the tissue under illumination with near-infrared radiation; and obtaining at least one image of tissue from the subject.

In certain aspects, the composition comprises a unit dosage form of compound (3). In more certain aspects, the unit dosage form delivers to the subject an amount of compound (3) from about 0.01 mg/kg and about 8 mg/kg. In particular aspects, the composition is sterile, non-toxic, and adapted for administration to a subject.

In certain aspects, the method further comprises obtaining the image during administration, after administration, or both during and after administration of the composition. In other aspects, the method further comprises intravenously injecting a composition comprising compound (3) into the subject. In particular aspects, the composition is injected into a circulatory system of the subject.

In certain aspects, the method further comprises visualizing a subject area on which surgery is or will be performed.

In more certain aspects, the method further comprises performing a surgical procedure of the subject area based on the visualization of the area. In yet more certain aspects, the method further comprises viewing a subject area on which an ophthalmic, arthroscopic, laparoscopic, cardiothoracic, muscular, or neurological procedure is or will be performed.

In certain aspects, the method further comprises diagnosing the subject with a condition or disease based on the visualization of the tissue expressing PSMA. In more certain aspects, the method further comprises obtaining ex vivo images of at least a portion of the subject. In particular aspects, the tissue being visualized comprises tumor tissue. In more particular aspects, the tissue being visualized comprises cancerous tissue. In even more particular aspects, the tissue being visualized comprises prostate tissue. In even yet more particular aspects, the tissue being visualized comprises prostate tumor tissue. In other aspects, the tissue being visualized comprises nerve tissue.

In further aspects, the presently disclosed subject matter provides a compound having the structure:

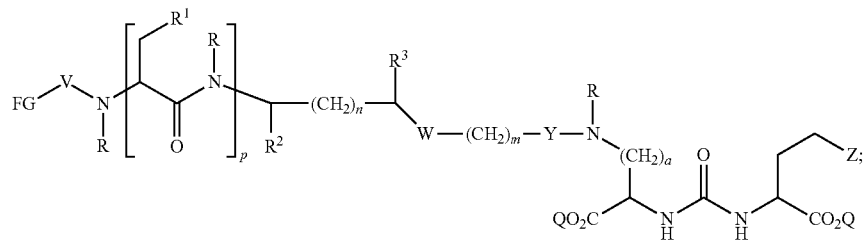

wherein: Z is tetrazole or $CO_2Q$; each Q is independently selected from hydrogen or a protecting group; FG is a fluorescent dye moiety which emits in the visible or near infrared spectrum; each R is independently H or $C_1$-$C_4$ alkyl; V is —C(O)—; W is —NRC(O); Y is —C(O); a is 1, 2, 3, or 4; m is 1, 2, 3, 4, 5, or 6; n is 1, 2, 3, 4, 5 or 6; p is 0, 1, 2, or 3, and when p is 2 or 3, each $R^1$ may be the same or different; $R^1$ is H, $C_1$-$C_6$ alkyl, $C_6$-$C_{12}$ aryl, or alkylaryl having 1 to 3 separate or fused rings and from 6 to about 18 ring carbon atoms; $R^2$ and $R^3$ are independently H, $CO_2H$, or $CO_2R^4$, where $R^4$ is a $C_1$-$C_6$ alkyl, $C_6$-$C_{12}$ aryl, or alkylaryl having 1 to 3 separate or fused rings and from 6 to about 18 ring carbon atoms, wherein when one of $R^2$ and $R^3$ is $CO_2H$ or $CO_2R^4$, the other is H.

In certain aspects, the compound has the following structure:

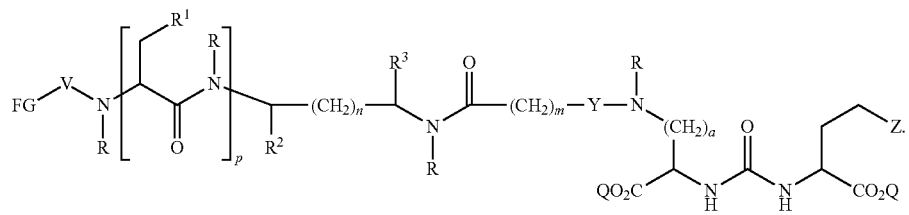

In more certain aspects, the compound has the following structure:

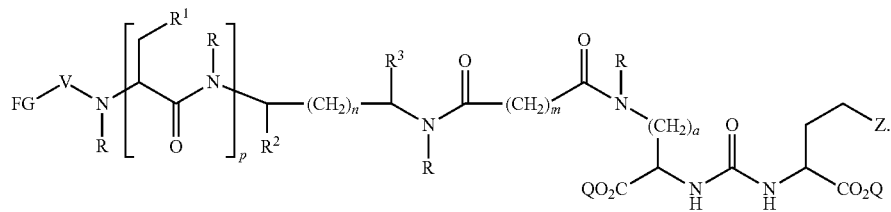

In yet more certain aspects, the compound has the following structure:

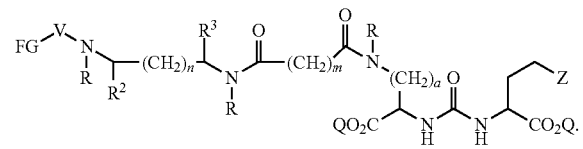

In particular aspects, $R^3$ is $CO_2H$ and $R^2$ is H or $R^2$ is $CO_2H$ and $R^3$ is H. In other aspects, $R^2$ is $CO_2R^4$ and $R^3$ is H or $R^3$ is $CO_2R^4$, and $R^2$ is H. In yet other aspects, $R^2$ is H, and $R^3$ is H.

In certain aspects, $R^4$ is $C_6$-$C_{12}$ aryl, or alkylaryl having 1 to 3 separate or fused rings and from 6 to about 18 ring carbon atoms. In certain aspects, $R^1$ is $C_6$-$C_{12}$ aryl. In more certain aspects, $R^1$ is phenyl.

In particular aspects, FG is a fluorescent dye moiety which emits in the near infrared spectrum. In more particular aspects, FG comprises a fluorescent dye moiety selected from the group consisting of carbocyanine, indocarbocyanine, oxacarbocyanine, thiacarbocyanine and merocyanine, polymethine, coumarine, rhodamine, xanthene, fluorescein, boron-dipyrromethane (BODIPY), Cy5, Cy5.5, Cy7, VivoTag-680, VivoTag-S680, VivoTag-S750, AlexaFluor660, AlexaFluor680, AlexaFluor700, AlexaFluor750, AlexaFluor790, Dy677, Dy676, Dy682, Dy752, Dy780, DyLight547, Dylight647, HiLyte Fluor 647, HiLyte Fluor 680, HiLyte Fluor 750, IRDye 800CW, IRDye 800RS, IRDye 700DX, ADS780WS, ADS830WS, and ADS832WS. In yet more particular aspects, FG has a structure selected from the group consisting of:

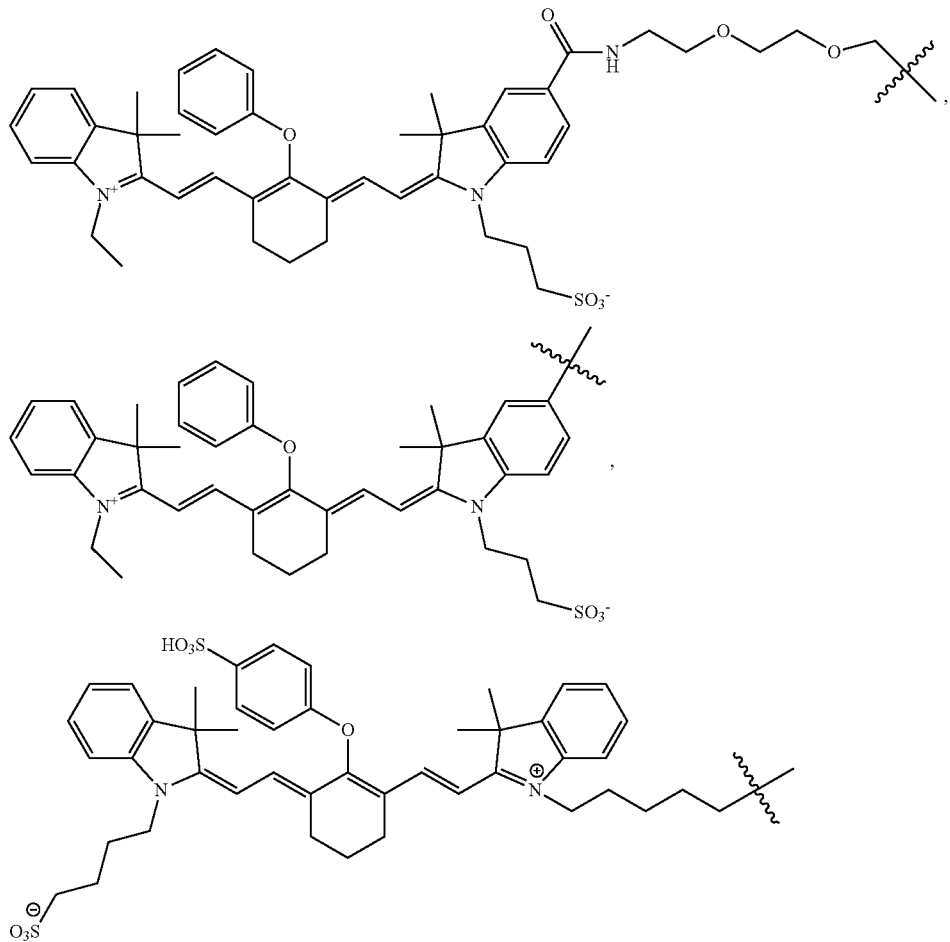

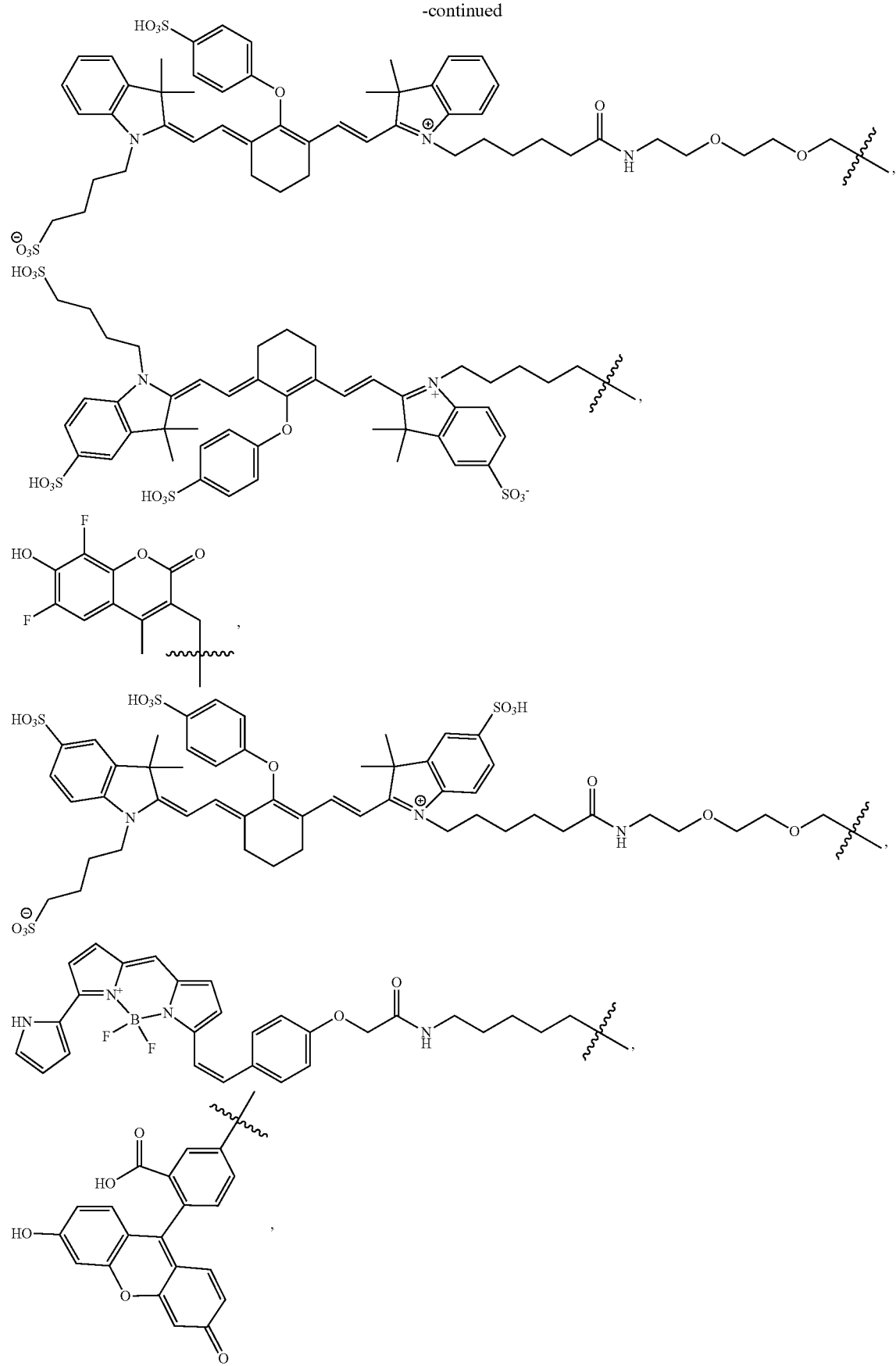

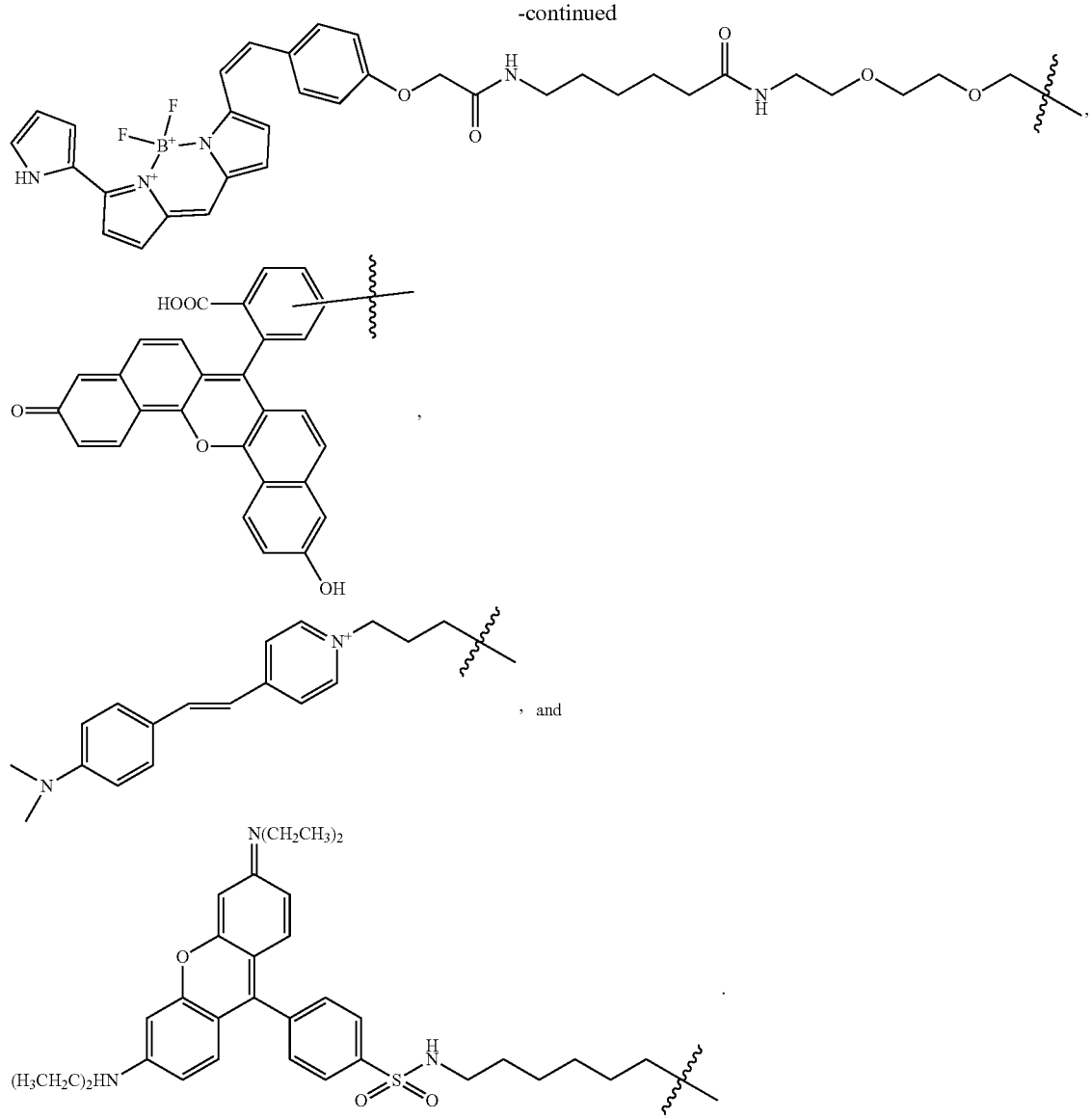
In some aspects, the compound is selected from the group consisting of:
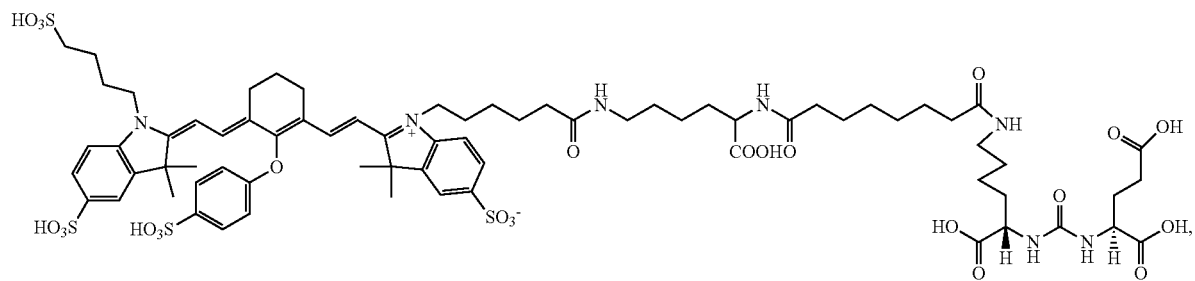

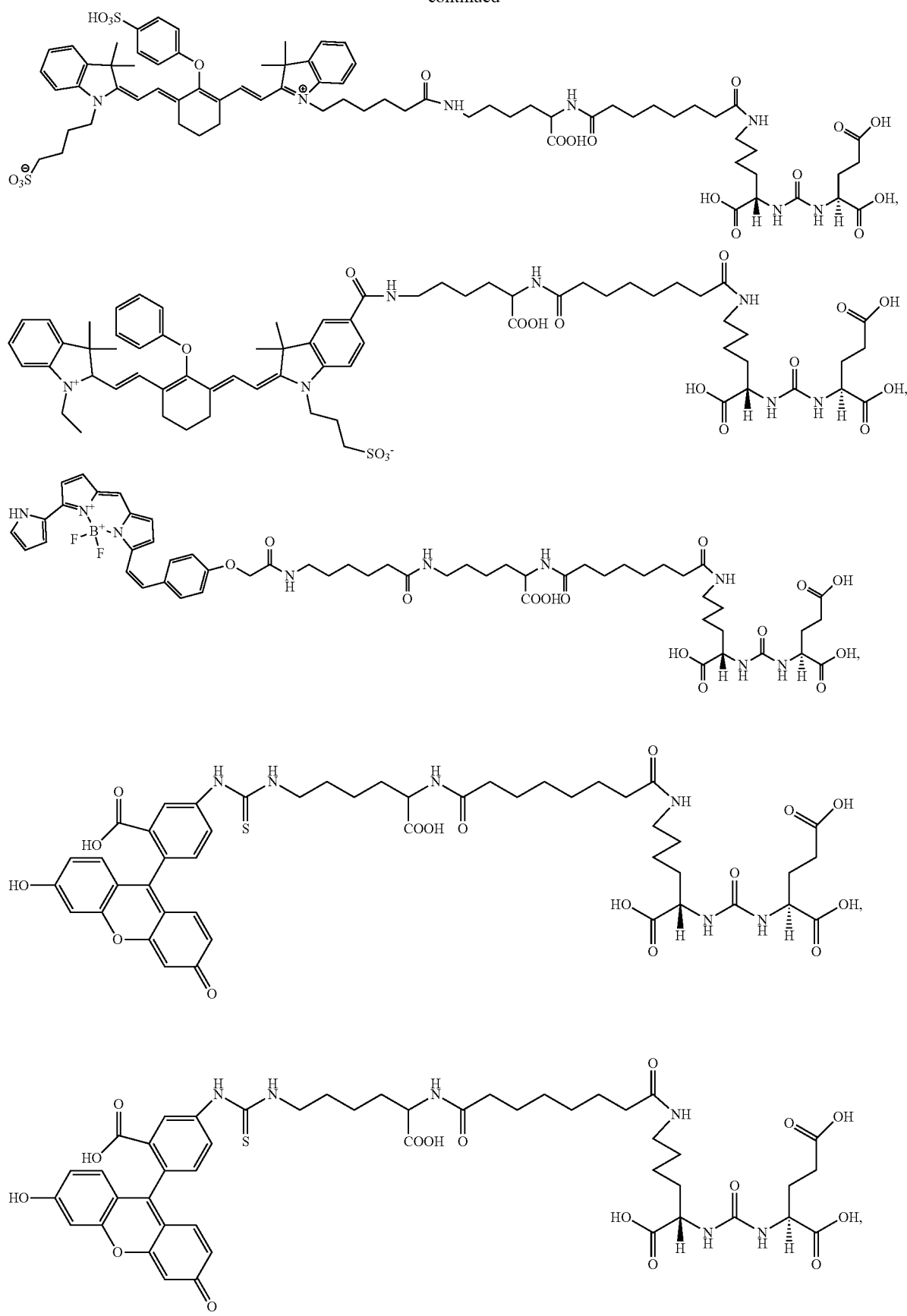

-continued

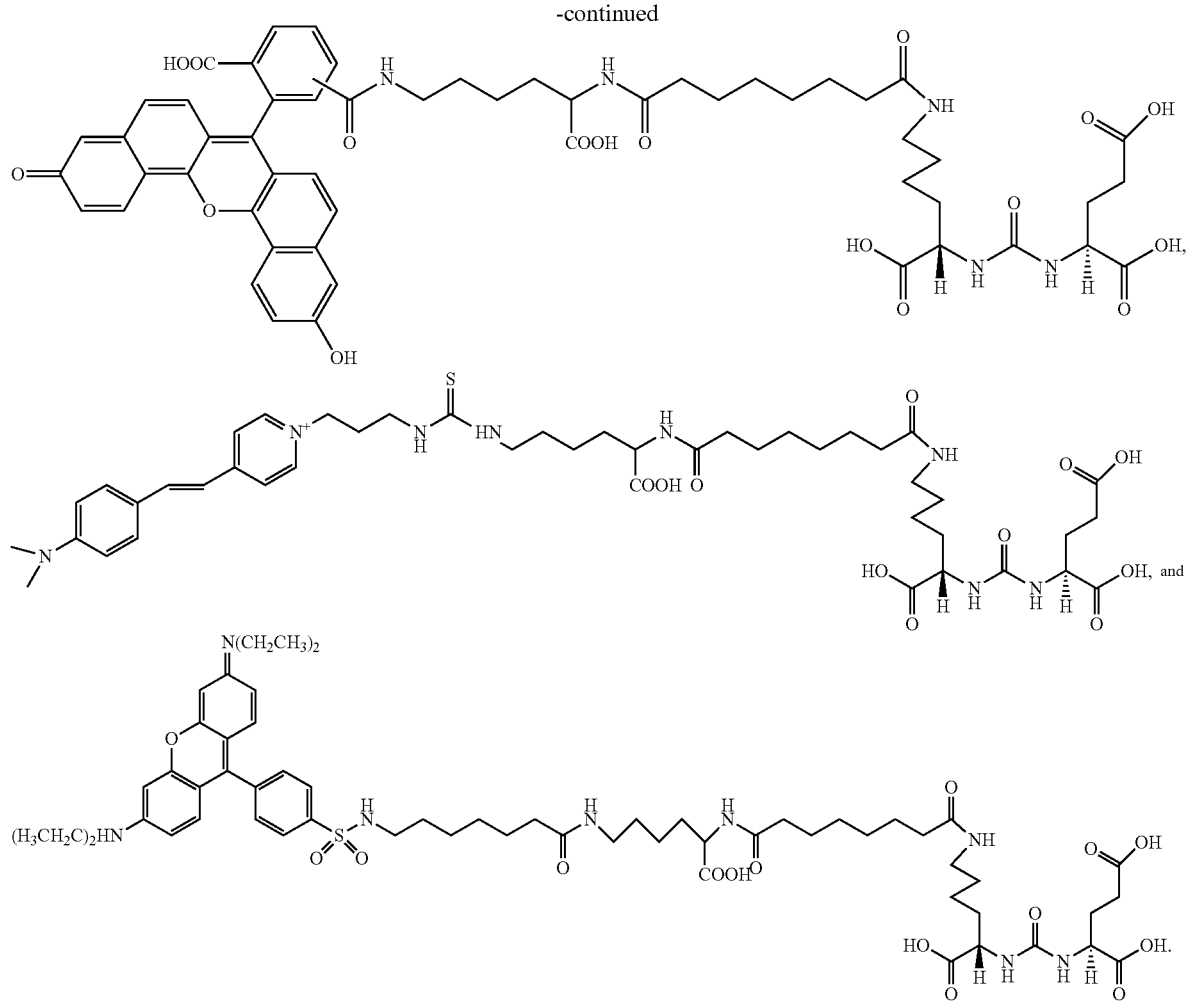

In other aspects, the presently disclosed subject matter provides a method of imaging one or more cells, organs or tissues by exposing the cell to or administering to an organism an effective amount of a presently disclosed compound, where the compound includes a fluorescent dye moiety suitable for imaging.

In yet other aspects, the presently disclosed subject matter provides a method for sorting cells by exposing the cells to a presently disclosed compound, where the compound includes a fluorescent dye moiety, followed by separating cells which bind the compound from cells which do not bind the compound.

In other aspects, the presently disclosed subject matter provides a method for intraoperative tumor mapping comprising administering an effective amount of a presently disclosed compound, where the compound includes a fluorescent dye moiety.

In yet other aspects, the presently disclosed subject matter provides a kit comprising a presently disclosed compound.

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE FIGURES

The patent or application file contains at least one drawing executed in color. Copies of this patent or patent application publication with color drawings will be provided by the Office upon request and payment of the necessary fee.

Figure 2:
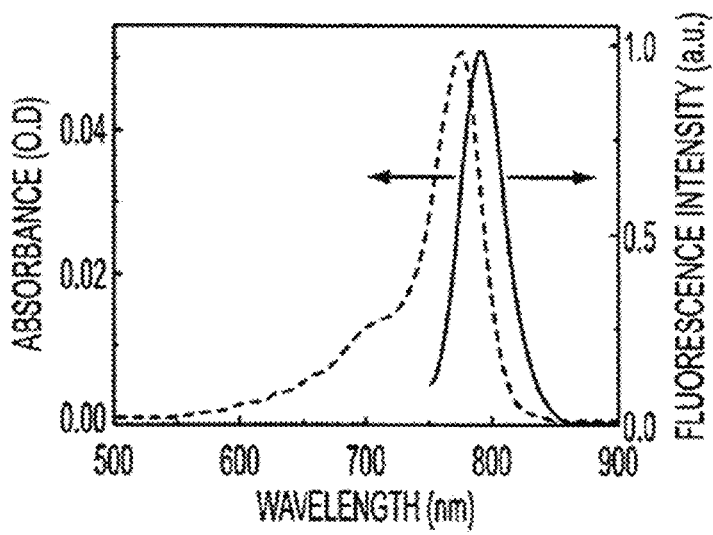
Figure 3:
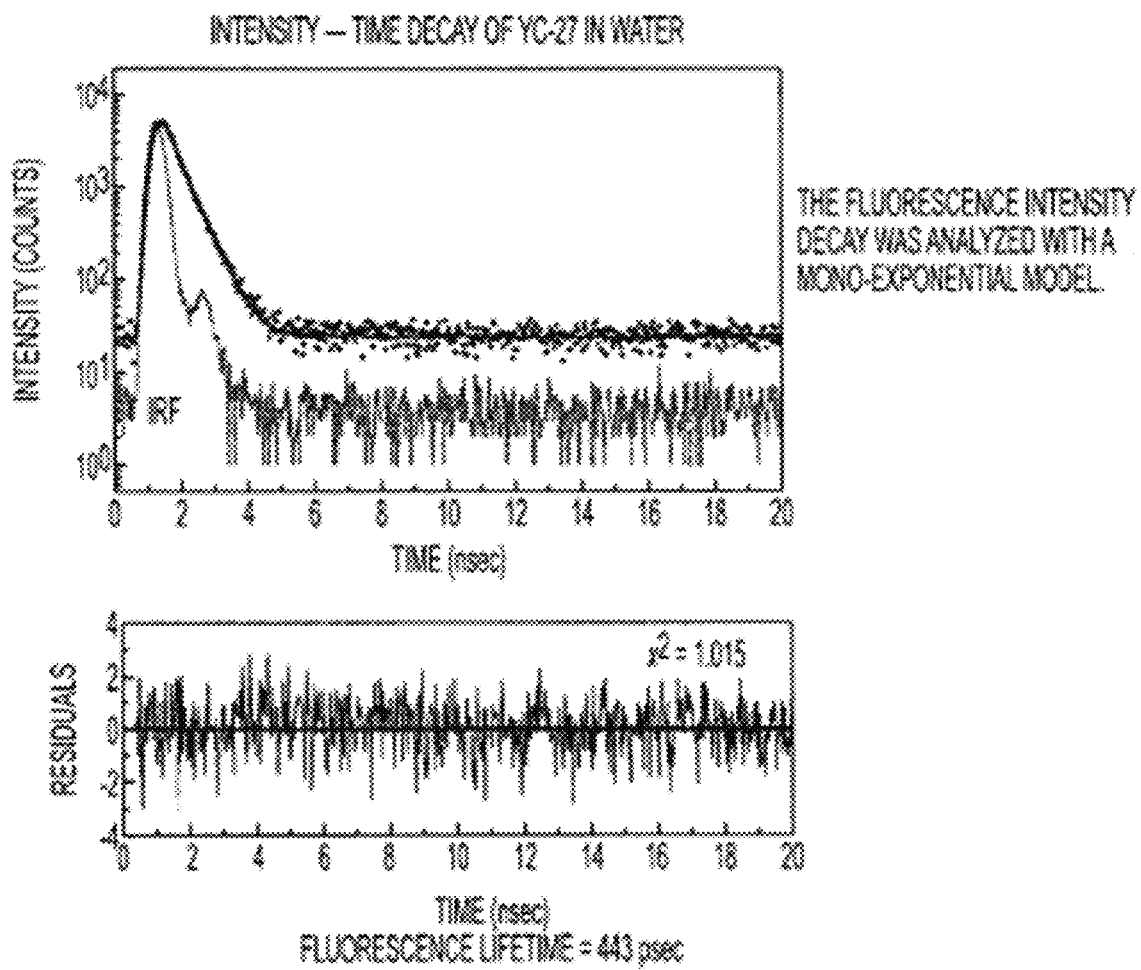
Figure 4:
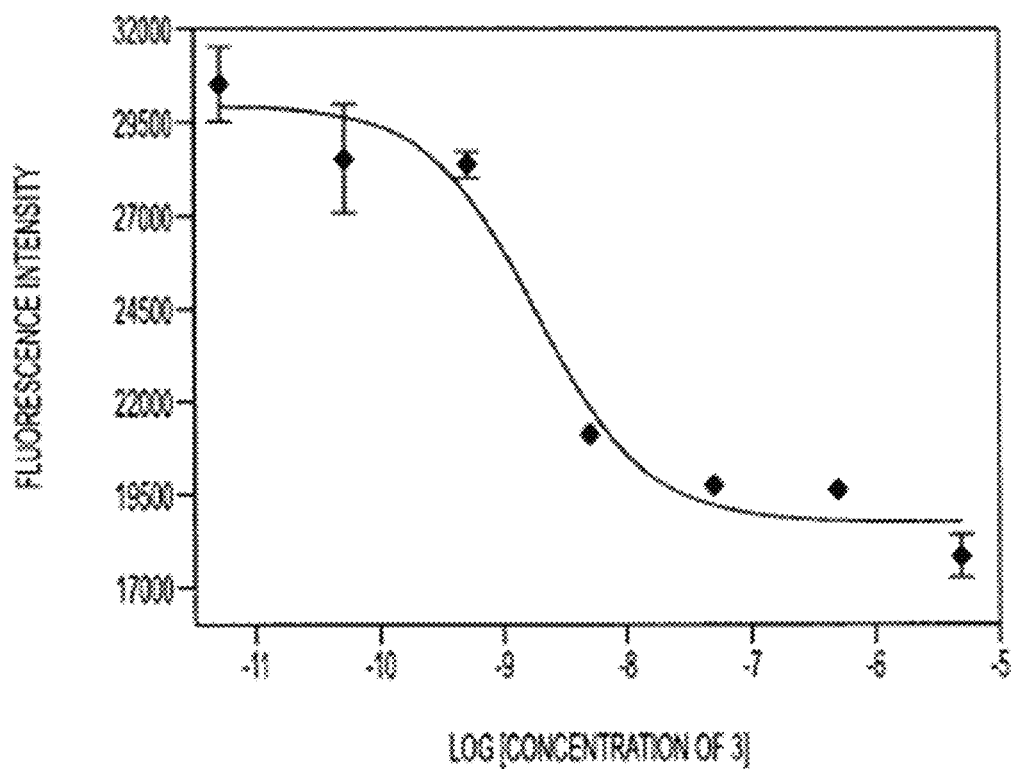
Figure 7:
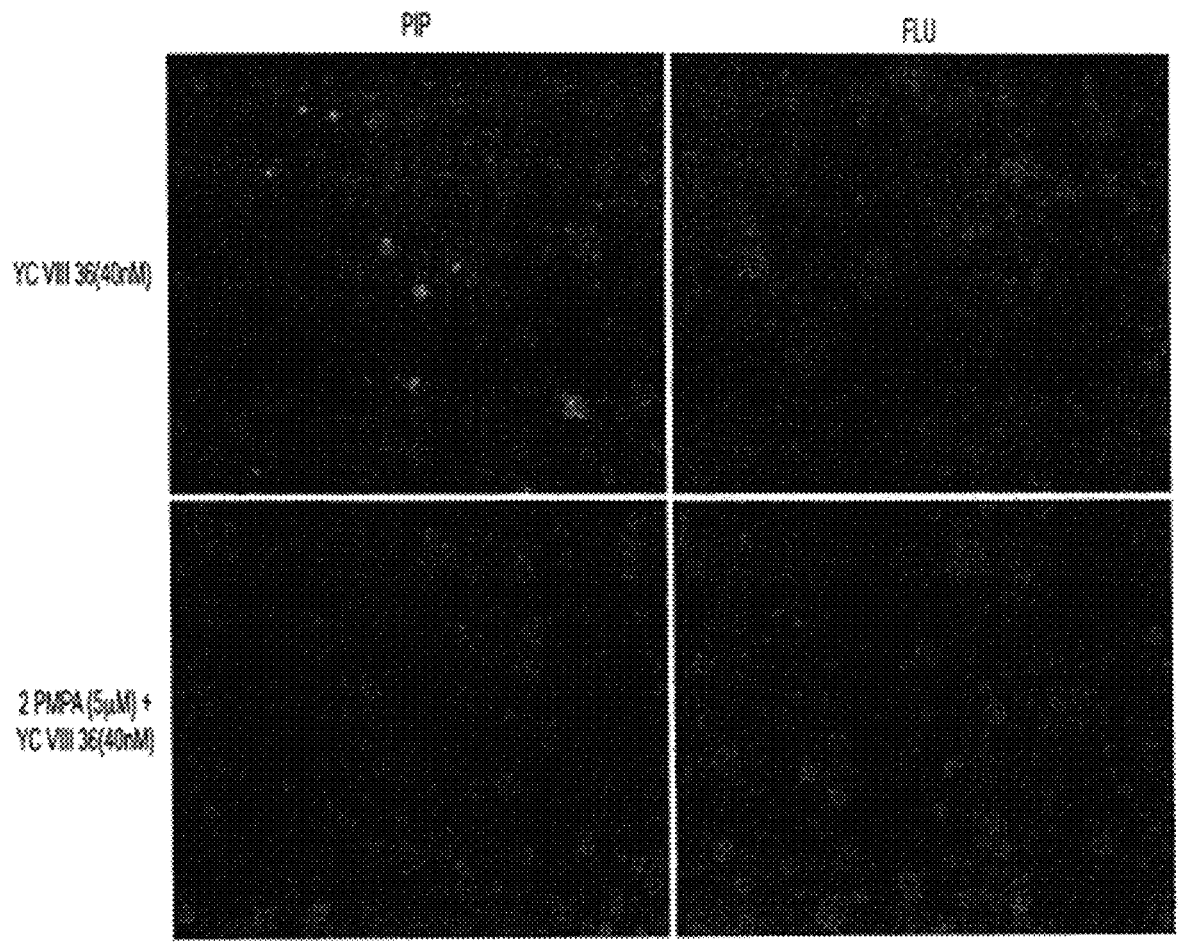
Figure 8:
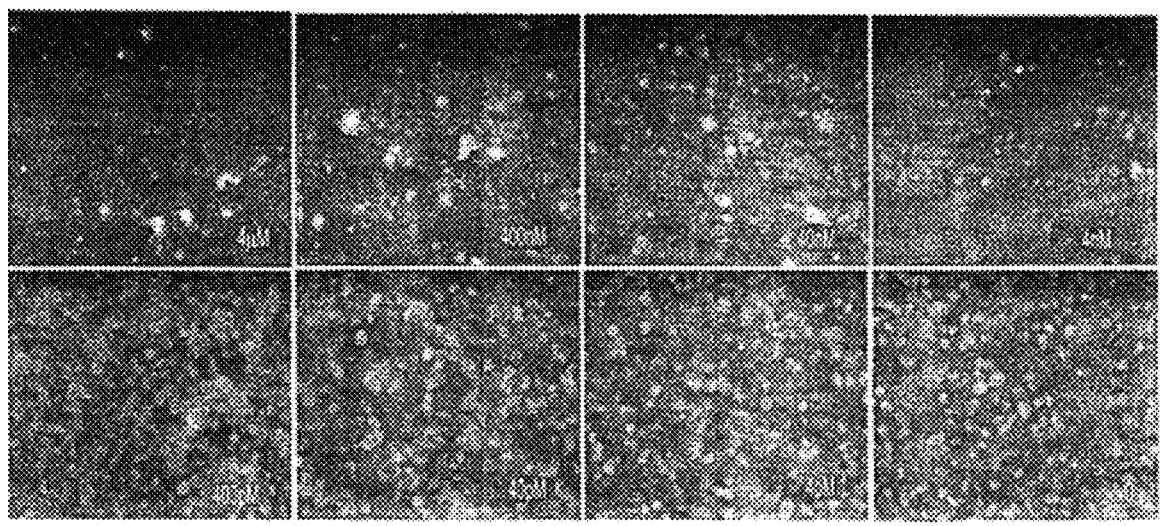
Figure 10:
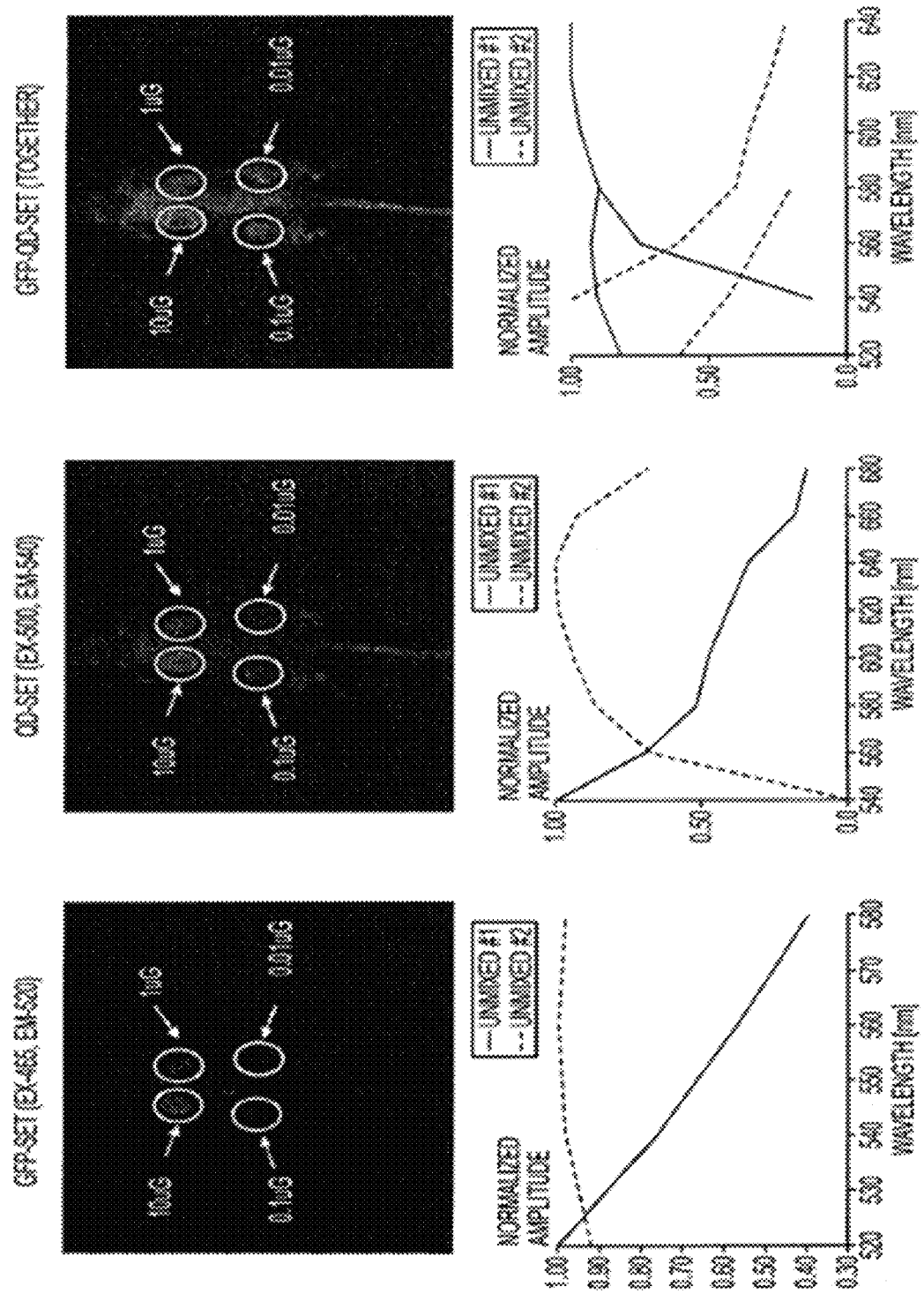
Figure 11:
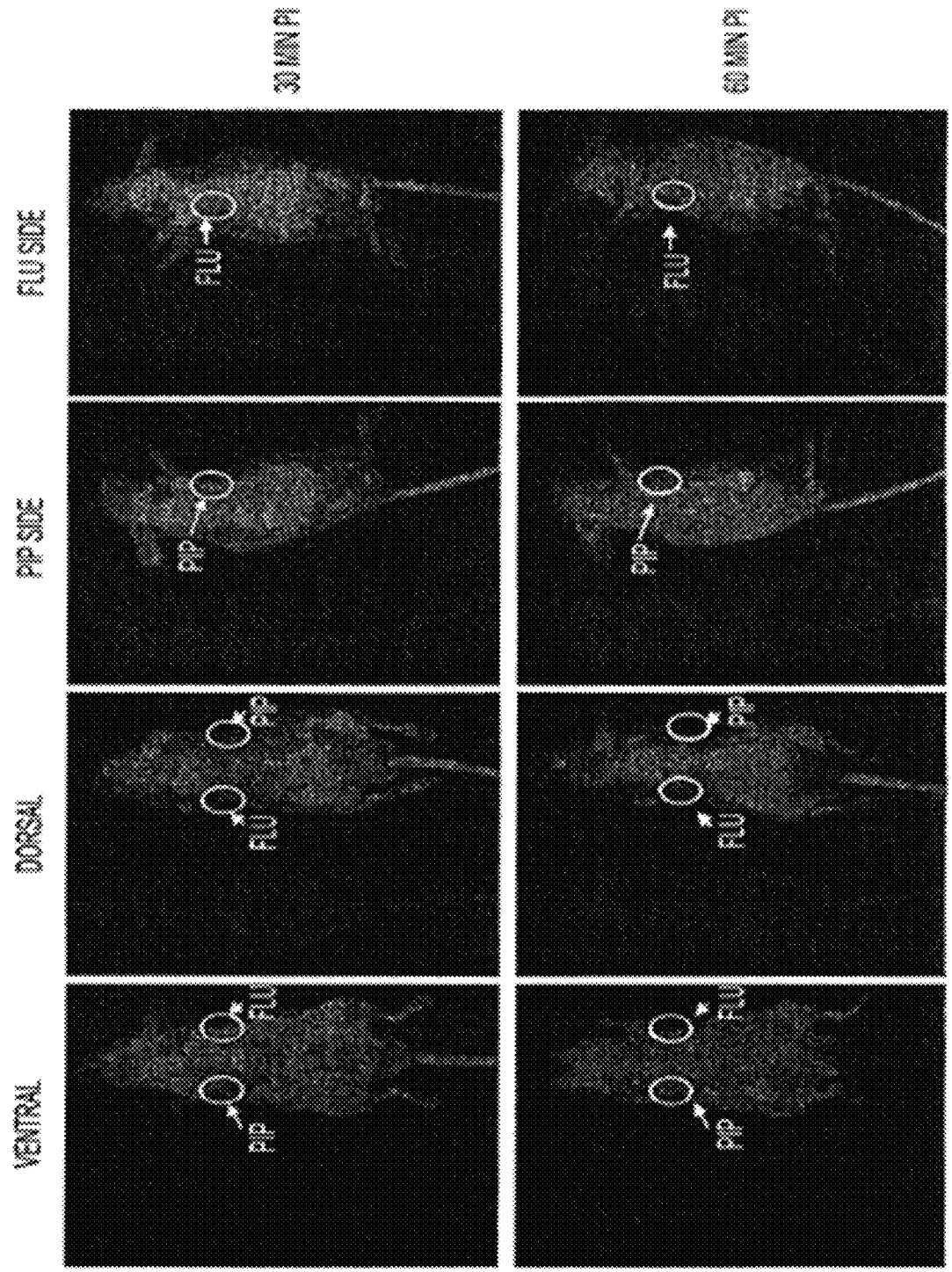
Figure 12:
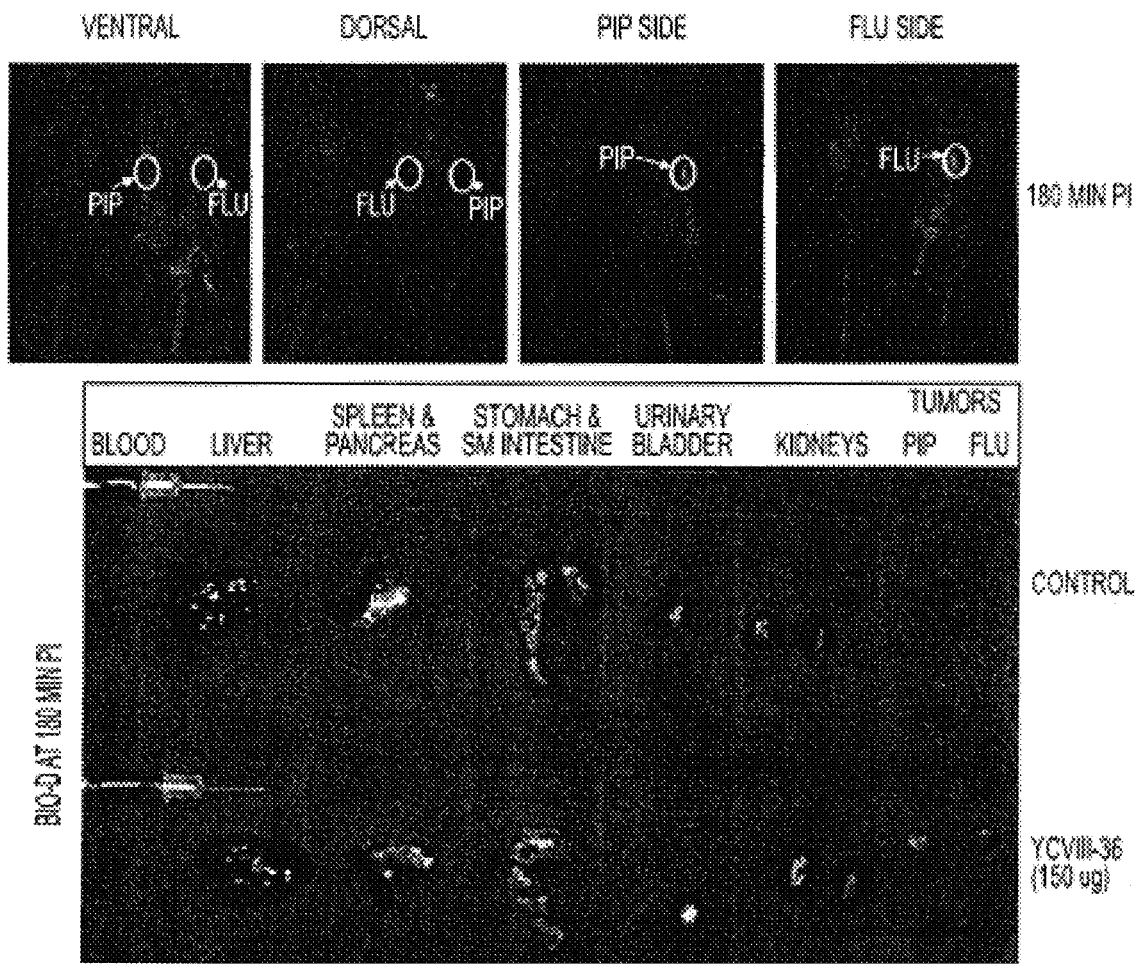

Having thus described the presently disclosed subject matter in general terms, reference will now be made to the accompanying Figures, which are not necessarily drawn to scale, and wherein:

FIG. 1 shows whole body and ex vivo organ imaging of mouse with PSMA$^+$ PC3 PIP tumor and PSMA$^-$ PC3 flu tumor at 24 h postinjection of 1 nmol of DyLight800-3;

FIG. 2 shows the absorbance and emission spectra, and quantum yield of exemplary compound YC-27;

FIG. 3A and FIG. 3B show the fluorescence decay of exemplary compound YC-27;

FIG. 4 shows an IC$_{50}$ curve of compound YC-27 using a fluorescence-based NAALADase assay;

FIG. 5A-FIG. 5O show in vivo imaging of a NOD/SCID mouse (mouse #1), bearing PC3-PIP (forward left flank) and PC3-flu (forward right flank) tumors. Mouse #1 received 10 nmol of YC-27 and dorsal (animal prone) and ventral (animal supine) views were obtained. Dorsal and ventral views at 40 min p.i. (FIG. 5A, FIG. 5B, respectively); 18.5 h (FIG. 5C, FIG. 5D); 23 h (FIG. 5E, FIG. 5F); 42.5 h (FIG.

Figure 13:
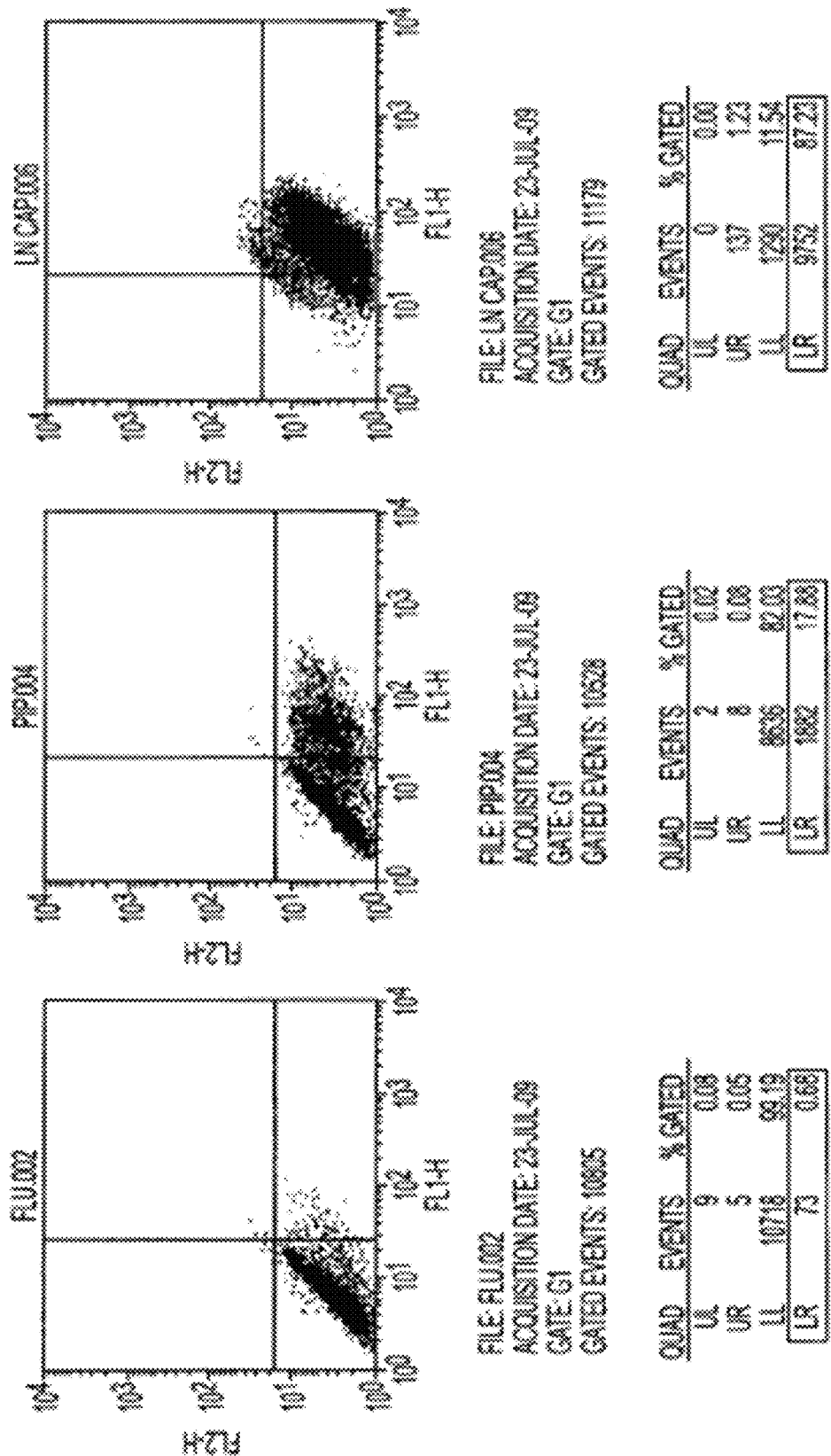
Figure 14:
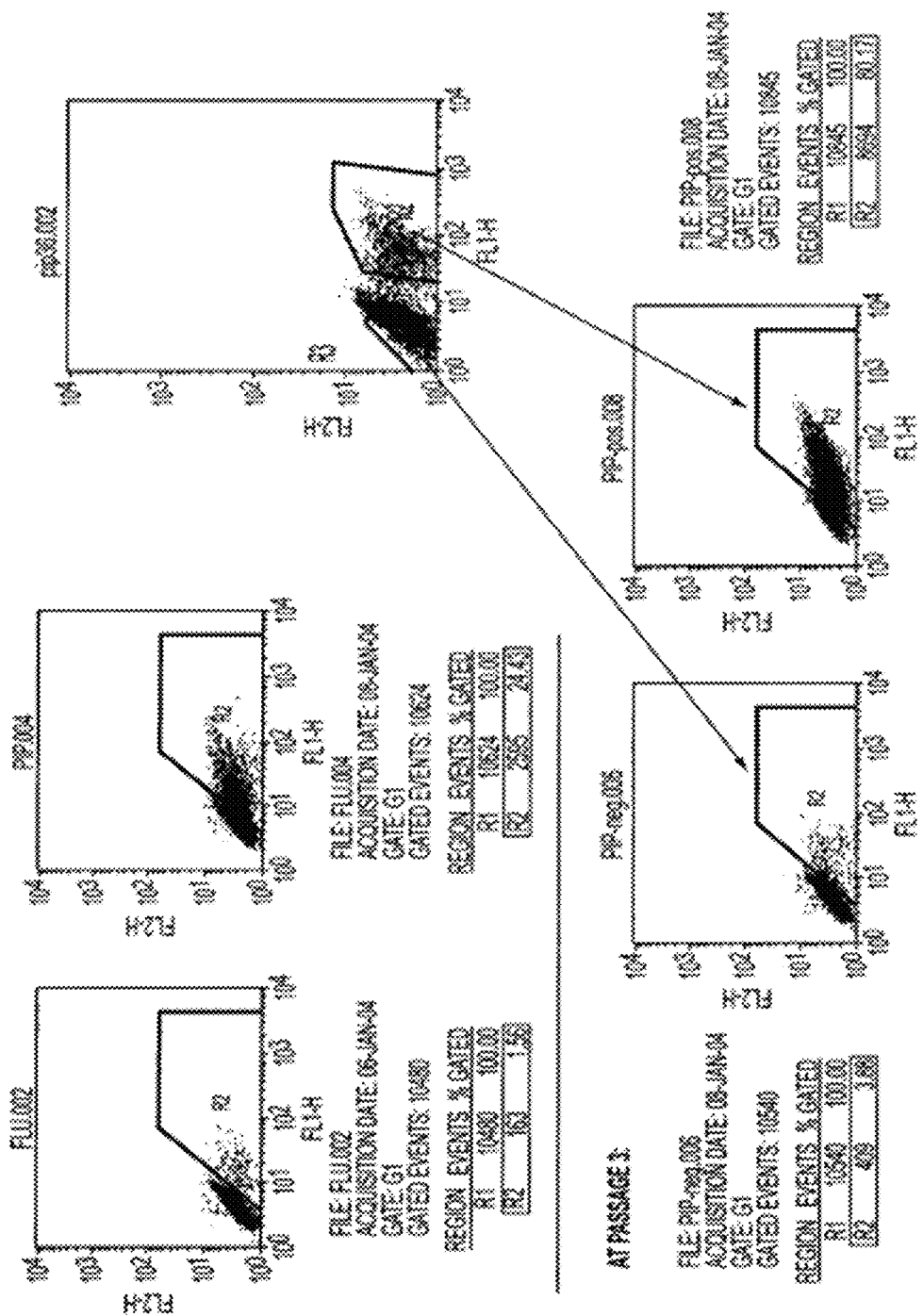
Figure 15B:
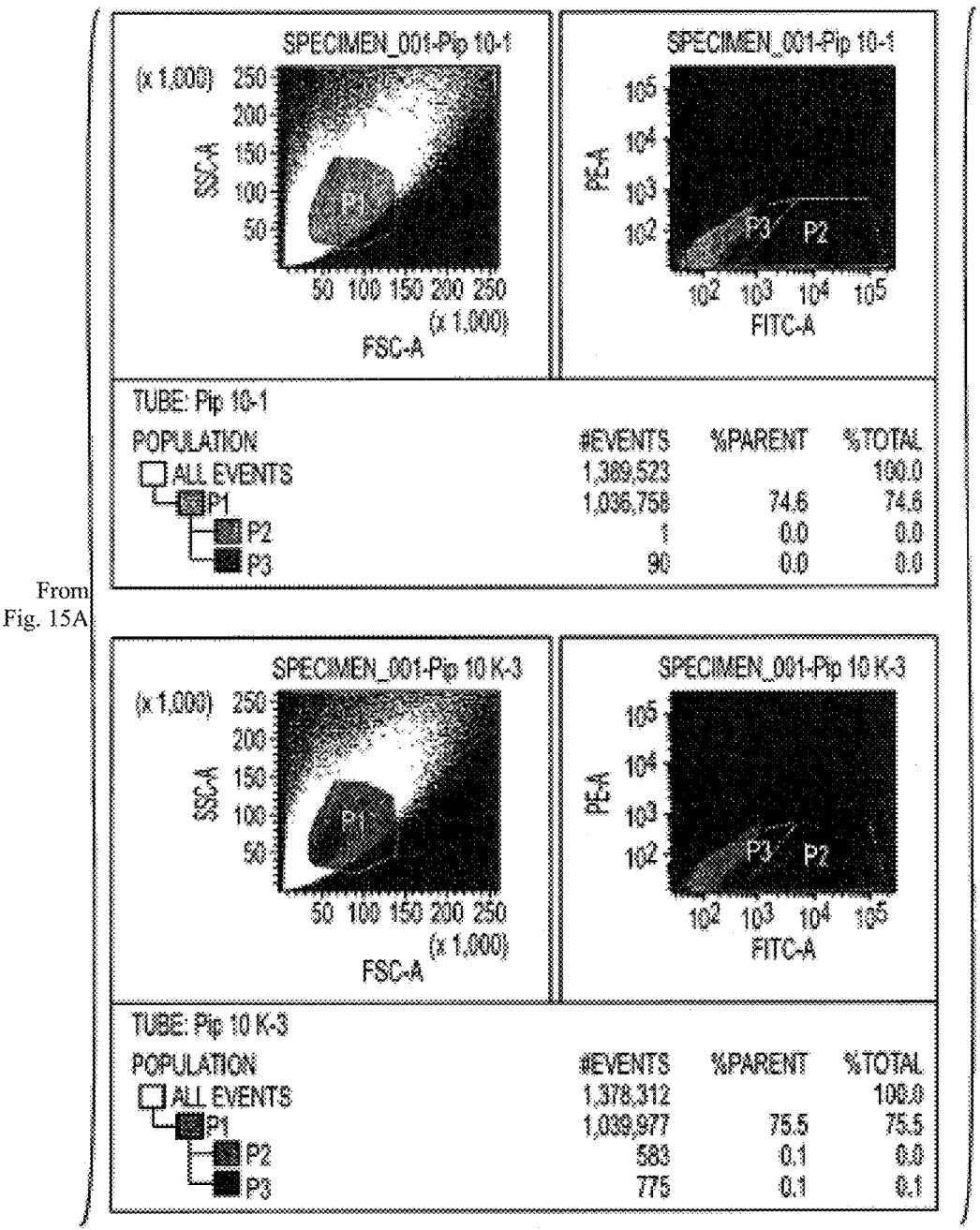

5G, FIG. 5H); 68 h (FIG. 5I, FIG. 5J). Dorsal view of pre-injection image (FIG. 5K). Dorsal and ventral views 70.5 h p.i. (FIG. 5L, FIG. 5M). Images after midline laparotomy (FIG. 5N) and individually harvested organs (FIG. 5O) on a Petri dish at 70.5 h p.i.. Images were scaled to the same maximum (arbitrary units);

FIG. 6A-FIG. 6T show in vivo imaging of a NOD/SCID mouse (mouse #2) (left panel), bearing PC3-PIP (forward left flank) and PC3-flu (forward right flank) tumors. Mouse #2 received 1 nmol of YC-27 and dorsal (animal prone) and ventral (animal supine) views were obtained. Dorsal and ventral views of the pre-injection image (FIG. 6A, FIG. 6B, respectively); 10 min p.i. (FIG. 6C, FIG. 6D); 20.5 h (FIG. 6E, FIG. 6F); 24 h (FIG. 6G, FIG. 6H). Images after midline laparotomy (FIG. 6I) and individually harvested organs (FIG. 6J) on a Petri dish at 24 h p.i.. Right Panels: Mouse #3 in same orientation as mouse #2. Mouse #3 received 1 nmol of YC-27 co-injected with 1 μmol of DCIBzL, which served as a blocking agent to test binding specificity. Images were scaled to the same maximum (arbitrary units);

FIG. 7A-FIG. 7D show PC3-PIP and PC3-flu cells treated with fluorescent compound YC-VIII-36 (green, top left) and DAPI (blue), and PC3-PIP and PC3-flu cells treated with both YC-VIII-36 and PSMA inhibitor, PMPA;

FIG. 8A-FIG. 8H show PC3-PIP cells treated with DAPI (blue) and varying concentrations of YC-VIII-36 (green);

FIG. 9A-FIG. 9D show time dependent internalization of YC-VIII-36 into PC3-PIP cells treated with YC-VIII-36 (green) and DAPI (blue);

FIG. 10A-FIG. 10F show titration and detection of varying amounts of YC-VIII-36 injected subcutaneously into a nude mouse. (IVIS spectrum with 10 second exposure followed by spectral unmixing);

FIG. 11A-FIG. 11H show fluorescence images of a PSMA+ PC3-PIP and PSMA− PC3-flu tumor-bearing mouse injected intravenously with exemplary compound YC-VIII-36;

FIG. 12A-FIG. 12E show fluorescence images of a PSMA+ PC3-PIP and PSMA− PC3-flu tumor-bearing mouse injected intravenously with exemplary compound YC-VIII-36 180 minutes after injection (top) and biodistribution of exemplary compound YC-VIII-36 180 minutes after injection (bottom);

FIG. 13A-FIG. 13C show FACS analysis showing the percent subpopulation of PSMA positive cells in PC3-flu, PC3-PIP, and LNCaP cells;

FIG. 14A-FIG. 14E show cell sorting results for PC3-PIP cells treated with exemplary compound YC-VIII-36, including initial percentage (top center), and after 3 passages of sorting (bottom); and FIG. 15A-FIG. 15F show the number of spiked PIP-pos cells into 10 million of PC3-flu detectable by 100 nM compound YC-VIII-36 in flow cytometry (BD LSR-II). Gate P1 is total number of single cells counted; gate P2 at higher intensity is the number of Pip-pos cells detected and gate P3 at lower intensity.

DETAILED DESCRIPTION

The presently disclosed subject matter now will be described more fully hereinafter with reference to the accompanying Figures, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

I. PSMA Targeted Fluorescent Agents for Image Guided Surgery

Minimally invasive medical techniques are intended to reduce the amount of extraneous tissue that is damaged during diagnostic or surgical procedures, thereby reducing patient recovery time, discomfort, and deleterious side effects. While millions of "open" or traditional surgeries are performed each year in the United States; many of these surgeries potentially can be performed in a minimally invasive manner. One effect of minimally invasive surgery, for example, is reduced post-operative recovery time and related hospital stay. Because the average hospital stay for a standard surgery is typically significantly longer than the average stay for an analogous minimally invasive surgery, increased use of minimally invasive techniques could save millions of dollars in hospital costs each year. While many of the surgeries performed in the United States could potentially be performed in a minimally invasive manner, only a portion currently employ these techniques due to instrument limitations, method limitations, and the additional surgical training involved in mastering the techniques.

Minimally invasive telesurgical systems are being developed to increase a surgeon's dexterity, as well as to allow a surgeon to operate on a patient from a remote location. Telesurgery is a general term for surgical systems where the surgeon uses some form of remote control, e.g., a servo-mechanism, or the like, to manipulate surgical instrument movements rather than directly holding and moving the instruments by hand. In such a telesurgery system, the surgeon is provided with an image of the surgical site at the remote location. While viewing the surgical site on a suitable viewer or display, the surgeon performs the surgical procedures on the patient by manipulating master control input devices, which in turn control the motion of instruments. These input devices can move the working ends of the surgical instruments with sufficient dexterity to perform quite intricate surgical tasks.

Surgery is the most commonly used treatment for clinically localized prostate cancer (PCa) and provides a survival advantage compared to watchful waiting. A pressing issue in surgery for PCa is the assurance of a complete resection of the tumor, namely, a negative surgical margin. Surgical techniques, including minimally invasive surgical techniques, such as tele-surgical systems, can be further aided by improving visualization of the tissue where the procedure is to be carried out. One way to improve visualization of tissue is through the use of dyes capable of targeted visualization of tissue, allowing a surgeon to either remove or spare the tissue.

Accordingly, in some embodiments, the presently disclosed subject matter provides low-molecular-weight compounds comprising PSMA-targeting ligands linked to near-infrared (NIR), closed chain, sulfo-cyanine dyes and methods of their use for visualizing tissue under illumination with NIR radiation, including methods for imaging prostate cancer (PCa).

While a variety of radiolabeled PSMA-targeting antibodies have been used for tumor imaging, low molecular weight agents are preferred due to more tractable pharmacokinetics, i.e., more rapid clearance from nontarget sites. A series of fluorescent agents has been previously reported and was tested in mice to good effect. See, for example, international PCT patent application publication no. WO2010/108125A2, for PSMA-TARGETING COMPOUNDS AND USES THEREOF, to Pomper et al., published Sep. 23, 2010, which is incorporated by reference in its entirety. Because of the favorable pharmacokinetic profile of this class of compounds, i.e., low nonspecific binding, lack of metabolism in vivo and reasonable tumor residence times, this series of compounds was extended to include Dylight800 fluorescent dyes. Thus, the presently disclosed compounds include a urea-based PSMA binding moiety linked to a Dylight™ 800 fluorescent dye (Thermo Fisher Scientific Inc., Rockford, Ill., USA). The presently disclosed targeted fluorescent PSMA binding compounds may find utility in fluorescence image guided surgery and biopsy of PSMA positive tumors and tissues; the former providing visual confirmation of complete removal of PSMA-containing tissue.

A. Compound (3)

Accordingly, in some embodiments, the presently disclosed subject matter provides the following compound:

readily prepared by reaction between an amine and an isocyanate, or between an amine and an activated carbonamide (—NRC(O)—). Thioureas can be readily prepared from reaction of an amine with an isothiocyanate. Amides (—C(O)NR— or —NRC(O)—) can be readily prepared by reactions between amines and activated carboxylic acids or esters, such as an acyl halide or N-hydroxysuccinimide ester. Carboxylic acids may also be activated in situ, for example, with a coupling reagent, such as a carbodiimide, or carbonyldiimidazole (CDI). Esters may be formed by reaction between alcohols and activated carboxylic acids. Triazoles are readily prepared by reaction between an azide and an alkyne, optionally in the presence of a copper (Cu) catalyst.

Prostate specific membrane antigen ligands can also be prepared by sequentially adding components to a preformed urea, such as the lysine-urea-glutamate compounds described in Banerjee et al. (J. Med. Chem. vol. 51, pp. 4504-4517, 2008). Other urea-based compounds may also be used as building blocks.

Exemplary syntheses of the near IR, closed chain, sulfo-cyanine dyes used in the presently disclosed compositions are described in U.S. Pat. Nos. 6,887,854 and 6,159,657 and are incorporated herein in their entirety. Additionally, some IR, closed chain, sulfo-cyanine dyes of the presently disclosed subject matter are commercially available, including DyLight™ 800 (ThermoFisher).

As provided hereinabove, the presently disclosed compounds can be synthesized via attachment of near IR, closed (3)

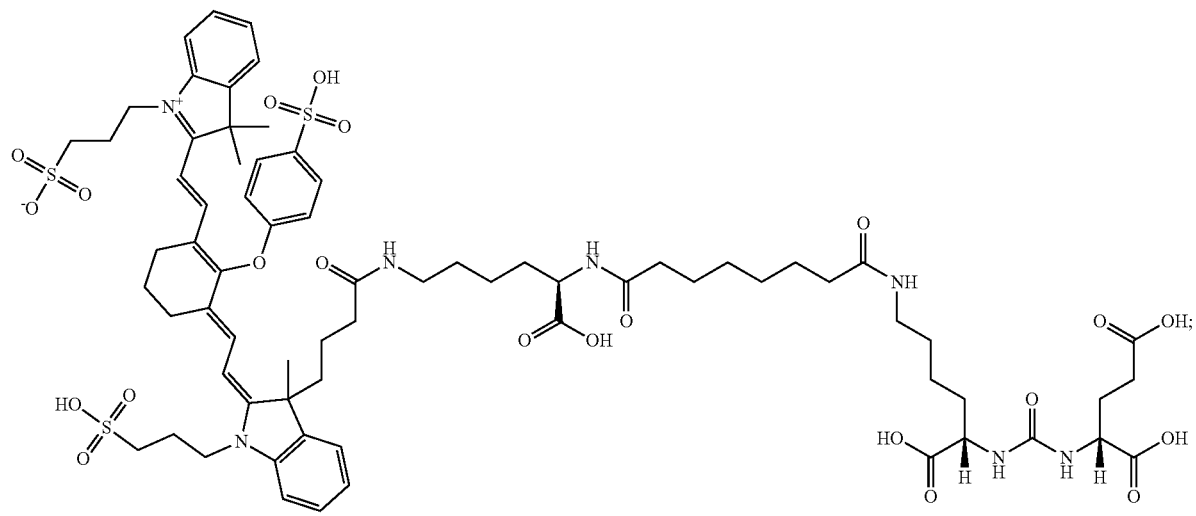

or a pharmaceutically acceptable salt thereof.

The presently disclosed compounds can be made using procedures known in the art by attaching near IR, closed chain, sulfo-cyanine dyes to prostate specific membrane antigen ligands via a linkage. For example, the prostate specific membrane antigen ligands used in the presently disclosed compounds can be synthesized as described in international PCT patent application publication no. WO 2010/108125, to Pomper et al., published Sep. 23, 2010, which is incorporated herein in its entirety. Compounds can assembled by reactions between different components, to form linkages such as ureas (—NRC(O)NR—), thioureas (—NRC(S)NR—), amides (—C(O)NR— or —NRC(O)—), or esters (—C(O)O— or —OC(O)—). Urea linkages can be chain, sulfo-cyanine dyes to prostate specific membrane antigen ligands by reacting a reactive amine on the ligand with a near IR dye. A wide variety of near IR dyes are known in the art, with activated functional groups for reacting with amines.

B. Compositions Comprising Compound (3)

In some embodiments, the presently disclosed subject matter provides a composition comprising a unit dosage form of compound (3), or a pharmaceutically acceptable salt thereof, wherein the composition is adapted for administration to a subject; and wherein, the unit dosage form delivers to the subject an amount between 0.01 mg/kg and 8 mg/kg of compound (3). In some embodiments, the composition unit dosage form delivers to the subject the amount of about 0.01 mg/kg, about 0.05 mg/kg, about 0.10 mg/kg, about 0.20 mg/kg, about 0.30 mg/kg, about 0.35 mg/kg, about 0.40 mg/kg, about 0.45 mg/kg, about 0.50 mg/kg, about 0.55 mg/kg, about 0.60 mg/kg, about 0.65 mg/kg, about 0.70 mg/kg, about 0.75 mg/kg, about 0.80 mg/kg, about 0.90 mg/kg, about 1 mg/kg, about 2 mg/kg, about 4 mg/kg, about 6 mg/kg, or about 8 mg/kg. In some embodiments, the composition is dry and a single dose form.

The term "unit dosage form" as used herein encompasses any measured amount that can suitably be used for administering a pharmaceutical composition to a patient. As recognized by those skilled in the art, when another form (e.g., another salt the pharmaceutical composition) is used in the formulation, the weight can be adjusted to provide an equivalent amount of the pharmaceutical composition.

In some embodiments, the composition is lyophilized in a sterile container. In some embodiments, the composition is contained within a sterile container, wherein the container has a machine detectable identifier that is readable by a medical device.

As used herein, the term "sterile" refers to a system or components of a system free of infectious agents, including, but not limited to, bacteria, viruses, and bioactive RNA or DNA.

As used herein, the term "non-toxic" refers to the non-occurrence of detrimental effects when administered to a vertebrate as a result of using a pharmaceutical composition at levels effective for visualization of tissue under illumination with near-infrared radiation (therapeutic levels).

As used herein, the term "machine detectable identifier" includes identifiers visible or detectable by machines including medical devices. In some instances, the medical device is a telesurgical system. Machine detectable identifiers may facilitate the access or utilization of information that is directly encoded in the machine detectable identifier, or stored elsewhere. Examples of machine detectible identifiers include, but are not limited to, microchips, radio frequency identification (RFID) tags, barcodes (e.g., 1-dimensional or 2-dimensional barcode), data matrices, quick-response (QR) codes, and holograms. One of skill in the art will recognize that other machine detectible identifiers are useful in the presently disclosed subject matter.

In some embodiments, the composition further comprises compound (3) in combination with pharmaceutically acceptable excipients in an oral dosage form. In some embodiments, the composition further comprises compound (3) in combination with pharmaceutically acceptable carriers in an injectable dosage form. In some embodiments, the composition further comprises compound (3) in combination with pharmaceutically acceptable excipients in a dosage form for direct delivery to a surgical site.

"Pharmaceutically acceptable excipient" and "pharmaceutically acceptable carrier" refer to a substance that aids the administration of an active agent to and absorption by a patient and can be included in the presently disclosed compositions without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors and colors, and the like. One of skill in the art will recognize that other pharmaceutical excipients are useful in the presently disclosed subject matter. Pharmaceutically acceptable carriers include but not limited to any adjuvants, excipients, glidants, sweeteners, diluents, preservatives, dyes/colorants, flavoring agents, surfactants, wetting agents, dispersing agents, suspending agents, stabilizing agents, isotonic agents, solvents or emulsors.

The term "oral dosage form" as used herein refers to its normal meaning in the art (i.e., a pharmaceutical composition in the form of a tablet, capsule, caplet, gelcap, geltab, pill and the like).

The term "injectable dosage form" as used herein refers to its normal meaning in the art (i.e., refer to a pharmaceutical composition in the form of solutions, suspensions, and emulsions, for example, water or water/propylene glycol solutions.)

The presently disclosed compositions can be prepared in a wide variety of oral, parenteral and topical dosage forms. Oral preparations include tablets, pills, powder, dragees, capsules, liquids, lozenges, cachets, gels, syrups, slurries, suspensions, etc., suitable for ingestion by the patient. The presently disclosed compositions can also be administered by injection, that is, intravenously, intramuscularly, intracutaneously, subcutaneously, intraduodenally, or intraperitoneally. Also, the compositions described herein can be administered by inhalation, for example, intranasally. Additionally, the presently disclosed compositions can be administered transdermally. The compositions of this invention can also be administered by intraocular, insufflation, powders, and aerosol formulations (for examples of steroid inhalants, see Rohatagi, J. Clin. Pharmacol. 35:1187-1193, 1995; Tjwa, Ann. Allergy Asthma Immunol. 75:107-111, 1995). Accordingly, the presently disclosed subject matter also provides pharmaceutical compositions including a pharmaceutically acceptable carrier or excipient.

For preparing pharmaceutical compositions from the presently disclosed subject matter, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material. Details on techniques for formulation and administration are well described in the scientific and patent literature, see, e.g., the latest edition of Remington's Pharmaceutical Sciences, Maack Publishing Co, Easton Pa. ("Remington's").

In powders, the carrier is a finely divided solid, which is in a mixture with the finely divided active component. In tablets, the active component is mixed with the carrier having the necessary binding properties in suitable proportions and compacted in the shape and size desired. The powders and tablets preferably contain from 5% or 10% to 70% of the compounds of the presently disclosed subject matter.

Suitable solid excipients include, but are not limited to, magnesium carbonate; magnesium stearate; talc; pectin; dextrin; starch; tragacanth; a low melting wax; cocoa butter; carbohydrates; sugars including, but not limited to, lactose, sucrose, mannitol, or sorbitol, starch from corn, wheat, rice, potato, or other plants; cellulose such as methyl cellulose, hydroxypropylmethyl-cellulose, or sodium carboxymethyl-cellulose; and gums including arabic and tragacanth; as well as proteins including, but not limited to, gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage). Pharmaceutical compositions of the invention can also be used orally using, for example, push-fit capsules made of gelatin, as well as soft, sealed capsules made of gelatin and a coating such as glycerol or sorbitol. Push-fit capsules can contain the presently disclosed compositions mixed with a filler or binders such as lactose or starches, lubricants such as talc or magnesium stearate, and, optionally, stabilizers. In soft capsules, the presently disclosed compositions may be dissolved or suspended in suitable liquids, such as fatty oils, liquid paraffin, or liquid polyethylene glycol with or without stabilizers.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the presently disclosed compositions in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

Oil suspensions can be formulated by suspending the presently disclosed compositions in a vegetable oil, such as arachis oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, J. Pharmacol. Exp. Ther. 281:93-102, 1997. The pharmaceutical formulations of the invention can also be in the form of oil-in-water emulsions. The oily phase can be a vegetable oil or a mineral oil, described above, or a mixture of these.

Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

The presently disclosed compositions can also be delivered as microspheres for slow release in the body. For example, microspheres can be formulated for administration via intradermal injection of drug-containing microspheres, which slowly release subcutaneously (see Rao, J. Biomater Sci. Polym. Ed. 7:623-645, 1995; as biodegradable and injectable gel formulations (see, e.g., Gao Pharm. Res. 12:857-863, 1995); or, as microspheres for oral administration (see, e.g., Eyles, J. Pharm. Pharmacol. 49:669-674, 1997). Both transdermal and intradermal routes afford constant delivery for weeks or months.

In another embodiment, the presently disclosed compositions can be formulated for parenteral administration, such as intravenous (IV) administration or administration into a body cavity or lumen of an organ. The formulations for administration will commonly comprise a solution of the presently disclosed compositions dissolved in a pharmaceutically acceptable carrier. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well-known techniques including radiation, chemical, heat/pressure, and filtration sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of the presently disclosed compositions in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a non-toxic parenterally-acceptable diluent or solvent, such as a solution of 1,3-butanediol.

In another embodiment, the formulations of the presently disclosed compositions can be delivered by the use of liposomes which fuse with the cellular membrane or are endocytosed, i.e., by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the presently disclosed compositions into the target cells in vivo. (See, e.g., Al-Muhammed, J. Microencapsul. 13:293-306, 1996; Chonn, Curr. Opin. Biotechnol. 6:698-708, 1995; Ostro, Am. J. Hosp. Pharm. 46:1576-1587, 1989).

Lipid-based drug delivery systems include lipid solutions, lipid emulsions, lipid dispersions, self-emulsifying drug delivery systems (SEDDS) and self-microemulsifying drug delivery systems (SMEDDS). In particular, SEDDS and SMEDDS are isotropic mixtures of lipids, surfactants and co-surfactants that can disperse spontaneously in aqueous media and form fine emulsions (SEDDS) or microemulsions (SMEDDS). Lipids useful in the formulations of the presently disclosed subject matter include any natural or synthetic lipids including, but not limited to, sesame seed oil, olive oil, castor oil, peanut oil, fatty acid esters, glycerol esters, Labrafil®, Labrasol®, Cremophor®, Solutol®, Tween®, Capryol®, Capmul®, Captex®, and Peceol®.

In some embodiments the presently disclosed compositions are sterile and generally free of undesirable matter. The compounds and compositions may be sterilized by conventional, well known techniques including heat/pressure, gas plasma, steam, radiation, chemical, and filtration sterilization techniques.

For example, terminal heat sterilization can be used to destroy all viable microorganisms within the final formulation. An autoclave is commonly used to accomplish terminal heat-sterilization of drug products in their final packaging. Typical autoclave cycles in the pharmaceutical industry to achieve terminal sterilization of the final product are 121° C. for 15 minutes. The presently disclosed compositions can be autoclaved at a temperature ranging from 115 to 130° C. for a period of time ranging from 5 to 40 minutes with acceptable stability. Autoclaving is preferably carried out in the temperature range of 119 to 122° C. for a period of time ranging from 10 to 36 minutes.

The compositions can also be sterilized by dry heat as described by Karlsson, et al., in U.S. Pat. No. 6,392,036, which discloses a method for the dry heat sterilization that can be used for drug formulations. The compositions can also be sterilized as described in WO 02/41925 to Breath Limited, which discloses a rapid method, similar to pasteurization, for the sterilization of compositions. This method entails pumping the composition to be sterilized through stainless steel pipes and rapidly raising the temperature of the composition to about 130-145° C. for about 2-20 seconds, subsequently followed by rapid cooling in seconds to ambient conditions.

The compositions can also be sterilized by irradiation as described by Illum and Moeller in *Arch. Pharm. Chem. Sci.*, Ed. 2, 1974, pp. 167-174). The compositions can also be sterilized by UV, x-rays, gamma rays, e beam radiation, flaming, baking, and chemical sterilization.

Alternatively, sterile pharmaceutical compositions according to the presently disclosed subject matter may be prepared using aseptic processing techniques. Aseptic filling is ordinarily used to prepare drug products that will not withstand heat sterilization, but in which all of the ingredients are sterile. Sterility is maintained by using sterile materials and a controlled working environment. All containers and apparatus are sterilized, preferably by heat sterilization, prior to filling. The container (e.g., vial, ampoule, infusion bag, bottle, or syringe) are then filled under aseptic conditions.

In some embodiments, the compounds and presently disclosed compositions are non-toxic and generally free of detrimental effects when administered to a vertebrate at levels effective for visualization of tissue under illumination with near-infrared radiation. Toxicity of the compounds and presently disclosed compositions can be assessed by measuring their effects on a target (organism, organ, tissue or cell). Because individual targets typically have different levels of response to the same dose of a compound, a population-level measure of toxicity is often used which relates the probabilities of an outcome for a given individual in a population. Toxicology of compounds can be determined by conventional, well-known techniques including in vitro (outside of a living organism) and in vivo (inside of a living organism) studies.

For example, determination of metabolic stability is commonly examined when assessing the toxicity of a compound as it is one of several major determinates in defining the oral bioavailability and systemic clearance of a compound. After a compound is administered orally, it first encounters metabolic enzymes in the gastrointestinal lumen as well as in the intestinal epithelium. After it is absorbed into the bloodstream through the intestinal epithelium, it is first delivered to the liver via the portal vein. A compound can be effectively cleared by intestinal or hepatic metabolism before it reaches systemic circulation, a process known as first pass metabolism. The stability of a compound towards metabolism within the liver as well as extrahepatic tissues will ultimately determine the concentration of the compound found in the systemic circulation and affect its half-life and residence time within the body. Cytochrome P450 (CYP) enzymes are found primarily in the liver but also in the intestinal wall, lungs, kidneys and other extrahepatic organs and are the major enzymes involved in compound metabolism. Many compounds undergo deactivation by CYPs, either directly or by facilitated excretion from the body. Also, many compounds are bioactivated by CYPs to form their active compounds. Thus, determining the reactivity of a compound to CYP enzymes is commonly used to assess metabolic stability of a compound.

The Ames reverse mutation Assay is another common toxicology assay for assessing the toxicity of a compound. The Ames Assay, utilizes several different tester strains, each with a distinct mutation in one of the genes comprising the histidine (his) biosynthetic operon (Ames, B. N., et al., (1975) Mutation Res. 31:347-363). The detection of revertant (i.e., mutant) bacteria in test samples that are capable of growth in the absence of histidine indicates that the compound under evaluation is characterized by genotoxic (i.e. mutagenic) activity. The Ames Assay is capable of detecting several different types of mutations (genetic damage) that may occur in one or more of the tester strains. The practice of using an in vitro bacterial assay to evaluate the genotoxic activity of drug candidates is based on the prediction that a substance that is mutagenic in a bacterium is likely to be carcinogenic in laboratory animals, and by extension may be carcinogenic or mutagenic to humans.

In addition, the human ether-a-go-go related gene (hERG) assay can be used to evaluate the potential cardiotoxicity of a compound. Cardiotoxicity can arise when the QT interval is prolonged leading to an elevated risk of life-threatening arrhythmias. The QT interval is a measure of the time between the start of the Q wave and the end of the T wave in the heart's electrical cycle. The QT interval represents electrical depolarization and repolarization of the ventricles. A lengthened QT interval has most commonly been associated with loss of current through hERG potassium ion channels due to direct block of the ion channel by drugs or by inhibition of the plasma membrane expression of the channel protein (Su et al. J. Biomol Screen 2011, 16, 101-111). Thus, an in vitro hERG screening assay can be used to detect disruption or inhibition of the hERG membrane trafficking function and assess potential cardiotoxicity of a compound.

Other methods of assessing the toxicity of compounds include in vivo studies which administer relatively large doses of a test compound to a group of animals to determine the level which is lethal to a percentage of the population (mean lethal dose $LD_{50}$ or mean lethal concentration $LC_{50}$). Toxicity of a compound can also be assessed in vivo by examining whether a compound produces statistically significant negative effects on cardiac, blood pressure, central nervous system (CNS), body weight, food intake, gross or microscopic pathology, clinical pathology, or respiratory measures in an animal.

In some embodiments, the presently disclosed compositions can be lyophilized in a sterile container for convenient dry storage and transport. A ready-to-use preparation can subsequently be made by reconstituting the lyophilized compositions with sterile water. The terms "lyophilization," "lyophilized," and "freeze-dried" refer to a process by which the material to be dried is first frozen and then the ice or frozen solvent is removed by sublimation in a vacuum environment. An excipient may be included in pre-lyophilized formulations to enhance stability of the lyophilized product upon storage.

In some embodiments, the composition can be contained within a sterile container, where the container has a machine detectable identifier which is readable by a medical device. Examples of machine detectible identifiers include microchips, radio frequency identification (RFID) tags, barcodes (e.g., 1-dimensional or 2-dimensional barcode), data matrices, quick-response (QR) codes, and holograms. One of skill in the art will recognize that other machine detectible identifiers are useful in the presently disclosed subject matter.

In some embodiments, the machine detectable identifier can include a microchip, an integrated circuit (IC) chip, or an electronic signal from a microchip that is detectable and/or readable by a computer system that is in communication with the medical device. In some embodiments, the machine detectable identifier includes a radio frequency identification (RFID) tag. RFID tags are sometimes called as transponders. RFID tags generally are devices formed of an IC chip, an antenna, an adhesive material, and are used for transmitting or receiving predetermined data with an external reader or interrogator. RFID tags can transmit or receive data with a reader by using a contactless method. According to the amplitude of a used frequency, inductive coupling, backscattering, and surface acoustic wave (SAW) may be used. Using electromagnetic waves, data may be transmitted or received to or from a reader by using a full duplex method, a half duplex (HDX) method, or a sequential (SEQ) method.

In some embodiments, the machine detectable identifier can include a barcode. Barcodes include any machine-readable format, including one-dimensional and two-dimensional formats. One-dimensional formats include, for example, Universal Product Code (UPC) and Reduced Space Symbology (RSS). Two-dimensional formats, or machine-readable matrices, include for example, Quick Response (QR) Code and Data Matrix.

In some embodiments, the medical device can be configured to detect the machine detectable identifier. In one example, the medical device is a tele-surgical system that includes a special imaging mode (e.g., a fluorescence imaging mode) for use with dyes such as those described in this disclosure. One example of a tele-surgical system that includes a fluorescence imaging mode is described in U.S. Pat. No. 8,169,468, entitled "Augmented Stereoscopic Visualization for a Surgical Robot," which is hereby incorporated in its entirety herein. In some embodiments, medical devices can incorporate an imaging device that can scan, read, view, or otherwise detect a machine detectable identifier that is displayed to the imaging device. In one aspect, the medical device will permit a user to access the fluorescence imaging mode of the medical device only if the medical device detects the presence of a known machine detectable identifier that corresponds to a dye identified as being compatible for use with the medical device. In contrast, if the medical device does not detect a known machine detectable identifier, the medical device will not permit a user to access the fluorescence imaging mode and associated functionality. Imaging devices can include optical scanners, barcode readers, cameras, and imaging devices contained within a tele-surgical system such as an endoscope. Information associated with the machine detectable identifier can then be retrieved by the medical device using an imaging device. Upon detection of the identifier, an automatic process may be launched to cause a predetermined action to occur, or certain data to be retrieved or accessed. The information encoded onto the machine detectable identifier may include instructions for triggering an action, such as administering a composition of the presently disclosed subject matter to a patient. In some embodiments, the machine detectable identifier includes unencrypted e-pedigree information in the desired format. The e-pedigree information can include, for example, lot, potency, expiration, national drug code, electronic product code, manufacturer, distributor, wholesaler, pharmacy and/or a unique identifier of the salable unit.

In some embodiments, the sterile container having a machine detectable identifier includes a fluid outlet configured to mate with the medical device. In some embodiments, the fluid outlet of the machine detectable identifier is mechanically affixed to the medical device.

C. Methods of Imaging Using Compositions Comprising Compound (3)

In some embodiments, the presently disclosed subject matter provides a use of the composition comprising compound (3), or a pharmaceutically acceptable salt thereof, adapted for administration to a subject, e.g., a patient, to obtain visualization of tissue expressing PSMA under illumination with near-infrared radiation, wherein the unit dosage form delivers to the subject an amount between about 0.01 mg/kg and 8 mg/kg of compound (3). In some embodiments, the use is adapted for administration to a human patient to obtain visualization of human tissue under illumination with near-infrared radiation wherein the unit dosage form delivers to the human patient an amount between about 0.01 mg/kg and 8 mg/kg of a compound (3).

The compounds and presently disclosed compositions can be delivered by any suitable means, including oral, parenteral and topical methods. Transdermal administration methods, by a topical route, can be formulated as applicator sticks, solutions, suspensions, emulsions, gels, creams, ointments, pastes, jellies, paints, powders, and aerosol.

The pharmaceutical preparation is preferably in unit dosage form. In such form the preparation is subdivided into unit doses containing appropriate quantities of the compounds and presently disclosed compositions. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

In some embodiments, co-administration can be accomplished by co-formulation, i.e., preparing a single pharmaceutical composition including the compounds and presently disclosed compositions and any other agent. Alternatively, the various components can be formulated separately.

ing PSMA, the method comprising, administering to a subject, e.g., a patient, a composition comprising compound (3), described herein. In some embodiments, the method comprises, administering to a subject a composition comprising compound (3):

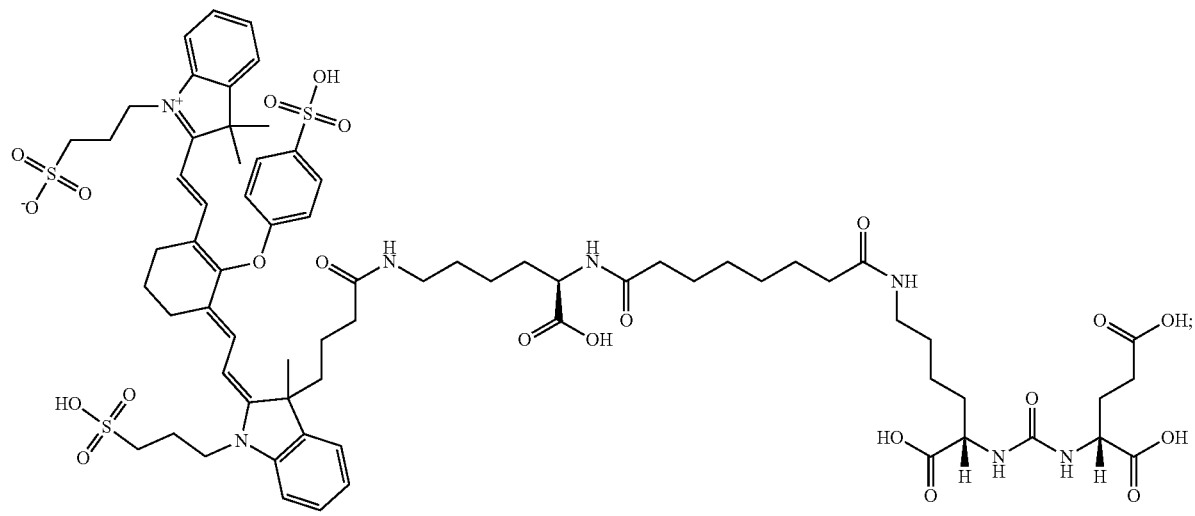

(3)

30 or a pharmaceutically acceptable salt thereof.

The presently disclosed compositions, and any other agents, can be present in any suitable amount, and can depend on various factors including, but not limited to, weight and age of the patient, state of the disease, etc. Suitable dosage ranges include from about 0.01 and 8 mg/kg, or about 0.01 and 5 mg/kg, or about 0.01 and 1 mg/kg. Suitable dosage ranges also include 0.01, 0.05, 0.10, 0.20, 0.30, 0.35, 0.40, 0.45, 0.50, 0.55, 0.60, 0.65, 0.70, 0.75, 0.80, 0.90, 1, 2, 4, 6, or 8 mg/kg.

The composition can also contain other compatible compositions. The compositions described herein can be used in combination with one another, with other active compositions known to be useful for visualization of tissue under illumination with near-infrared radiation, or with compositions that may not be effective alone, but may contribute to the efficacy of the active composition.

As used herein, the term "visualization" refers to methods of obtaining graphic images of tissue by any means, including illumination with near-infrared radiation.

The term "near-infrared radiation" or "near IR radiation" or "NIR" radiation refers to optical radiation with a wavelength in the range of about 700 nm to about 1400 nm. References herein to the optionally plural term "wavelength(s)" indicates that the radiation may be a single wavelength or a spectrum of radiation having differing wavelengths.

The term "tissue" as used herein includes, but is not limited to, allogenic or xenogenic bone, neural tissue, fibrous connective tissue including tendons and ligaments, cartilage, dura, fascia, pericardia, muscle, heart valves, veins and arteries and other vessels, dermis, adipose tissue, glandular tissue, prostate tissue, kidney tissue, brain tissue, renal tissue, bladder tissue, lung tissue, breast tissue, pancreatic tissue, vascular tissue, tumor tissue, cancerous tissue, or prostate tumor tissue.

In particular embodiments, the presently disclosed subject matter provides a method for visualization of tissue express- In some embodiments, the method administers to a subject a pharmaceutical composition comprising a unit dosage form of compound (3), wherein the composition is sterile, non-toxic, and adapted for administration to a subject; and wherein, the unit dosage form delivers to the subject an amount between about 0.01 mg/kg and 8 mg/kg of compound (3). In some embodiments, the method further comprises obtaining the image during administration, after administration, or both during and after administration of the composition. In some embodiments, the method further comprises intravenously injecting a composition comprising compound (3) into a subject. In some embodiments, the composition is injected into a circulatory system of the subject.

In some embodiments, the method further comprises visualizing a subject area on which surgery is or will be performed, or for viewing a subject area otherwise being examined by a medical professional. In some embodiments, the method further comprises performing a surgical procedure on the subject areas based on the visualization of the surgical area. In some embodiments, the method further comprises viewing a subject area on which an ophthalmic, arthroscopic, laparoscopic, cardiothoracic, muscular, or neurological procedure is or will be performed. In some embodiments, the method further comprises obtaining ex vivo images of at least a portion of the subject.

In some embodiments, the tissue being visualized is tumor tissue. In some embodiments, the tissue being visualized is dysplastic or cancerous tissue. In some embodiments, the tissue being visualized is prostate tissue. In some embodiments, the tissue being visualized is prostate tumor tissue.

In other embodiments, the one or more PSMA-expressing tumor or cell is selected from the group consisting of: a prostate tumor or cell, a metastasized prostate tumor or cell, a lung tumor or cell, a renal tumor or cell, a glioblastoma, a pancreatic tumor or cell, a bladder tumor or cell, a sarcoma, a melanoma, a breast tumor or cell, a colon tumor or cell, a germ cell, a pheochromocytoma, an esophageal tumor or cell, a stomach tumor or cell, and combinations thereof. In more particular embodiments, the one or more PSMA-expressing tumor or cell is a prostate tumor or cell. In certain embodiments, the one or more PSMA-expressing tumors or cells are in vitro, in vivo, or ex vivo. In particular embodiments, the one or more PSMA-expressing tumors or cells are present in a subject.

The "subject" treated by the presently disclosed methods in their many embodiments is desirably a human subject, although it is to be understood that the methods described herein are effective with respect to all vertebrate species, which are intended to be included in the term "subject." Accordingly, a "subject" can include a human subject for medical purposes, such as for the treatment of an existing condition or disease or the prophylactic treatment for preventing the onset of a condition or disease, or an animal subject for medical, veterinary purposes, or developmental purposes. Suitable animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a condition or disease. Thus, the terms "subject" and "patient" are used interchangeably herein. The term "subject" also refers to an organism, tissue, cell, or collection of cells from a subject.

In general, the "effective amount" of an active agent refers to the amount necessary to elicit the desired biological response. As will be appreciated by those of ordinary skill in this art, the effective amount of an agent or device may vary depending on such factors as the desired biological endpoint, the agent to be delivered, the makeup of the pharmaceutical composition, the target tissue, and the like.

In some embodiments, compound (3) is cleared from the subject's kidneys in about 24 hours.

In some embodiments, the presently disclosed methods use compounds that are stable in vivo such that substantially all, e.g., more than about 50%, 60%, 70%, 80%, or more preferably 90% of the injected compound is not metabolized by the body prior to excretion. In other embodiments, the compound comprising the imaging agent is stable in vivo.

C. PSMA-Targeting Compounds and Uses Thereof

In further embodiments, the presently disclosed subject matter provides a compound having the structure:

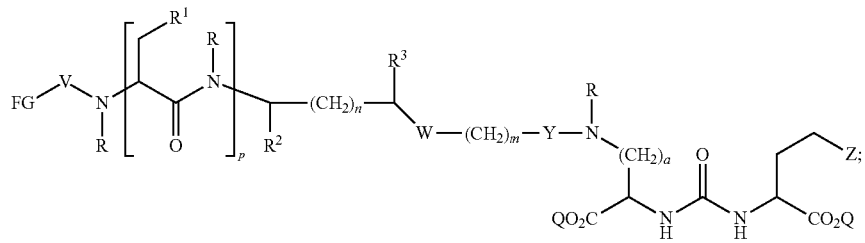

wherein: Z is tetrazole or $CO_2Q$; each Q is independently selected from hydrogen or a protecting group; FG is a fluorescent dye moiety which emits in the visible or near infrared spectrum; each R is independently H or $C_1$-$C_4$ alkyl; V is —C(O)—; W is —NRC(O); Y is —C(O); a is 1, 2, 3, or 4; m is 1, 2, 3, 4, 5, or 6; n is 1, 2, 3, 4, 5 or 6; p is 0, 1, 2, or 3, and when p is 2 or 3, each $R^1$ may be the same or different; $R^1$ is H, $C_1$-$C_6$ alkyl, $C_6$-$C_{12}$ aryl, or alkylaryl having 1 to 3 separate or fused rings and from 6 to about 18 ring carbon atoms; $R^2$ and $R^3$ are independently H, $CO_2H$, or $CO_2R^4$, where $R^4$ is a $C_1$-$C_6$ alkyl, $C_6$-$C_{12}$ aryl, or alkylaryl having 1 to 3 separate or fused rings and from 6 to about 18 ring carbon atoms, wherein when one of $R^2$ and $R^3$ is $CO_2H$ or $CO_2R^4$, the other is H.

As used herein, a "protecting group" is a chemical substituent which can be selectively removed by readily available reagents which do not attack the regenerated functional group or other functional groups in the molecule. Suitable protecting groups are known in the art and continue to be developed. Suitable protecting groups may be found, for example in Wutz et al. ("Greene's Protective Groups in Organic Synthesis, Fourth Edition," Wiley-Interscience, 2007). Protecting groups for protection of the carboxyl group, as described by Wutz et al. (pages 533-643), are used in certain embodiments. In some embodiments, the protecting group is removable by treatment with acid. Specific examples of protecting groups include but are not limited to, benzyl, p-methoxybenzyl (PMB), tertiary butyl (t-Bu), methoxymethyl (MOM), methoxyethoxymethyl (MEM), methylthiomethyl (MTM), tetrahydropyranyl (THP), tetrahydrofuranyl (THF), benzyloxymethyl (BOM), trimethylsilyl (TMS), triethylsilyl (TES), t-butyldimethylsilyl (TBDMS), and triphenylmethyl (trityl, Tr). Persons skilled in the art will recognize appropriate situations in which protecting groups are required and will be able to select an appropriate protecting group for use in a particular circumstance.

In certain embodiments, the compound has the following structure:

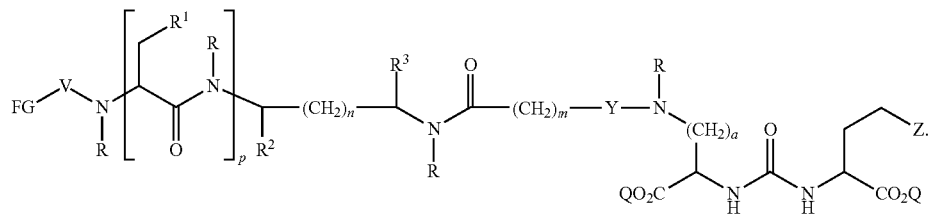

In more certain embodiments, the compound has the following structure:

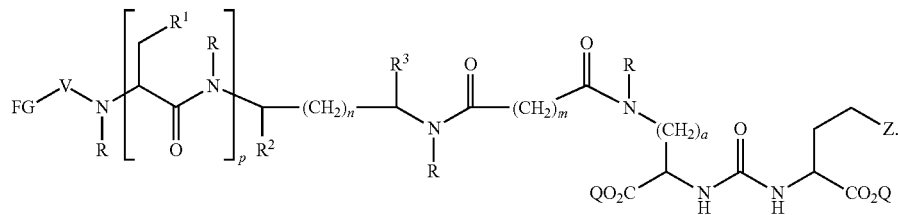

In yet more certain embodiments, the compound has the following structure:

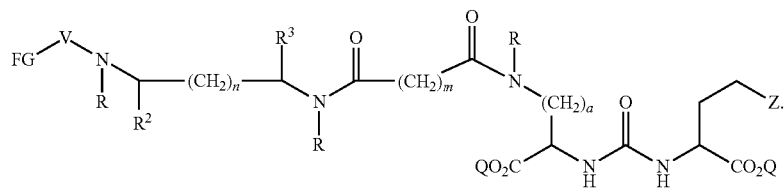

In particular embodiments, $R^3$ is $CO_2H$ and $R^2$ is H or $R^2$ is $CO_2H$ and $R^3$ is H. In other embodiments, $R^2$ is $CO_2R^4$ and $R^3$ is H or $R^3$ is $CO_2R^4$, and $R^2$ is H. In yet other embodiments, $R^2$ is H, and $R^3$ is H.

In certain embodiments, $R^4$ is $C_6$-$C_{12}$ aryl, or alkylaryl having 1 to 3 separate or fused rings and from 6 to about 18 ring carbon atoms. In certain embodiments, $R^1$ is $C_6$-$C_{12}$ aryl. In more certain embodiments, $R^1$ is phenyl.

In particular embodiments, FG is a fluorescent dye moiety which emits in the near infrared spectrum. In more particular embodiments, FG comprises a fluorescent dye moiety selected from the group consisting of carbocyanine, indocarbocyanine, oxacarbocyanine, thiacarbocyanine and merocyanine, polymethine, coumarine, rhodamine, xanthene, fluorescein, boron-dipyrromethane (BODIPY), Cy5, Cy5.5, Cy7, VivoTag-680, VivoTag-S680, VivoTag-S750, AlexaFluor660, AlexaFluor680, AlexaFluor700, AlexaFluor750, AlexaFluor790, Dy677, Dy676, Dy682, Dy752, Dy780, DyLight547, Dylight647, HiLyte Fluor 647, HiLyte Fluor 680, HiLyte Fluor 750, IRDye 800CW, IRDye 800RS, IRDye 700DX, ADS780WS, ADS830WS, and ADS832WS. In yet more particular embodiments, FG has a structure selected from the group consisting of:

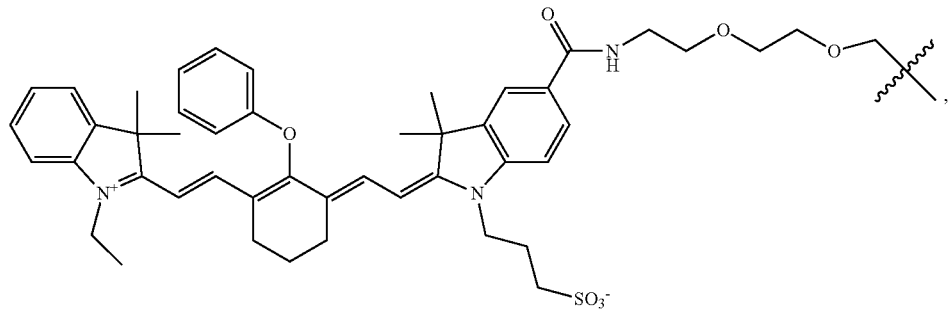

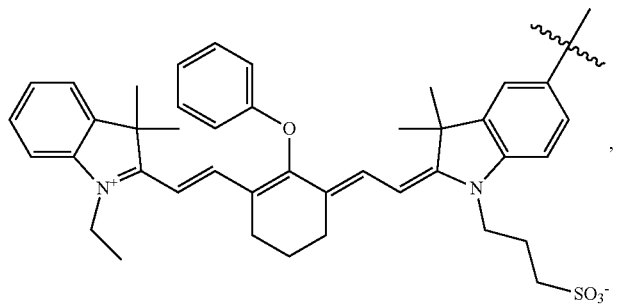
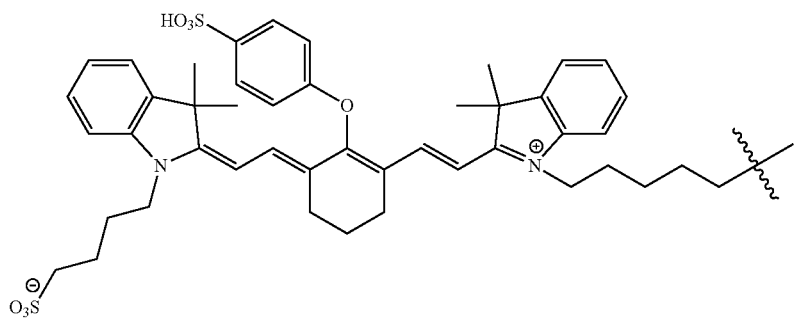
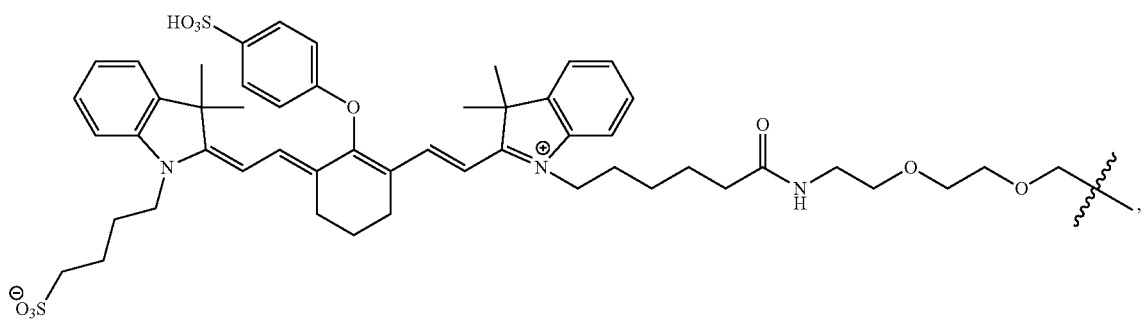
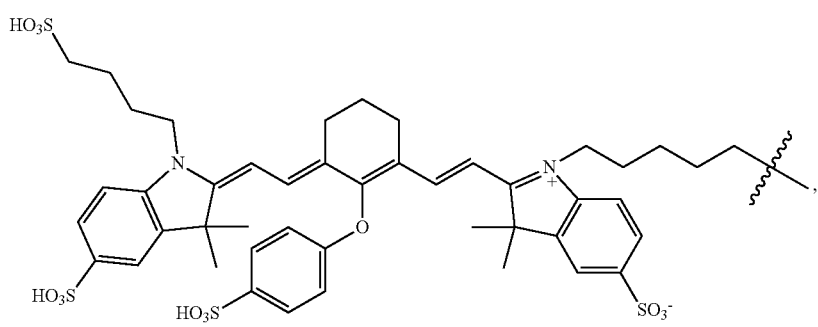
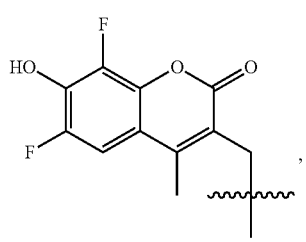

-continued
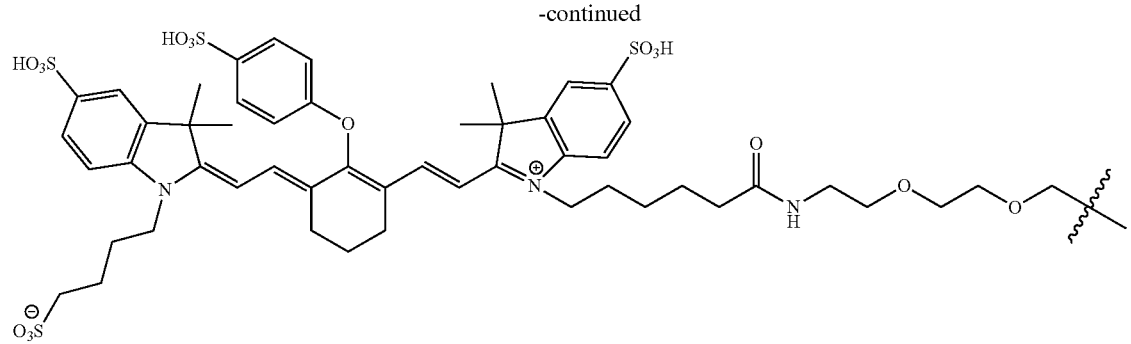
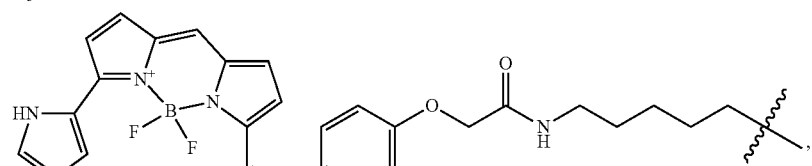
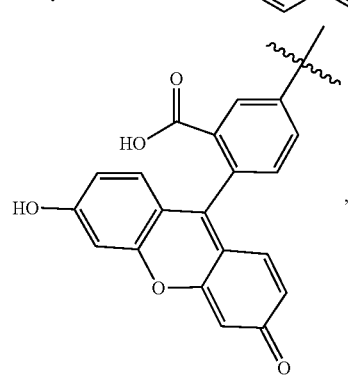
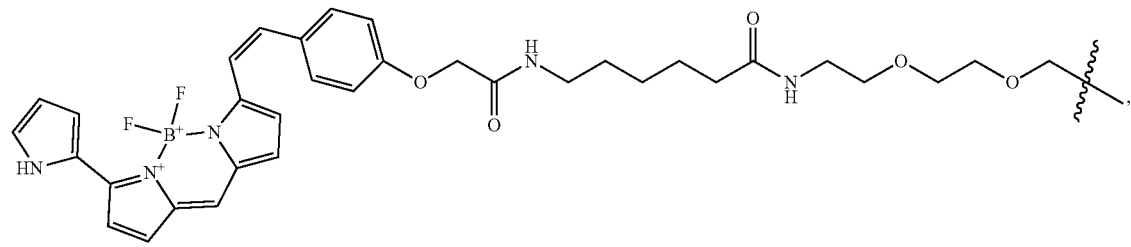
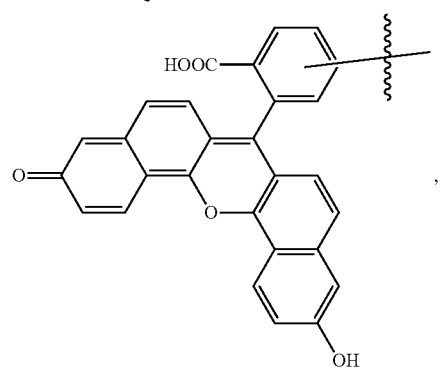
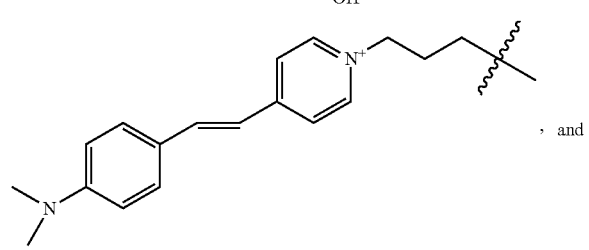
, and

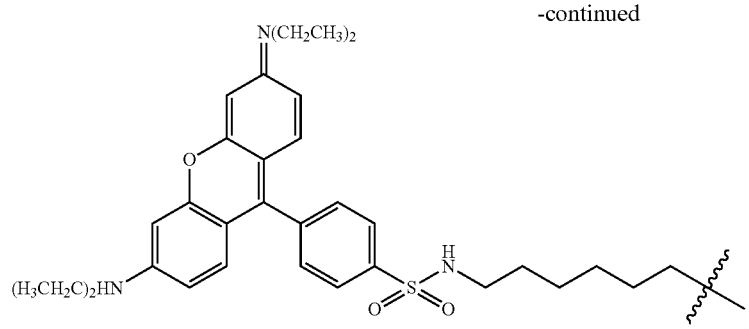
In some embodiments, the compound is selected from the group consisting of:
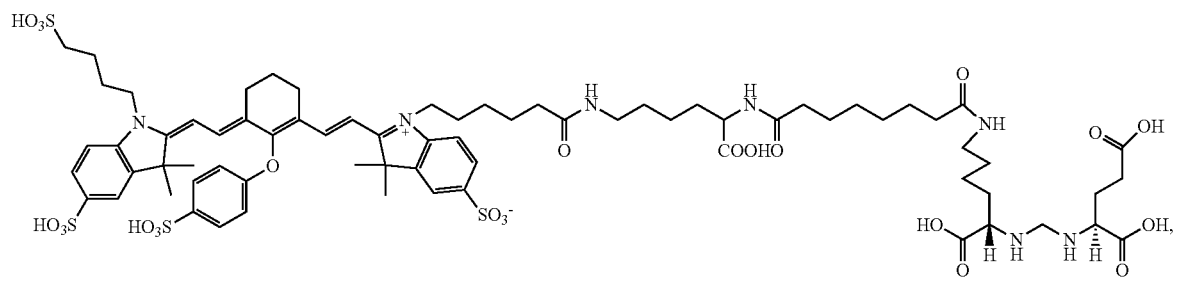
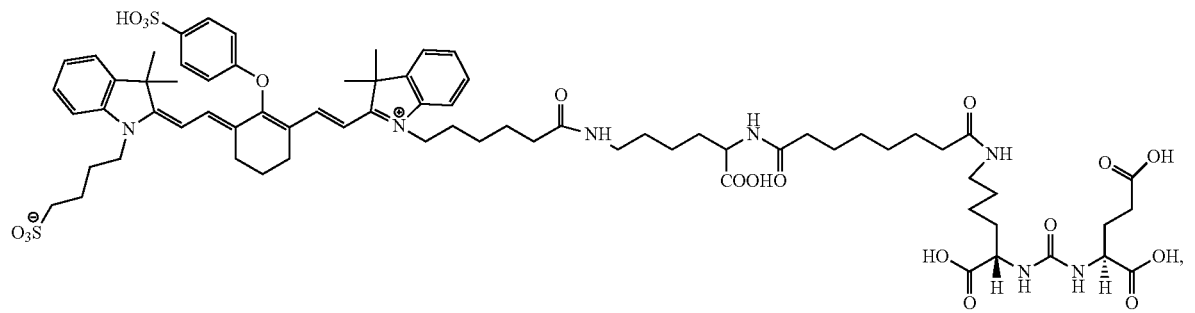
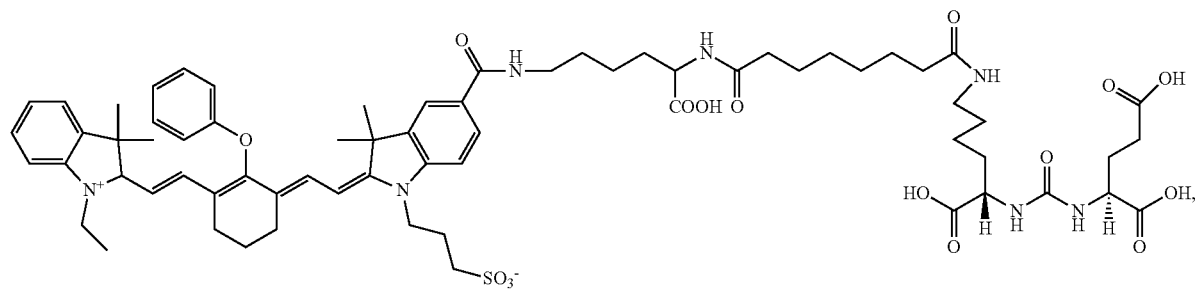
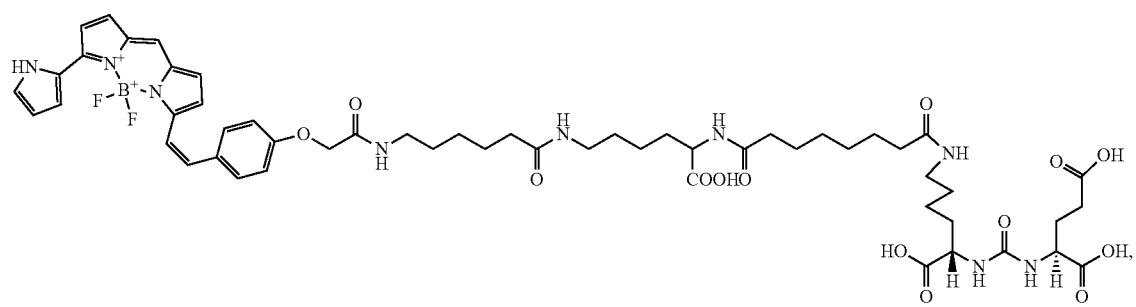

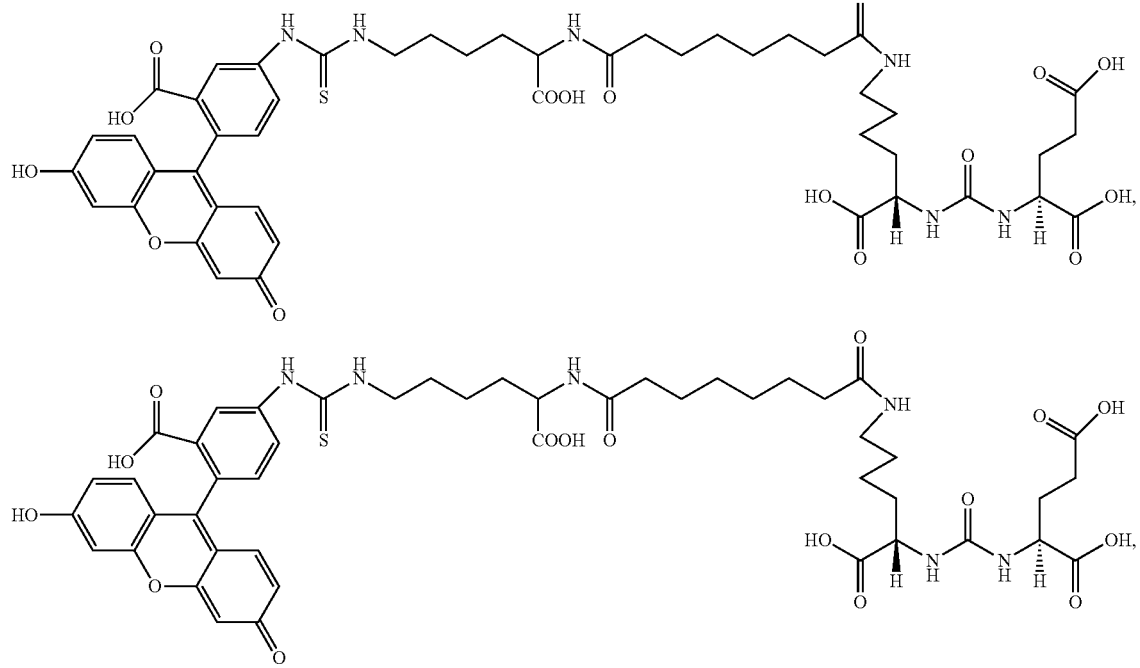

-continued

Imaging

Embodiments include methods of imaging one or more cells, organs or tissues comprising exposing cells to or administering to a subject an effective amount of a compound with an isotopic label suitable for imaging. In some embodiments, the one or more organs or tissues include prostate tissue, kidney tissue, brain tissue, vascular tissue or tumor tissue. The cells, organs or tissues may be imaged while within an organism, either by whole body imaging or intraoperative imaging, or may be excised from the organism for imaging.

In another embodiment, the imaging method is suitable for imaging studies of PSMA inhibitors, for example, by studying competitive binding of non-radiolabeled inhibitors. In still another embodiment, the imaging method is suitable for imaging of cancer, tumor or neoplasm. In a further embodiment, the cancer is selected from eye or ocular cancer, rectal cancer, colon cancer, cervical cancer, prostate cancer, breast cancer and bladder cancer, oral cancer, benign and malignant tumors, stomach cancer, liver cancer, pancreatic cancer, lung cancer, corpus uteri, ovary cancer, prostate cancer, testicular cancer, renal cancer, brain cancer (e.g., gliomas), throat cancer, skin melanoma, acute lymphocytic leukemia, acute myelogenous leukemia, Ewing's Sarcoma, Kaposi's Sarcoma, basal cell carcinoma and squamous cell carcinoma, small cell lung cancer, choriocarcinoma, rhabdomyosarcoma, angiosarcoma, hemangioendothelioma, Wilms Tumor, neuroblastoma, mouth/pharynx cancer, esophageal cancer, larynx cancer, lymphoma, neurofibromatosis, tuberous sclerosis, hemangiomas, and lymphangiogenesis.

The imaging methods of the invention are suitable for imaging any physiological process or feature in which PSMA is involved. Typically, imaging methods are suitable for identification of areas of tissues or targets which express high concentrations of PSMA. Typical applications include imaging glutamateric neurotransmission, presynaptic glutamatergic neurotransmission, malignant tumors or cancers that express PSMA, prostate cancer (including metastasized prostate cancer), and angiogenesis. Essentially all solid tumors express PSMA in the neovasculture. Therefore, methods of the present invention can be used to image nearly all solid tumors including lung, renal cell, glioblastoma, pancreas, bladder, sarcoma, melanoma, breast, colon, germ cell, pheochromocytoma, esophageal and stomach. Also, certain benign lesions and tissues including endometrium, schwannoma and Barrett's esophagus can be imaged according to the present invention.

The methods of imaging angiogenesis are suitable for use in imaging a variety of diseases and disorders in which angiogenesis takes place. Illustrative, non-limiting, examples include tumors, collagen vascular disease, cancer, stroke, vascular malformations, and retinopathy. Methods of imaging angiogenesis are also suitable for use in diagnosis and observation of normal tissue development.

PSMA is frequently expressed in endothelial cells of capillary vessels in peritumoral and endotumoral areas of various malignancies such that compounds of the invention and methods of imaging using same are suitable for imaging such malignancies.

Imaging agents of the invention may be used in accordance with the methods of the invention by one of skill in the art. Images can be generated by virtue of differences in the spatial distribution of the imaging agents which accumulate at a site when contacted with PSMA. The spatial distribution may be measured using any means suitable for the particular label, for example, a fluorescence camera and the like.

In general, a detectably effective amount of the imaging agent is administered to a subject. As used herein, "a detectably effective amount" of the imaging agent is defined as an amount sufficient to yield an acceptable image using equipment which is available for clinical use. A detectably effective amount of the imaging agent may be administered in more than one injection. The detectably effective amount of the imaging agent can vary according to factors such as the degree of susceptibility of the individual, the age, sex, and weight of the individual, idiosyncratic responses of the individual, and the dosimetry. Detectably effective amounts of the imaging agent can also vary according to instrument and film-related factors. Optimization of such factors is well within the level of skill in the art. The amount of imaging agent used for diagnostic purposes and the duration of the imaging study will depend upon the radionuclide used to label the agent, the body mass of the patient, the nature and severity of the condition being treated, the nature of therapeutic treatments which the patient has undergone, and on the idiosyncratic responses of the patient. Ultimately, the attending physician will decide the amount of imaging agent to administer to each individual patient and the duration of the imaging study.

In some embodiments, the compounds are excreted from tissues of the body quickly. Generally, the compounds are excreted from tissues of the body slowly enough to allow sufficient time for imaging or other use. Typically compounds of the invention are eliminated from the body in less than about 24 hours. More typically, compounds of the invention are eliminated from the body in less than about 16 hours, 12 hours, 8 hours, 6 hours, 4 hours, 2 hours, 90 minutes, or 60 minutes. Exemplary compounds are eliminated in between about 60 minutes and about 120 minutes.

In some embodiments of the invention, the compounds are designed to increase uptake in PSMA positive cells (i.e., tumor cells). For example, highly hydrophilic compounds may be excreted quickly. Compounds with increased hydrophobicity, such as compounds having hydrophobic linkers, may have longer circulation times, thereby providing more prolonged supply of tracer to bind to cells. According to embodiments of compounds according to the invention, hydrophobicity can be increased when, for example, p is 1 or more, or when $R^2$ or $R^3$ is $CO_2R^4$.

Accordingly, in some embodiments, the presently disclosed subject matter provides a method of imaging one or more cells, organs or tissues by exposing the cell to or administering to an organism an effective amount of a presently disclosed compound, where the compound includes a fluorescent dye moiety suitable for imaging.

Cell Sorting

Embodiments include methods for sorting cells by exposing the cells to a compound discussed above, where the compound includes a fluorescent dye moiety, followed by separating cells which bind the compound from cells which do not bind the compound.

Fluorescent compounds described above bind to PSMA on cells that express PSMA on the cell surface. In some cases, fluorescent compound is internalized. Cells binding the fluorescent compound appear fluorescent, and may be imaged using fluorescence microscopy. Fluorescence-activated cell sorting (FACS) or flow cytometry may be used to separate PSMA positive cells from PSMA negative cells.

Intraoperative Tumor Mapping

Embodiments of the invention include methods of intraoperative tumor mapping or intraoperative photodiagnosis (PDD) by administering an effective amount of a compound discussed above to a subject, where the compound includes a fluorescent dye moiety. According to such embodiments, an effective amount of a compound is an amount sufficient to produce a detectable level of fluorescence when used for intraoperative tumor mapping or PDD. The compounds bind to, and may be internalized into, cells, particularly tumor cells, that express PSMA. The fluorescent compounds thereby define the boundaries of the tumor, allowing for accurate surgical removal. The compounds that includes a fluorescent dye moiety may also be used to visualize circulating tumor cells that express PSMA.

Kits

Other embodiments provide kits including a compound according to the invention. In certain embodiments, the kit provides packaged pharmaceutical compositions having a pharmaceutically acceptable carrier and a compound of the invention. In some embodiments the packaged pharmaceutical composition will include the reaction precursors necessary to generate the compound of the invention. Other packaged pharmaceutical compositions provided by the present invention further comprise indicia comprising at least one of: instructions for preparing compounds according to the invention from supplied precursors, instructions for using the composition to image cells or tissues expressing PSMA, or instructions for using the composition to image glutamatergic neurotransmission in a patient suffering from a stress-related disorder, or instructions for using the composition to image prostate cancer.

The imaging agent and carrier may be provided in solution or in lyophilized form. When the imaging agent and carrier of the kit are in lyophilized form, the kit may optionally contain a sterile and physiologically acceptable reconstitution medium such as water, saline, buffered saline, and the like. The kit may provide a compound of the invention in solution or in lyophilized form, and these components of the kit of the invention may optionally contain stabilizers such as NaCl, silicate, phosphate buffers, ascorbic acid, gentisic acid, and the like. Additional stabilization of kit components may be provided in this embodiment, for example, by providing the reducing agent in an oxidation-resistant form. Determination and optimization of such stabilizers and stabilization methods are well within the level of skill in the art.

II. Definitions

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

While the following terms in relation to the presently disclosed compounds are believed to be well understood by one of ordinary skill in the art, the following definitions are set forth to facilitate explanation of the presently disclosed subject matter. These definitions are intended to supplement and illustrate, not preclude, the definitions that would be apparent to one of ordinary skill in the art upon review of the present disclosure.

The terms substituted, whether preceded by the term "optionally" or not, and substituent, as used herein, refer to the ability, as appreciated by one skilled in this art, to change one functional group for another functional group on a molecule, provided that the valency of all atoms is maintained. When more than one position in any given structure may be substituted with more than one substituent selected from a specified group, the substituent may be either the same or different at every position.

The substituents also may be further substituted (e.g., an aryl group substituent may have another substituent off it, such as another aryl group, which is further substituted at one or more positions).

Where substituent groups or linking groups are specified by their conventional chemical formulae, written from left to right, they equally encompass the chemically identical substituents that would result from writing the structure from right to left, e.g., —CH$_2$O— is equivalent to —OCH$_2$—; —C(=O)O— is equivalent to —OC(=O)—; —OC(=O)NR— is equivalent to —NRC(=O)O—, and the like.

When the term "independently selected" is used, the substituents being referred to (e.g., R groups, such as groups R$_1$, R$_2$, and the like, or variables, such as "m" and "n"), can be identical or different. For example, both R$_1$ and R$_2$ can be substituted alkyls, or R$_1$ can be hydrogen and R$_2$ can be a substituted alkyl, and the like.

The terms "a," "an," or "a(n)," when used in reference to a group of substituents herein, mean at least one. For example, where a compound is substituted with "an" alkyl or aryl, the compound is optionally substituted with at least one alkyl and/or at least one aryl. Moreover, where a moiety is substituted with an R substituent, the group may be referred to as "R-substituted." Where a moiety is R-substituted, the moiety is substituted with at least one R substituent and each R substituent is optionally different.

A named "R" or group will generally have the structure that is recognized in the art as corresponding to a group having that name, unless specified otherwise herein. For the purposes of illustration, certain representative "R" groups as set forth above are defined below.

Description of compounds of the present disclosure is limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

Unless otherwise explicitly defined, a "substituent group," as used herein, includes a functional group selected from one or more of the following moieties, which are defined herein:

The term hydrocarbon, as used herein, refers to any chemical group comprising hydrogen and carbon. The hydrocarbon may be substituted or unsubstituted. As would be known to one skilled in this art, all valencies must be satisfied in making any substitutions. The hydrocarbon may be unsaturated, saturated, branched, unbranched, cyclic, polycyclic, or heterocyclic. Illustrative hydrocarbons are further defined herein below and include, for example, methyl, ethyl, n-propyl, isopropyl, cyclopropyl, allyl, vinyl, n-butyl, tert-butyl, ethynyl, cyclohexyl, and the like.

The term "alkyl," by itself or as part of another substituent, means, unless otherwise stated, a straight (i.e., unbranched) or branched chain, acyclic or cyclic hydrocarbon group, or combination thereof, which may be fully saturated, mono- or polyunsaturated and can include di- and multivalent groups, having the number of carbon atoms designated (i.e., C$_1$-C$_{10}$ means one to ten carbons, including 1, 2, 3, 4, 5, 6, 7, 8, 9, and 10 carbons). In particular embodiments, the term "alkyl" refers to C$_{1-20}$ inclusive, including 1, 2, 3, 4, 5, 6, 7, 8, 9, 10, 11, 12, 13, 14, 15, 16, 17, 18, 19, and 20 carbons, linear (i.e., "straight-chain"), branched, or cyclic, saturated or at least partially and in some embodiments fully unsaturated (i.e., alkenyl and alkynyl) hydrocarbon radicals derived from a hydrocarbon moiety containing between one and twenty carbon atoms by removal of a single hydrogen atom.

Representative saturated hydrocarbon groups include, but are not limited to, methyl, ethyl, n-propyl, isopropyl, n-butyl, isobutyl, sec-butyl, tert-butyl, n-pentyl, sec-pentyl, isopentyl, neopentyl, n-hexyl, sec-hexyl, n-heptyl, n-octyl, n-decyl, n-undecyl, dodecyl, cyclohexyl, (cyclohexyl)methyl, cyclopropylmethyl, and homologs and isomers thereof.

"Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a C$_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to C$_{1-8}$ straight-chain alkyls. In other embodiments, "alkyl" refers, in particular, to C$_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

The term "heteroalkyl," by itself or in combination with another term, means, unless otherwise stated, a stable straight or branched chain, or cyclic hydrocarbon group, or combinations thereof, consisting of at least one carbon atoms and at least one heteroatom selected from the group consisting of O, N, P, Si and S, and wherein the nitrogen, phosphorus, and sulfur atoms may optionally be oxidized and the nitrogen heteroatom may optionally be quaternized. The heteroatom(s) O, N, P and S and Si may be placed at any interior position of the heteroalkyl group or at the position at which alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_{2S}$—S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$.

As described above, heteroalkyl groups, as used herein, include those groups that are attached to the remainder of the molecule through a heteroatom, such as —C(O)NR', —NR'R", —OR', —SR, —S(O)R, and/or —S(O$_2$)R'. Where "heteroalkyl" is recited, followed by recitations of specific heteroalkyl groups, such as —NR'R or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein, oxo, and/or alkylene. There can be optionally inserted along the cyclic alkyl chain one or more oxygen, sulfur or substituted or unsubstituted nitrogen atoms, wherein the nitrogen substituent is hydrogen, unsubstituted alkyl, substituted alkyl, aryl, or substituted aryl, thus providing a heterocyclic group. Representative monocyclic cycloalkyl rings include cyclopentyl, cyclohexyl, and cycloheptyl. Multicyclic cycloalkyl rings include adamantyl, octahydronaphthyl, decalin, camphor, camphane, and noradamantyl, and fused ring systems, such as dihydro- and tetrahydronaphthalene, and the like.

The term "cycloalkylalkyl," as used herein, refers to a cycloalkyl group as defined hereinabove, which is attached to the parent molecular moiety through an alkyl group, also as defined above. Examples of cycloalkylalkyl groups include cyclopropylmethyl and cyclopentylethyl.

The terms "cycloheteroalkyl" or "heterocycloalkyl" refer to a non-aromatic ring system, unsaturated or partially unsaturated ring system, such as a 3- to 10-member substituted or unsubstituted cycloalkyl ring system, including one or more heteroatoms, which can be the same or different, and are selected from the group consisting of nitrogen (N), oxygen (O), sulfur (S), phosphorus (P), and silicon (Si), and optionally can include one or more double bonds.

The cycloheteroalkyl ring can be optionally fused to or otherwise attached to other cycloheteroalkyl rings and/or non-aromatic hydrocarbon rings. Heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized. In certain embodiments, the term heterocylic refers to a non-aromatic 5-, 6-, or 7-membered ring or a polycyclic group wherein at least one ring atom is a heteroatom selected from O, S, and N (wherein the nitrogen and sulfur heteroatoms may be optionally oxidized), including, but not limited to, a bi- or tri-cyclic group, comprising fused six-membered rings having between one and three heteroatoms independently selected from the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring. Representative cycloheteroalkyl ring systems include, but are not limited to pyrrolidinyl, pyrrolinyl, imidazolidinyl, imidazolinyl, pyrazolidinyl, pyrazolinyl, piperidyl, piperazinyl, indolinyl, quinuclidinyl, morpholinyl, thiomorpholinyl, thiadiazinanyl, tetrahydrofuranyl, and the like.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. The terms "cycloalkylene" and "heterocycloalkylene" refer to the divalent derivatives of cycloalkyl and heterocycloalkyl, respectively.

An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. Alkyl groups that are limited to hydrocarbon groups are termed "homoalkyl."

More particularly, the term "alkenyl" as used herein refers to a monovalent group derived from a $C_{1-20}$ inclusive straight or branched hydrocarbon moiety having at least one carbon-carbon double bond by the removal of a single hydrogen molecule. Alkenyl groups include, for example, ethenyl (i.e., vinyl), propenyl, butenyl, 1-methyl-2-buten-1-yl, pentenyl, hexenyl, octenyl, allenyl, and butadienyl.

The term "cycloalkenyl" as used herein refers to a cyclic hydrocarbon containing at least one carbon-carbon double bond. Examples of cycloalkenyl groups include cyclopropenyl, cyclobutenyl, cyclopentenyl, cyclopentadiene, cyclohexenyl, 1,3-cyclohexadiene, cycloheptenyl, cycloheptatrienyl, and cyclooctenyl.

The term "alkynyl" as used herein refers to a monovalent group derived from a straight or branched $C_{1-20}$ hydrocarbon of a designed number of carbon atoms containing at least one carbon-carbon triple bond. Examples of "alkynyl" include ethynyl, 2-propynyl (propargyl), 1-propynyl, pentynyl, hexynyl, and heptynyl groups, and the like.

The term "alkylene" by itself or a part of another substituent refers to a straight or branched bivalent aliphatic hydrocarbon group derived from an alkyl group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—CH$_2$—); ethylene (—CH$_2$—CH$_2$—); propylene (—(CH$_2$)$_3$—); cyclohexylene (—C$_6$H$_{10}$); —CH═CH—CH═CH—; —CH═CH—CH$_2$—; —CH$_2$CH$_2$CH$_2$CH$_2$—, —CH$_2$CH═CHCH$_2$—, —CH$_2$CsCCH$_2$—, —CH$_2$CH$_2$CH (CH$_2$CH$_2$CH$_3$)CH$_2$—, —(CH$_2$)$_q$—N(R)—(CH$_2$)$_r$—, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl (—O—CH$_2$—O—); and ethylenedioxyl (—O—(CH$_2$)$_2$—O—). An alkylene group can have about 2 to about 3 carbon atoms and can further have 6-20 carbons. Typically, an alkyl (or alkylene) group will have from 1 to 24 carbon atoms, with those groups having 10 or fewer carbon atoms being some embodiments of the present disclosure. A "lower alkyl" or "lower alkylene" is a shorter chain alkyl or alkylene group, generally having eight or fewer carbon atoms.

The term "heteroalkylene" by itself or as part of another substituent means a divalent group derived from heteroalkyl, as exemplified, but not limited by, —CH$_2$—CH$_2$—S—CH$_2$—CH$_2$— and —CH$_2$—S—CH$_2$—CH$_2$—NH—CH$_2$—.

For heteroalkylene groups, heteroatoms also can occupy either or both of the chain termini (e.g., alkyleneoxo, alkylenedioxo, alkyleneamino, alkylenediamino, and the like). Still further, for alkylene and heteroalkylene linking groups, no orientation of the linking group is implied by the direction in which the formula of the linking group is written. For example, the formula —C(O)OR'— represents both —C(O)OR'— and —R'OC(O)—.

The term "aryl" means, unless otherwise stated, an aromatic hydrocarbon substituent that can be a single ring or multiple rings (such as from 1 to 3 rings), which are fused together or linked covalently. The term "heteroaryl" refers to aryl groups (or rings) that contain from one to four heteroatoms (in each separate ring in the case of multiple rings) selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of above noted aryl and heteroaryl ring systems are selected from the group of acceptable substituents described below. The terms "arylene" and "heteroarylene" refer to the divalent forms of aryl and heteroaryl, respectively.

For brevity, the term "aryl" when used in combination with other terms (e.g., aryloxy, arylthioxy, arylalkyl) includes both aryl and heteroaryl rings as defined above. Thus, the terms "arylalkyl" and "heteroarylalkyl" are meant to include those groups in which an aryl or heteroaryl group is attached to an alkyl group (e.g., benzyl, phenethyl, pyridylmethyl, furylmethyl, and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like). However, the term "haloaryl," as used herein is meant to cover only aryls substituted with one or more halogens.

Where a heteroalkyl, heterocycloalkyl, or heteroaryl includes a specific number of members (e.g. "3 to 7 membered"), the term "member" refers to a carbon or heteroatom.

Further, a structure represented generally by the formula:

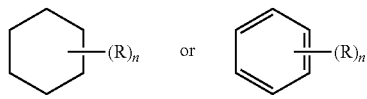

as used herein refers to a ring structure, for example, but not limited to a 3-carbon, a 4-carbon, a 5-carbon, a 6-carbon, a 7-carbon, and the like, aliphatic and/or aromatic cyclic compound, including a saturated ring structure, a partially saturated ring structure, and an unsaturated ring structure, comprising a substituent R group, wherein the R group can be present or absent, and when present, one or more R groups can each be substituted on one or more available carbon atoms of the ring structure. The presence or absence of the R group and number of R groups is determined by the value of the variable "n," which is an integer generally having a value ranging from 0 to the number of carbon atoms on the ring available for substitution. Each R group, if more than one, is substituted on an available carbon of the ring structure rather than on another R group. For example, the structure above where n is 0 to 2 would comprise compound groups including, but not limited to:

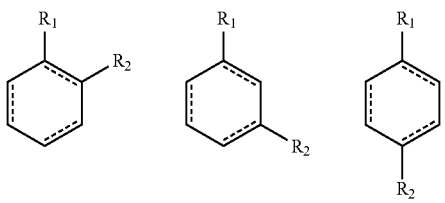

and the like.

A dashed line representing a bond in a cyclic ring structure indicates that the bond can be either present or absent in the ring. That is, a dashed line representing a bond in a cyclic ring structure indicates that the ring structure is selected from the group consisting of a saturated ring structure, a partially saturated ring structure, and an unsaturated ring structure.

The symbol ( ⌇⌇⌇⌇ ) denotes the point of attachment of a moiety to the remainder of the molecule.

When a named atom of an aromatic ring or a heterocyclic aromatic ring is defined as being "absent," the named atom is replaced by a direct bond.

Each of above terms (e.g., "alkyl," "heteroalkyl," "cycloalkyl, and "heterocycloalkyl", "aryl," "heteroaryl," "phosphonate," and "sulfonate" as well as their divalent derivatives) are meant to include both substituted and unsubstituted forms of the indicated group. Optional substituents for each type of group are provided below.

Substituents for alkyl, heteroalkyl, cycloalkyl, heterocycloalkyl monovalent and divalent derivative groups (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R'", —OC(O)R', —C(O)R', —CO$_2$R', —C(O)NR'R", —OC(O)NR'R", —NR"C(O)R', —NR'—C(O)NR"R'", —NR"C(O)OR', —NR—C(NR'R")=NR'", —S(O)R', —S(O)$_2$R', —S(O)$_2$NR'R", —NRSO$_2$R', —CN and —NO$_2$ in a number ranging from zero to (2 m'+1), where m' is the total number of carbon atoms in such groups. R', R", R'" and R"" each may independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. As used herein, an "alkoxy" group is an alkyl attached to the remainder of the molecule through a divalent oxygen. When a compound of the disclosure includes more than one R group, for example, each of the R groups is independently selected as are each R', R", R'" and R"" groups when more than one of these groups is present. When R' and R" are attached to the same nitrogen atom, they can be combined with the nitrogen atom to form a 4-, 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similar to the substituents described for alkyl groups above, exemplary substituents for aryl and heteroaryl groups (as well as their divalent derivatives) are varied and are selected from, for example: halogen, —OR', —NR'R", —SR', —SiR'R"R''', —OC(O)R', —C(O)R', —$CO_2$R', —C(O)NR'R", —OC(O)NR'R", —NR"C(O)R', —NR'—C(O)NR"R''', —NR"C(O)OR', —NR—C(NR'R"R''')=NR'''', —NR—C(NR'R")=NR'''—S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxo, and fluoro(C$_1$-C$_4$)alkyl, in a number ranging from zero to the total number of open valences on aromatic ring system; and where R', R", R''' and R'''' may be independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the disclosure includes more than one R group, for example, each of the R groups is independently selected as are each R', R", R''' and R'''' groups when more than one of these groups is present.

Two of the substituents on adjacent atoms of aryl or heteroaryl ring may optionally form a ring of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4.

One of the single bonds of the new ring so formed may optionally be replaced with a double bond. Alternatively, two of the substituents on adjacent atoms of aryl or heteroaryl ring may optionally be replaced with a substituent of the formula —(CRR')$_s$—X'—(C"R''')$_d$—, where s and d are independently integers of from 0 to 3, and X' is —O—, —NR'—, —S—, —S(O)—, —S(O)$_2$—, or —S(O)$_2$NR'—. The substituents R, R', R" and R''' may be independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the term "acyl" refers to an organic acid group wherein the —OH of the carboxyl group has been replaced with another substituent and has the general formula RC(=O)—, wherein R is an alkyl, alkenyl, alkynyl, aryl, carbocyclic, heterocyclic, or aromatic heterocyclic group as defined herein). As such, the term "acyl" specifically includes arylacyl groups, such as a 2-(furan-2-yl) acetyl)- and a 2-phenylacetyl group. Specific examples of acyl groups include acetyl and benzoyl. Acyl groups also are intended to include amides, —RC(=O)NR', esters, —RC(=O)OR', ketones, —RC(=O)R', and aldehydes, —RC(=O)H.

The terms "alkoxyl" or "alkoxy" are used interchangeably herein and refer to a saturated (i.e., alkyl-O—) or unsaturated (i.e., alkenyl-O— and alkynyl-O—) group attached to the parent molecular moiety through an oxygen atom, wherein the terms "alkyl," "alkenyl," and "alkynyl" are as previously described and can include $C_{1-20}$ inclusive, linear, branched, or cyclic, saturated or unsaturated oxo-hydrocarbon chains, including, for example, methoxyl, ethoxyl, propoxyl, isopropoxyl, n-butoxyl, sec-butoxyl, tert-butoxyl, and n-pentoxyl, neopentoxyl, n-hexoxyl, and the like.

The term "alkoxyalkyl" as used herein refers to an alkyl-O-alkyl ether, for example, a methoxyethyl or an ethoxymethyl group.

"Aryloxyl" refers to an aryl-O— group wherein the aryl group is as previously described, including a substituted aryl. The term "aryloxyl" as used herein can refer to phenyloxyl or hexyloxyl, and alkyl, substituted alkyl, halo, or alkoxyl substituted phenyloxyl or hexyloxyl.

"Aralkyl" refers to an aryl-alkyl-group wherein aryl and alkyl are as previously described, and included substituted aryl and substituted alkyl. Exemplary aralkyl groups include benzyl, phenylethyl, and naphthylmethyl.

"Aralkyloxyl" refers to an aralkyl-O— group wherein the aralkyl group is as previously described. An exemplary aralkyloxyl group is benzyloxyl, i.e., $C_6H_5$—$CH_2$—O—. An aralkyloxyl group can optionally be substituted.

"Alkoxycarbonyl" refers to an alkyl-O—C(=O)— group. Exemplary alkoxycarbonyl groups include methoxycarbonyl, ethoxycarbonyl, butyloxycarbonyl, and tert-butyloxycarbonyl.

"Aryloxycarbonyl" refers to an aryl-O—C(=O)— group. Exemplary aryloxycarbonyl groups include phenoxy- and naphthoxy-carbonyl.

"Aralkoxycarbonyl" refers to an aralkyl-O—C(=O)— group. An exemplary aralkoxycarbonyl group is benzyloxycarbonyl.

"Carbamoyl" refers to an amide group of the formula —C(=O)NH$_2$. "Alkylcarbamoyl" refers to a R'RN—C(=O)— group wherein one of R and R' is hydrogen and the other of R and R' is alkyl and/or substituted alkyl as previously described. "Dialkylcarbamoyl" refers to a R'RN—C(=O)— group wherein each of R and R' is independently alkyl and/or substituted alkyl as previously described.

The term carbonyldioxyl, as used herein, refers to a carbonate group of the formula —O—C(=O)—OR.

"Acyloxyl" refers to an acyl-O— group wherein acyl is as previously described. The term "amino" refers to the —NH$_2$ group and also refers to a nitrogen containing group as is known in the art derived from ammonia by the replacement of one or more hydrogen radicals by organic radicals. For example, the terms "acylamino" and "alkylamino" refer to specific N-substituted organic radicals with acyl and alkyl substituent groups respectively.

An "aminoalkyl" as used herein refers to an amino group covalently bound to an alkylene linker. More particularly, the terms alkylamino, dialkylamino, and trialkylamino as used herein refer to one, two, or three, respectively, alkyl groups, as previously defined, attached to the parent molecular moiety through a nitrogen atom. The term alkylamino refers to a group having the structure —NHR' wherein R' is an alkyl group, as previously defined; whereas the term dialkylamino refers to a group having the structure —NR'R", wherein R' and R" are each independently selected from the group consisting of alkyl groups. The term trialkylamino refers to a group having the structure —NR'R"R''', wherein R', R", and R''' are each independently selected from the group consisting of alkyl groups. Additionally, R', R", and/or R''' taken together may optionally be —(CH$_2$)$_k$— where k is an integer from 2 to 6. Examples include, but are not limited to, methylamino, dimethyl-amino, ethylamino, diethylamino, diethylaminocarbonyl, methylethylamino, isopropylamino, piperidino, trimethylamino, and propylamino.

The amino group is —NR'R", wherein R' and R" are typically selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

The terms alkylthioether and thioalkoxyl refer to a saturated (i.e., alkyl-S—) or unsaturated (i.e., alkenyl-S— and alkynyl-S—) group attached to the parent molecular moiety through a sulfur atom. Examples of thioalkoxyl moieties include, but are not limited to, methylthio, ethylthio, propylthio, isopropylthio, n-butylthio, and the like.

"Acylamino" refers to an acyl-NH— group wherein acyl is as previously described. "Aroylamino" refers to an aroyl-NH— group wherein aroyl is as previously described.

The term "carbonyl" refers to the —C(=O)— group, and can include an aldehyde group represented by the general formula R—C(=O)H.

The term "carboxyl" refers to the —COOH group. Such groups also are referred to herein as a "carboxylic acid" moiety.

The terms "halo," "halide," or "halogen" as used herein refer to fluoro, chloro, bromo, and iodo groups. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "hydroxyl" refers to the —OH group.

The term "hydroxyalkyl" refers to an alkyl group substituted with an —OH group.

The term "mercapto" refers to the —SH group.

The term "oxo" as used herein means an oxygen atom that is double bonded to a carbon atom or to another element.

The term "nitro" refers to the —$NO_2$ group.

The term "thio" refers to a compound described previously herein wherein a carbon or oxygen atom is replaced by a sulfur atom.

The term "sulfate" refers to the —$SO_4$ group.

The term thiohydroxyl or thiol, as used herein, refers to a group of the formula —SH.

More particularly, the term "sulfide" refers to compound having a group of the formula —SR.

The term "sulfone" refers to compound having a sulfonyl group —S($O_2$)R.

The term "sulfoxide" refers to a compound having a sulfinyl group —S(O)R

The term ureido refers to a urea group of the formula —NH—CO—$NH_2$.

Throughout the specification and claims, a given chemical formula or name shall encompass all tautomers, congeners, and optical- and stereoisomers, as well as racemic mixtures where such isomers and mixtures exist.

Certain compounds of the present disclosure may possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)-or (S)- or, as D- or L- for amino acids, and individual isomers are encompassed within the scope of the present disclosure. The compounds of the present disclosure do not include those which are known in art to be too unstable to synthesize and/or isolate. The present disclosure is meant to include compounds in racemic, scalemic, and optically pure forms. Optically active (R)- and (S)-, or D- and L-isomers may be prepared using chiral synthons or chiral reagents, or resolved using conventional techniques. When the compounds described herein contain olefenic bonds or other centers of geometric asymmetry, and unless specified otherwise, it is intended that the compounds include both E and Z geometric isomers. Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

It will be apparent to one skilled in the art that certain compounds of this disclosure may exist in tautomeric forms, all such tautomeric forms of the compounds being within the scope of the disclosure. The term "tautomer," as used herein, refers to one of two or more structural isomers which exist in equilibrium and which are readily converted from one isomeric form to another.

Unless otherwise stated, structures depicted herein are also meant to include compounds which differ only in the presence of one or more isotopically enriched atoms. For example, compounds having the present structures with the replacement of a hydrogen by a deuterium or tritium, or the replacement of a carbon by $^{13}$C- or $^{14}$C-enriched carbon are within the scope of this disclosure.

The compounds of the present disclosure may also contain unnatural proportions of atomic isotopes at one or more of atoms that constitute such compounds. For example, the compounds may be radiolabeled with radioactive isotopes, such as for example iodine-125 ($^{125}$I) or astatine-211 ($^{211}$At). All isotopic variations of the compounds of the present disclosure, whether radioactive or not, are encompassed within the scope of the present disclosure.

The compounds of the present disclosure may exist as salts. The present disclosure includes such salts. Examples of applicable salt forms include hydrochlorides, hydrobromides, sulfates, methanesulfonates, nitrates, maleates, acetates, citrates, fumarates, tartrates (e.g. (+)-tartrates, (−)-tartrates or mixtures thereof including racemic mixtures, succinates, benzoates and salts with amino acids such as glutamic acid. These salts may be prepared by methods known to those skilled in art. Also included are base addition salts such as sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent or by ion exchange. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the present disclosure contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents.

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

In addition to salt forms, the present disclosure provides compounds, which are in a prodrug form. Prodrugs of the compounds described herein are those compounds that readily undergo chemical changes under physiological conditions to provide the compounds of the present disclosure. Additionally, prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent.

The term "protecting group" refers to chemical moieties that block some or all reactive moieties of a compound and prevent such moieties from participating in chemical reactions until the protective group is removed, for example, those moieties listed and described in T. W. Greene, P. G. M. Wuts, Protective Groups in Organic Synthesis, 3rd ed. John Wiley & Sons (1999). It may be advantageous, where different protecting groups are employed, that each (different) protective group be removable by a different means. Protective groups that are cleaved under totally disparate reaction conditions allow differential removal of such protecting groups. For example, protective groups can be removed by acid, base, and hydrogenolysis. Groups such as trityl, dimethoxytrityl, acetal and tert-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid and hydroxy reactive moieties may be blocked with base labile groups such as, without limitation, methyl, ethyl, and acetyl in the presence of amines blocked with acid labile groups such as tert-butyl carbamate or with carbamates that are both acid and base stable but hydrolytically removable.

Carboxylic acid and hydroxy reactive moieties may also be blocked with hydrolytically removable protective groups such as the benzyl group, while amine groups capable of hydrogen bonding with acids may be blocked with base labile groups such as Fmoc. Carboxylic acid reactive moieties may be blocked with oxidatively-removable protective groups such as 2,4-dimethoxybenzyl, while co-existing amino groups may be blocked with fluoride labile silyl carbamates. Allyl blocking groups are useful in the presence of acid- and base-protecting groups since the former are stable and can be subsequently removed by metal or pi-acid catalysts. For example, an allyl-blocked carboxylic acid can be deprotected with a palladium(O)— catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

Typical blocking/protecting groups include, but are not limited to the following moieties:

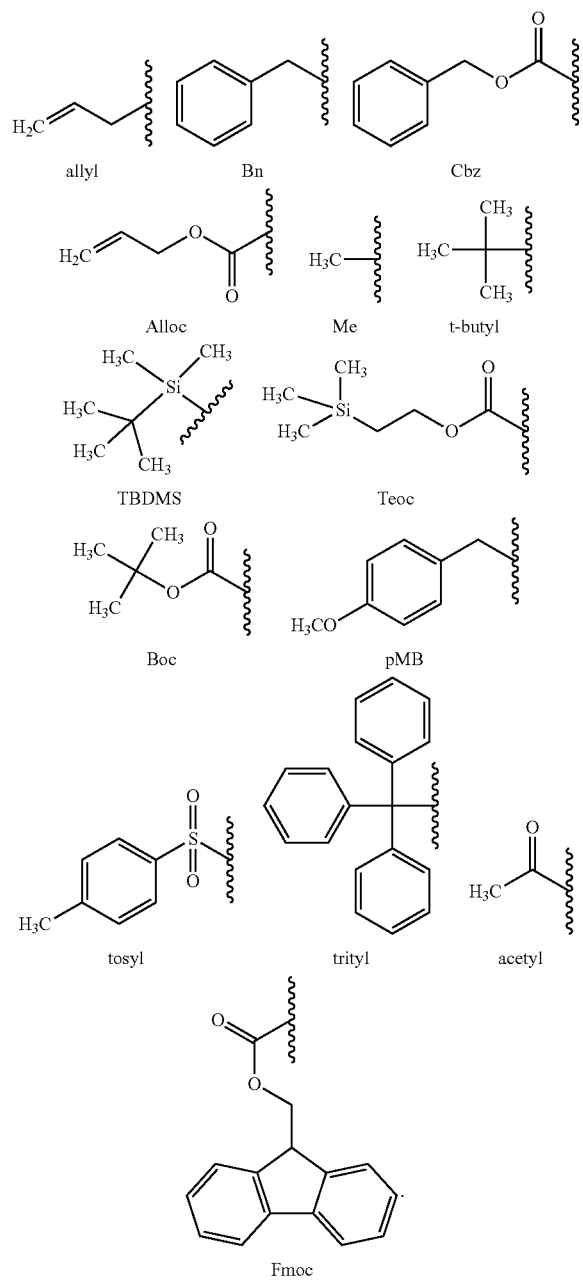

Further, as used herein, a "protecting group" is a chemical substituent which can be selectively removed by readily available reagents which do not attack the regenerated functional group or other functional groups in the molecule. Suitable protecting groups are known in the art and continue to be developed. Suitable protecting groups may be found, for example in Wutz et al. ("Greene's Protective Groups in Organic Synthesis, Fourth Edition," Wiley-Interscience, 2007). Protecting groups for protection of the carboxyl group, as described by Wutz et al. (pages 533-643), are used in certain embodiments. In some embodiments, the protecting group is removable by treatment with acid. Specific examples of protecting groups include, but are not limited to, benzyl, p-methoxybenzyl (PMB), tertiary butyl (t-Bu), methoxymethyl (MOM), methoxyethoxymethyl (MEM), methylthiomethyl (MTM), tetrahydropyranyl (THP), tetrahydrofuranyl (THF), benzyloxymethyl (BOM), trimethylsilyl (TMS), triethylsilyl (TES), t-butyldimethylsilyl (TBDMS), and triphenylmethyl (trityl, Tr). Persons skilled in the art will recognize appropriate situations in which protecting groups are required and will be able to select an appropriate protecting group for use in a particular circumstance.

The term "metal ion" as used herein refers to elements of the periodic table that are metallic and that are positively charged as a result of having fewer electrons in the valence shell than is present for the neutral metallic element. Metals that are useful in the presently disclosed subject matter include metals capable of forming pharmaceutically acceptable compositions. Useful metals include, but are not limited to, Li, Na, K, Rb, Cs, Be, Mg, Ca, Sr, and Ba. One of skill in the art will appreciate that the metals described above can each adopt several different oxidation states. In some instances, the most stable oxidation state is formed, but other oxidation states are useful in the presently disclosed subject matter.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions. Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

In the examples below the following terms are intended to have the following meaning: ACN: acetonitrile, DCM: Dichloromethane, DIPEA: N,N-Diisopropylethylamine, DMF: Dimethylformamide, HPLC: High Performance Liquid Chromatography, HRMS: High Resolution Mass Spectrometry, LRMS: Low Resolution Mass Spectrometry, NCS: N-Chlorosuccinimide, NHS: N-Hydroxysuccinimide, NMR: nuclear magnetic resonance, PMB: p-methoxybenzyl, RT: room temperature, TEA: Triethylamine, TFA: Trifluoroacetic acid, and TSTU: O—(N-Succinimidyl)-N,N,N', N'-tetramethyluronium tetrafluoroborate.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Example 1

General Methods

Chemistry. All chemicals and solvents were purchased from either Sigma-Aldrich (Milwaukee, Wis.) or Fisher Scientific (Pittsburgh, Pa.). The N-hydroxysuccinimide (NHS) esters of DyLight 800 was purchased from Thermo Fisher Scientific (Rockford, Ill. ESI mass spectra were obtained on a Bruker Esquire 3000 plus system (Billerica, Mass.). High-performance liquid chromatography (HPLC) purifications were performed on a Varian Prostar System (Varian Medical Systems, Palo Alto, Calif.).

Cell Lines and Tumor Models. PSMA$^+$ PC3 PIP and PSMA$^-$ PC3 flu cell lines were obtained from Dr. Warren Heston (Cleveland Clinic). Cells were grown to 80-90% confluence in a single passage before trypsinization and formulation in Hank's balanced salt solution (HBSS, Sigma, St. Louis, Mo.) for implantation into mice. Animal studies were carried out in compliance with guidelines related to the conduct of animal experiments of the Johns Hopkins Animal Care and Use Committee. For optical imaging studies and ex-vivo biodistribution, male NOD-SCID mice (JHU, in house colony) were implanted subcutaneously with $1 \times 10^6$ PSMA$^+$ PC3 PIP and PSMA$^-$ PC3 flu cells in opposite flanks. Mice were imaged when the tumor xenografts reached 3-5 mm in diameter.

In Vivo Imaging and Ex Vivo Biodistribution. After image acquisition at baseline (pre-injection), mouse was injected intravenously with 1 nmol of DyLight800-3 and images were acquired at 1 h, 2 h, 4 h and 24 h time points using a Pearl Impulse Imager (LI-COR Biosciences). Following the 24 h image the mouse was sacrificed by cervical dislocation and tumor, muscle, liver, spleen, kidneys and intestine were collected and assembled on a petri dish for image acquisition. All images were scaled to the same intensity for direct comparison. FIG. 1 shows the images at 24 hours postinjection of 1 nmol of DyLight800-3 in mouse with PSMA+ PC3 PIP and PSMA− PC3 flu tumors. Both whole body and ex vivo organ imaging clearly demonstrated PSMA+ PC3 PIP tumor uptake and little uptake in PSMA− PC3 flu tumor, indicating target selectivity in vivo.

Example 2

Synthesis Methods

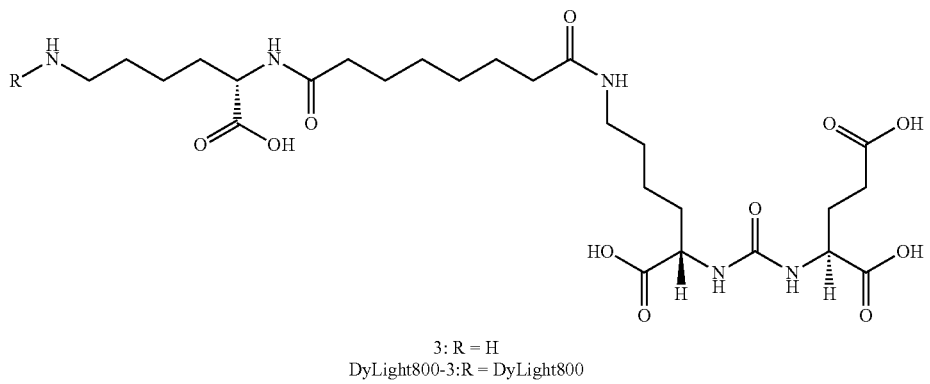

3: R = H
DyLight800-3: R = DyLight800

Synthesis of DyLight800-3: To a solution of compound 3, Chen et al., 2009, (0.5 mg, 0.7 μmol) in DMSO (0.1 mL) was added N,N-diisopropylethylamine (0.010 mL, 57.4 μmol), followed by NHS ester of DyLight800 (0.3 mg, 0.29 μmol). After 1 h at room temperature, the reaction mixture was purified by HPLC (column, Phenomenex Luna C18 10μ, 250×4.6 mm; mobile phase, A=0.1% TFA in H$_2$O, B=0.1% TFA in CH$_3$CN; gradient, 0 min=5% B, 5 min=5% B, 45 min=100% B; flow rate, 1 mL/min) to afford 0.3 mg (70%) of DyLight800-3: ESI-Mass calcd for $C_{71}H_{94}N_7O_{22}S_3^-$ [M–H]$^-$ 1492.6, found 1492.4 [M–H]$^-$.

Example 3

General

All reagents and solvents were purchased from either Sigma-Aldrich (Milwaukee, Wis.) or Fisher Scientific (Pittsburgh, Pa.). 2-{3-[5-[7-(2,5-Dioxo-pyrrolidin-1-yloxycarbonyl)-heptanoylamino]-1-(4-methoxy-benzyloxycarbonyl)-pentyl]-ureido}-pentanedioic acid bis-(4-methoxy-benzyl) ester (1) was prepared according to (Banerjee et al., J. Med. Chem., vol. 51, pp. 4504-4517, 2008). H-Lys(Boc)-OBu.HCl was purchased from Chem-Impex International (Wood Dale, Ill.). The N-hydroxysuccinimide (NHS) ester of IRDye 800CW was purchased from LI-COR Biosciences (Lincoln, Nebr.). $^1$H NMR spectra were obtained on a Bruker Avance 400 mHz Spectrometer. ESI mass spectra were obtained on a Bruker Esquire 3000 plus system. Purification by high-performance liquid chromatography (HPLC) was performed on a Varian Prostar System (Varian Medical Systems, Palo Alto, Calif.). YC-27

Compound YC-27 was prepared according the scheme shown below.

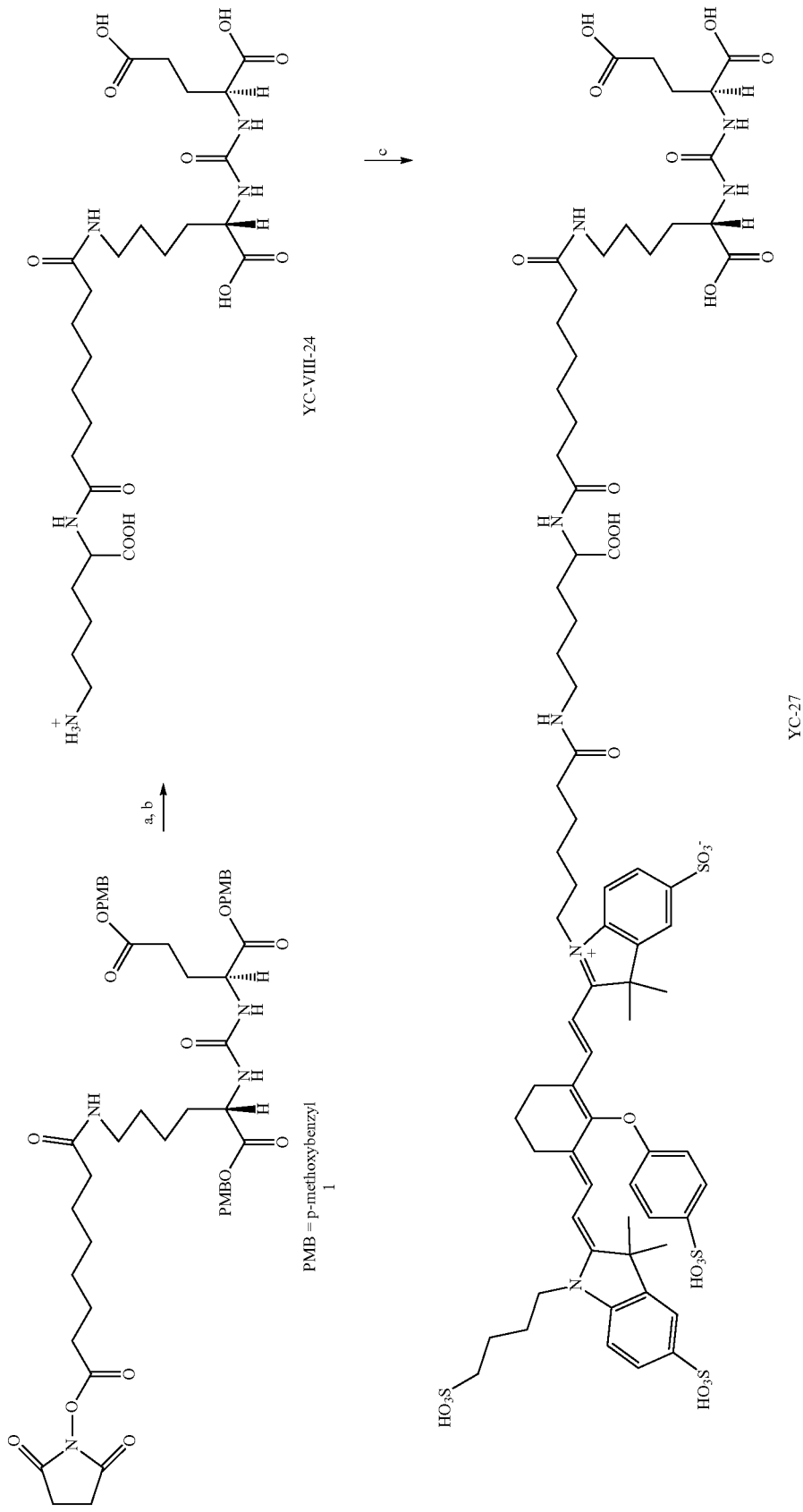

(a) H-Lys(Boc)-OBu.HCl, Et₃N, CH₂Cl₂; (b) TFA: CH₂Cl₂=1:1; (c) IRDye800CW-NHS, DIPEA, DMSO

Trifluoroacetate salt of 2-(3-{5-[7-(5-amino-1-carboxy-pentylcarbamoyl)-heptanoylamino]-1-carboxy-pentyl}-ureido)-pentanedioic acid (YC-VIII-24). To a solution of 1 (0.065 g, 0.020 mmol) in CH₂Cl₂ (2 mL) was added triethylamine (0.040 mL, 0.285 mmol), followed by H-Lys(Boc)-OBu.HCl (0.028 g, 0.083 mmol). After stirring for 2 h at room temperature, the solvent was evaporated on a rotary evaporator. A solution of TFA/CH₂Cl₂ 1:1 (2 mL) was then added to the residue and stirred for 1 h at room temperature. The crude material was purified by HPLC (column, Econosphere C18, 10µ, 250×10 mm; retention time, 15 min; mobile phase, A=0.1% TFA in H₂O, B=0.1% TFA in CH₃CN; gradient, 0 min=5% B, 25 min=25% B; flow rate, 4 mL/min) to afford 0.032 g (66%) of YC-VIII-24. ¹H NMR (400 MHz, D₂O) δ4.24-4.28 (m, 1H), 4.17-4.20 (m, 1H), 4.08-4.12 (m, 1H), 3.08-3.12 (m, 2H), 2.88-2.92 (m, 2H), 2.41-2.44 (m, 2H), 2.19-2.21 (m, 2H), 2.05-2.16 (m, 3H), 1.57-1.93 (m, 7H), 1.21-1.50 (m, 10H), 1.21 (m, 4H). ESI-Mass calcd for C₂₆H₄₆N₅O₁₁ [M]⁺ 604.3, found 604.0.

YC-27. To a solution of YC-VIII-24 (0.3 mg, 0.43 µmol) in DMSO (0.1 mL) was added N,N-diisopropylethylamine (0.002 mL, 11.4 µmol), followed by the NHS ester of IRDye 800CW (0.3 mg, 0.26 µmol). After stirring for YC-VIII-24 for 2 h at room temperature, the reaction mixture was purified by HPLC (column, Econosphere C18 5µ, 150×4.6 mm; retention time, 22 min, mobile phase, A=0.1% TFA in H₂O, B=0.1% TFA in CH₃CN; gradient, 0 min=0% B, 5 min=0% B, 45 min=100% B; flow rate, 1 mL/min) to afford 0.3 mg (72%) of YC-27. ESI-Mass calcd for C₇₂H₉₇N₇O₂₅S₄ [M]⁺ 1587.5, found 794.3 [M+H]²⁺, 1587.6 [M]⁺.

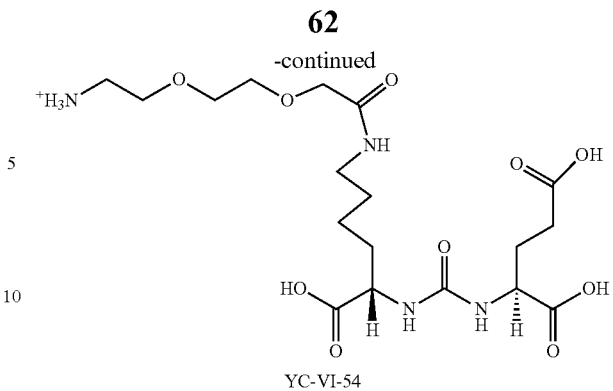

YC-VI-54

To a solution of Lys-Urea-Glu (0.103 g, 0.121 mmol, Banerjee et al *J. Med. Chem.*, vol. 51, pp. 4507-4517, 2008) in DMF (2 mL) was added Boc-NH-PEG-COOH (0.060 g, 0.135 mmol) and TBTU (0.040 g, 0.125 mmol), followed by N,N'-diisopropylethylamine (0.042 mL, 0.241 mmol). After stirring overnight at room temperature, the solvent was evaporated on a rotary evaporator. The crude material was purified by a silica column using methanol/methylene chloride (5:95) to afford 0.101 g (0.109 mmol, 90%) of YC-VI-53, which was dissolved in a solution of 3% anisole in TFA (1 mL). The mixture was reacted at room temperature for 10 min, then concentrated on a rotary evaporator. The crude material was purified by HPLC (Econosphere C18 10 u, 250×10 mm, H₂O/CH₃CN/TFA (92/8/0.1), 4 mL/min, Compound YC-VI-54 eluting at 11 min) to afford 0.035 g (57%) of compound YC-VI-54. ¹H NMR (400 MHz, D₂O) 84.17-4.21 (m, 1H), 4.10-4.13 (m, 1H), 4.00 (s, 2H), 3.67-3.71 (m, 6H), 3.14-3.20 (m, 4H), 2.43-2.46 (m, 2H), 2.08-2.13 (m, 1H), 1.87-1.93 (m, 1H), 1.76-1.79 (m, 1H), 1.63-1.67 (m, 1H), 1.45-1.50 (m, 2H), 1.33-1.40 (m, 2H). ESI-Mass calcd for C₁₈H₃₃N₄O₁₀ [M]⁺ 465.2, found 465.2.

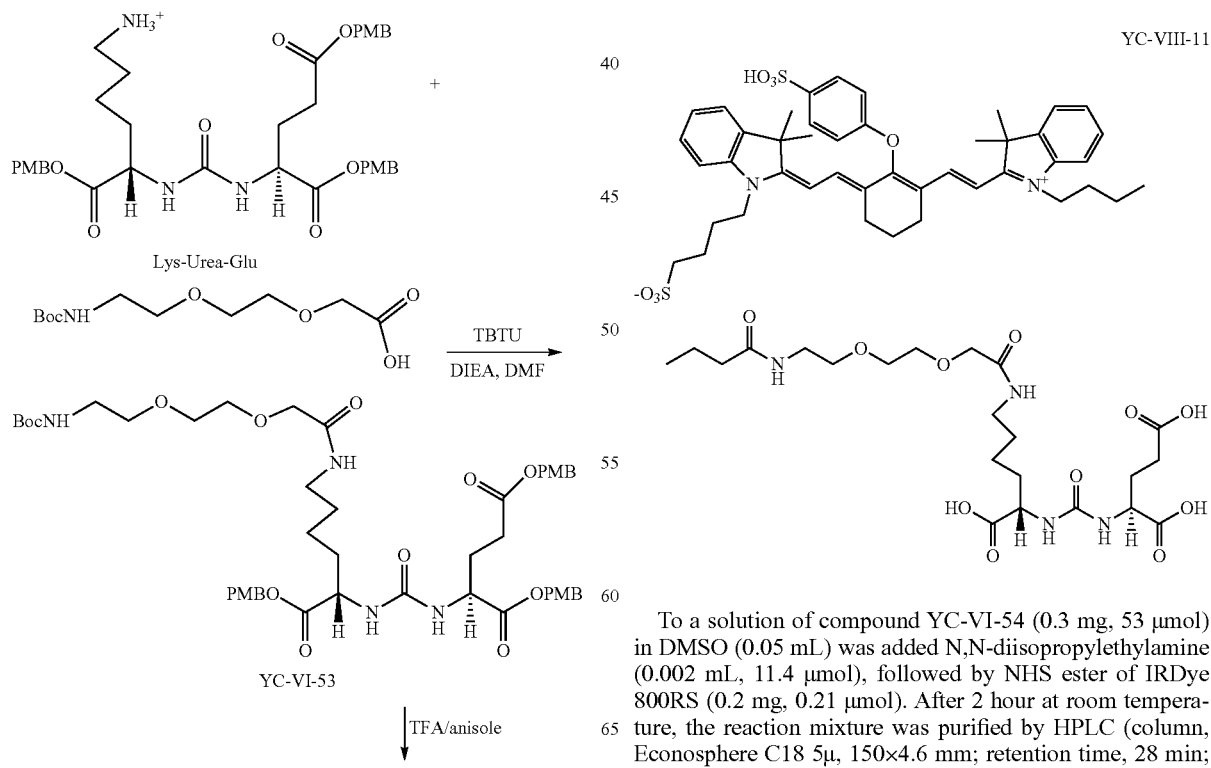

YC-VIII-11

To a solution of compound YC-VI-54 (0.3 mg, 53 µmol) in DMSO (0.05 mL) was added N,N-diisopropylethylamine (0.002 mL, 11.4 µmol), followed by NHS ester of IRDye 800RS (0.2 mg, 0.21 µmol). After 2 hour at room temperature, the reaction mixture was purified by HPLC (column, Econosphere C18 5µ, 150×4.6 mm; retention time, 28 min; mobile phase, A=0.1% TFA in H₂O, B=0.1% TFA in CH₃CN; gradient, 0 mins=0% B, 5 mins=0% B, 45 mins=100% B; flow rate, 1 mL/min) to afford 0.2 mg (75%) of compound YC-VIII-11. ESI-Mass calcd for $C_{64}H_{84}N_6O_{18}S_2$ [M]⁺ 1288.5, found 1288.9.

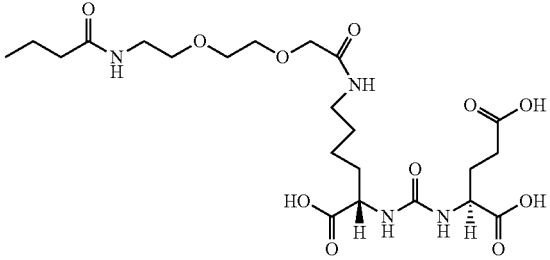

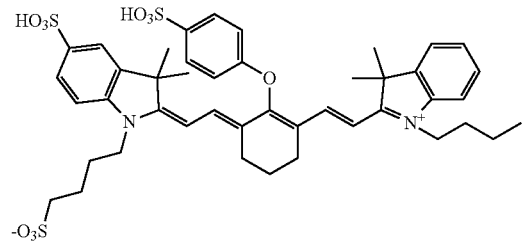

YC-VIII-12

To a solution of compound YC-VI-54 (0.3 mg, 53 μmol) in DMSO (0.05 mL) was added N,N-diisopropylethylamine (0.002 mL, 11.4 μmol), followed by NHS ester of IRDye800CW (0.2 mg, 0.17 μmol). After 2 hour at room temperature, the reaction mixture was purified by HPLC (column, Econosphere C18 5μ, 150×4.6 mm; retention time, 22 min; mobile phase, A=0.1% TFA in H₂O, B=0.1% TFA in CH₃CN; gradient, 0 mins=0% B, 5 mins=0% B, 45 mins=100% B; flow rate, 1 mL/min) to afford 0.2 mg (80%) of compound YC-VIII-12. ESI-Mass calcd for $C_{64}H_{84}N_6O_{24}S_4$ [M]⁺ 1448.4, found 1448.7.

YC-VIII-28

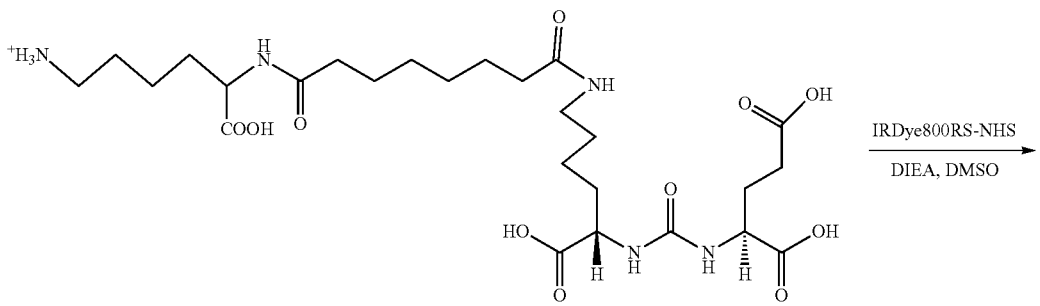

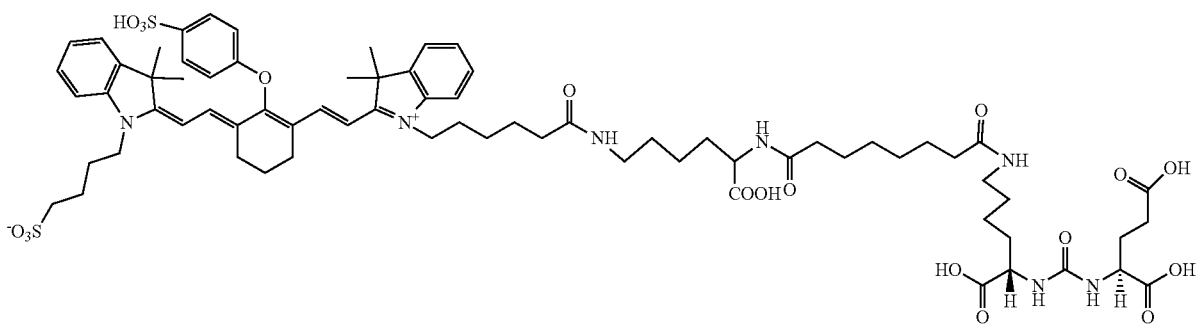

To a solution of YC-VIII-24 (prepared as described previously for YC-27) (0.3 mg, 0.42 μmol) in DMSO (0.1 mL) was added N,N-diisopropylethylamine (0.002 mL, 11.5 μmol), followed by NHS ester of IRDye 800RS (0.3 mg, 0.31 μmol). After 2 hour at room temperature, the reaction mixture was purified by HPLC (column, Econosphere C18 5μ, 150×4.6 mm; retention time, 27 min; mobile phase, A=0.1% TFA in H₂O, B=0.1% TFA in CH₃CN; gradient, 0 mins=0% B, 5 mins=0% B, 45 mins=100% B; flow rate, 1 mL/min) to afford 0.3 mg (67%) of compound YC-VIII-28. ESI-Mass calcd for $C_{72}H_{97}N_7O_{19}S_2$ [M]⁺ 1427.6, found 714.4 [M+H]²⁺, 1427.8 [M]⁺.

YC-VIII-30

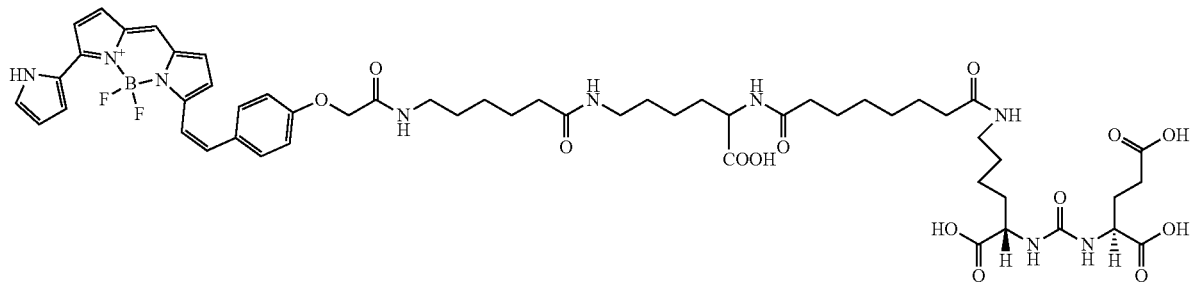

To a solution of YC-VIII-24 (0.5 mg, 0.70 μmol) in DMSO (0.1 mL) was added N,N-diisopropylethylamine (0.005 mL, 28.7 μmol), followed by NHS ester of BODIPY 650/665-X (0.3 mg, 0.47 μmol). After 2 hour at room temperature, the reaction mixture was purified by HPLC (column, Econosphere C18 5μ, 150×4.6 mm; retention time, 28 min; mobile phase, A=0.1% TFA in $H_2O$, B=0.1% TFA in $CH_3CN$; gradient, 0 mins=0% B, 5 mins=0% B, 45 mins=100% B; flow rate, 1 mL/min) to afford 0.4 mg (75%) of compound YC-VIII-30. ESI-Mass calcd for $C_{55}H_{73}BF_2N_9O_{14}$ $[M+H]^+$ 1132.5, found 1132.0.

YC-VIII-31

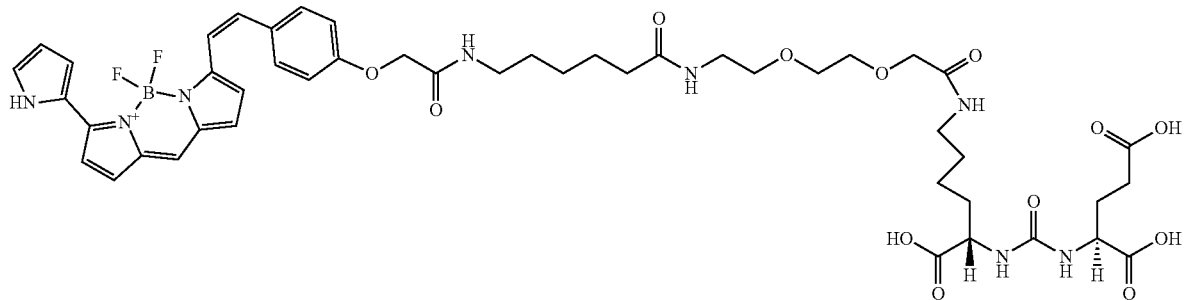

To a solution of YC-VI-54 (0.5 mg, 0.70 μmol) in DMSO (0.1 mL) was added N,N-diisopropylethylamine (0.005 mL, 28.7 μmol), followed by NHS ester of BODIPY 650/665-X (0.3 mg, 0.47 μmol). After 2 hour at room temperature, the reaction mixture was purified by HPLC (column, Econosphere C18 5μ, 150×4.6 mm; retention time, 29 min; mobile phase, A=0.1% TFA in $H_2O$, B=0.1% TFA in $CH_3CN$; gradient, 0 mins=0% B, 5 mins=0% B, 45 mins=100% B; flow rate, 1 mL/min) to afford 0.4 mg (86%) of compound YC-VIII-31. ESI-Mass calcd for $C_{47}H_{59}BF_2N_8O_{13}$ $[M]^+$ 992.4, found 992.9.

YC-VIII-41

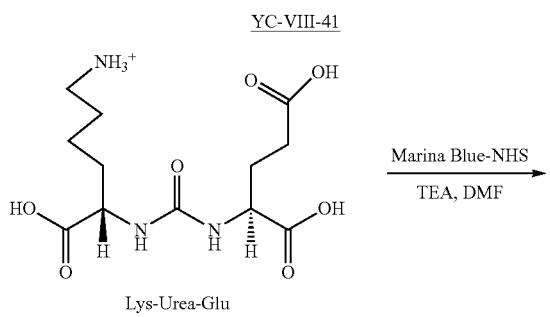

-continued

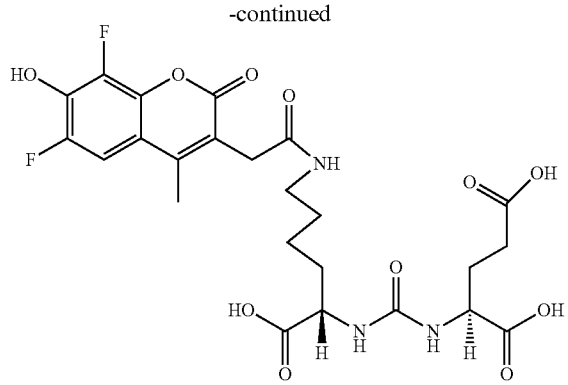

To a solution of Lys-Urea-Glu (4.0 mg, 9.6 μmol) in DMF (0.5 mL) was added triethylamine (0.01 mL, 71.7 μmol), followed by Marina Blue-NHS ester (1.8 mg, 4.9 μmol). After 2 hour at room temperature, the reaction mixture was purified by HPLC (column, Econosphere C18 10μ, 250×10 mm; retention time, 14 min; mobile phase, $H_2O/CH_3CN/$ TFA=85/15/0.1; flow rate, 4 mL/min) to afford 2.5 mg (89%) of compound YC-VIII-41. $^1H$ NMR (400 MHz, $D_2O$) δ 7.40 (d, J=11.6 Hz, 1H), 4.23-4.31 (m, 1H), 4.15-4.19 (m, 1H), 3.64 (s, 2H), 3.19-3.23 (m, 2H), 2.49-2.53 (m, 2H), 2.39 (s, 3H), 2.06-2.17 (m, 1H), 1.95-1.99 (m, 1H), 1.83-1.90 (m, 1H), 1.72-1.80 (m, 1H), 1.52-1.55 (m, 2H), 1.40-1.45 (m, 2H). ESI-Mass calcd for $C_{24}H_{28}F_2N_3O_{11}$ $[M+H]^+$ 572.2, found 571.8.

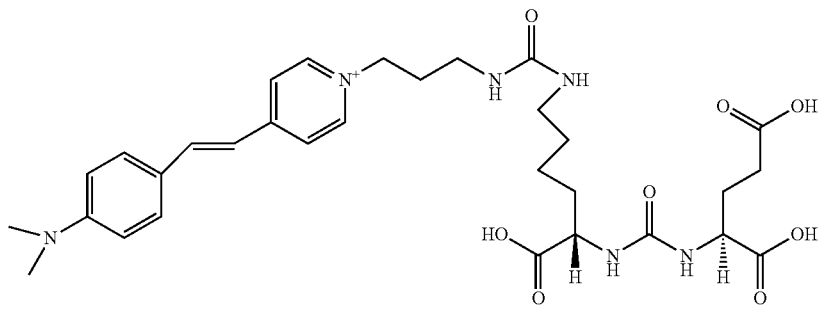

YC-VIII-52

To a solution of Lys-Urea-Glu (4.0 mg, 9.6 μmol) in DMSO (0.5 mL) was added N,N-diisopropylethylamine (0.020 mL, 114.8 μmol), followed by 4-[2-(4-dimethyl-amino-phenyl)-vinyl]-1-(3-isothiocyanato-propyl)-pyridium (3 mg, 7.4 μmol). After 2 hour at room temperature, the reaction mixture was purified by HPLC (column, Econosphere C18 10μ, 250×10 mm; retention time, 13 min; mobile phase, A=0.1% TFA in $H_2O$, B=0.1% TFA in $CH_3CN$; gradient, 0 mins=10% B, 20 mins=60% B; flow rate, 4 mL/min) to afford 1.3 mg (24%) of compound YC-VIII-52. ESI-Mass calcd for $C_{31}H_{43}N_6O_7S$ $[M]^+$ 643.3, found 642.9.

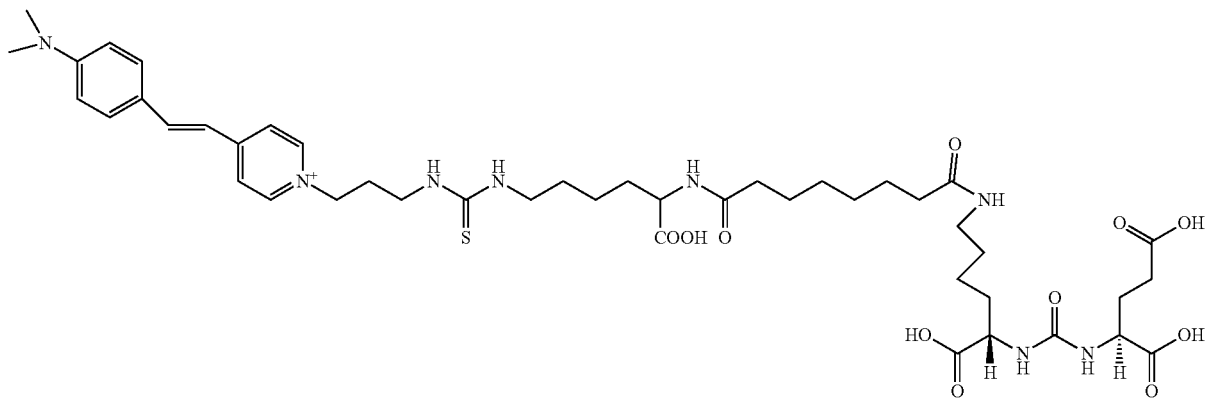

YC-VIII-74

To a solution of YC-VIII-24 (3.0 mg, 4.2 μmol) in DMSO (0.5 mL) was added N,N-diisopropylethylamine (0.020 mL, 114.8 μmol), followed by 4-[2-(4-dimethylamino-phenyl)-vinyl]-1-(3-isothiocyanato-propyl)-pyridium (2 mg, 4.9 μmol). After 2 hour at room temperature, the reaction mixture was purified by HPLC (column, Econosphere C18 5μ, 150×4.6 mm; retention time, 15 min; mobile phase, A=0.1% TFA in $H_2O$, B=0.1% TFA in $CH_3CN$; gradient, 0 mins=0% B, 5 mins=0% B, 45 mins=100% B; flow rate, 1 mL/min) to afford 2 mg (47%) of compound YC-VIII-74. ESI-Mass calcd for $C_{45}H_{67}N_8O_{11}S$ $[M]^+$ 927.5, found 927.0.

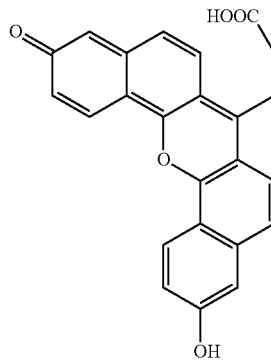

YC-VIII-63

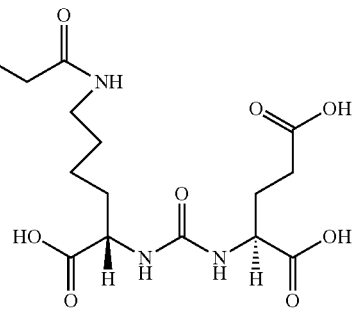

YC-IX-92

To a solution of YC-VIII-24 (5.0 mg, 7.0 µmol) in DMF (1 mL) was added triethylamine (0.020 mL, 143.5 µmol), followed by NHS ester of 5-(and-6)-carboxynaphthofluorescein (4.0 mg, 7.0 µmol). After 1 hour at room temperature, the reaction mixture was purified by HPLC (column, Econosphere C18 10µ, 250×10 mm; retention time, minor product at 17 min, major product at 20 min); mobile phase, $H_2O/CH_3CN/TFA=70/30/0.1$; flow rate, 4 mL/min) to afford 0.3 mg of minor and 2.2 mg of major product (two isomers of YC-VIII-63). ESI-Mass calcd for $C_{55}H_{59}N_5O_{17}$ $[M]^+$ 1061.4, found 1061.6 (for both minor and major product).

To a solution of Lys-Urea-Glu (0.2 mg, 0.48 µmol) in DMSO (0.05 mL) was added N,N-diisopropylethylamine (0.002 mL, 11.5 µmol), followed by NHS ester of IRDye 800RS (0.2 mg, 0.21 µmol). After 2 hour at room temperature, the reaction mixture was purified by HPLC (column, Econosphere C18µ, 150×4.6 mm; retention time, 23 min; mobile phase, A=0.1% TFA in $H_2O$, B=0.1% TFA in $CH_3CN$; gradient, 0 mins=0% B, 5 mins=0% B, 45 mins=100% B; flow rate, 1 mL/min) to afford 0.2 mg (84%) of compound YC-IX-92. ESI-Mass calcd for $C_{58}H_{73}N_5O_{15}S_2$ $[M]^+$ 1143.5, found 572.5 $[M+H]^{2+}$, 1144.0 $[M]^+$.

Characterization—Fluorescence

Fluorescence spectra were recorded using a Varian Cary Eclipse fluorescence spectrophotometer (Varian Medical Systems) with excitation from a Xenon arc lamp. YC-27 was dissolved in water. All of the fluorescence measurements were performed in aqueous solution under ambient conditions. The fluorescence quantum yield of YC-27 was measured using an aqueous solution of ICG ($\Phi$=0.016 (Sevick-Muraca et al., Photochem. Photobiol., vol. 66, pp. 55-64, 1997), excitation wavelength at 775 nm) as the standard (FIG. 2). The fluorescence intensity data were collected in the spectral region 780-900 nm over which quantum yield was integrated. Time-resolved intensity decays were recorded using a PicoQuant Fluotime 100 time-correlated single-photon counting (TCSPC) fluorescence lifetime spectrometer (PicoQuant, Berlin, DE). The excitation was obtained using a pulsed laser diode (PicoQuant PDL800-B) with a 20 MHz repetition rate. The fluorescence intensity decay of YC-27 was analyzed in terms of the single-exponential decay using the PicoQuant Fluofit 4.1 software with deconvolution of the instrument response function and nonlinear least squares fitting. The goodness-of-fit was determined by the $\chi^2$ value.

The electronic spectrum of YC-27 exhibited an absorbance maximum at 774 nm with an extinction coefficient of 158,900 $M^{-1}$. Upon excitation, YC-27 provided intense fluorescence with an emission maximum at 792 nm and a fluorescence lifetime of 443 psec in aqueous solution (FIG. 3A-FIG. 3B). Using an excitation wavelength of 775 nm, YC-27 demonstrated a fluorescence quantum yield of 0.053 in aqueous solution relative to ICG, which demonstrated a quantum yield of 0.016 (FIG. 2) (Sevick-Muraca et al., Photochem. Photobiol., vol. 66, pp. 55-64, 1997), attesting to the efficiency of this IRDye 800CW-based compound. That is significant because ICG has been used previously for intraoperative tumor mapping (K. Gotoh, T. Yamada, O. Ishikawa, H. Takahashi, H. Eguchi, M. Yano, H. Ohigashi, Y. Tomita, Y. Miyamoto, and S. Imaoka, A novel image-guided surgery of hepatocellular carcinoma by indocyanine green fluorescence imaging navigation. J. Surg. Oncol., 2009).

In vitro NAALADase Activity

PSMA inhibitory activity of YC-27 was determined using a fluorescence-based assay according to a previously reported procedure (Chen et al., J. Med. Chem., vol. 51, pp. 7933-7943, 2008). Briefly, lysates of LNCaP cell extracts (25 µL) were incubated with the inhibitor (12.5 µL) in the presence of 4 µM N-acetylaspartylglutamate (NAAG) (12.5 µL) for 120 min. The amount of glutamate released by NAAG hydrolysis was measured by incubation with a working solution (50 µL) of the Amplex Red Glutamic Acid Kit (Molecular Probes Inc., Eugene, Oreg.) for 60 min. Fluorescence was measured with a VICTOR$^3$V multilabel plate reader (Perkin Elmer Inc., Waltham, Mass.) with excitation at 530 nm and emission at 560 nm. Inhibition curves were determined using semi-log plots, and IC$_{50}$ values were determined at the concentration at which enzyme activity was inhibited by 50%. Assays were performed in triplicate. Enzyme inhibitory constants (K$_i$ values) were generated using the Cheng-Prusoff conversion. Data analysis was performed using GraphPad Prism version 4.00 for Windows (GraphPad Software, San Diego, Calif.).

This assay is free from the interference of IRDye 800CW because the excitation/emission maxima of IRDye 800CW are remote from those of resorufin ($\lambda_{ex}$=563 nm, $\lambda_{em}$=587 nm), which provides the fluorescent readout in the assay. The K$_i$ value of YC-27 was 0.37 nM with 95% confidence intervals from 0.18 nM to 0.79 nM. Under the same experimental conditions, the K$_i$ value of the known PSMA inhibitor ZJ-43 (Zhou et al., Nat. Rev. Drug Discov., vol. 4, pp. 1015-1026, 2005) was 2.1 nM, indicating the high inhibitory capacity of YC-27. The inhibition curve of YC-27, which is expressed with respect to the amount of glutamate released from hydrolysis of NAAG, is shown in FIG. 4.

Biodistribution and Imaging

Cell Culture and Animal Models. Both PSMA-expressing (PSMA+ PC3-PIP) and non-expressing (PSMA− PC3-flu) prostate cancer cell lines (Chang et al, Cancer Res., vol. 59, pp. 3192-3198, 1999) were grown in RPMI 1640 medium (Invitrogen, Carlsbad, Calif.) containing 10% fetal bovine serum (FBS) (Invitrogen) and 1% Pen-Strep (Biofluids, Camarillo, Calif.). All cell cultures were maintained in 5% carbon dioxide (CO$_2$), at 37.0° C. in a humidified incubator. Animal studies were undertaken in compliance with the regulations of the Johns Hopkins Animal Care and Use Committee. Six- to eight-week-old male, non-obese diabetic (NOD)/severe-combined immunodeficient (SCID) mice (Charles River Laboratories, Wilmington, Mass.) were implanted subcutaneously (s.c.) with PC3-PIP and PC3-flu cells (2×10$^6$ in 100 µL of Matrigel) at the forward left and right flanks, respectively. Mice were imaged or used in ex vivo biodistribution assays when the xenografts reached 5 to 7 mm in diameter.

In vivo Imaging and Ex vivo Biodistribution. Mouse #1 was injected with 10 nmol and mouse #2 with 1 nmol of YC-27 in 200 µL of PBS intravenously (i.v.) via the lateral tail vein. Mouse #3 was injected with 1 nmol of YC-27 and also co-injected with 1 µmol of the known PSMA inhibitor 2-{3-[1-carboxy-5-(4-iodo-benzoylamino)-pentyl]-ureido}-pentanedioic acid (DCIBzL) (Chen et al., J. Med. Chem., vol. 51, pp. 7933-7943, 2008; Barinka et al., J. Med. Chem. vol. 51, pp. 7737-7743, 2008) in 200 µL of PBS i.v. to assess for PSMA binding specificity. Images were acquired at an array of post-injection (p.i.) time points starting at 10 min p.i. using a dedicated small animal optical imaging instrument, the Pearl Imager (LI-COR Biosciences). The Pearl Imager uses diffusive lasers optimized for IRDye 800CW. The instrument employs a CCD camera with a field-of-view of 11.2 cm×8.4 cm at the surface of the imaging bed. The scan time was less than 30 sec to complete white light, 700 nm channel and 800 nm channel image acquisition. Images are displayed using a pseudocolor output with corresponding scale. All images were acquired at the same parameter settings and are scaled to the same maximum values. Imaging bed temperature was adjusted to 37° C. Animals received inhalational anesthesia (isoflurane) through a nose cone attached to the imaging bed. Animals were sacrificed by cervical dislocation for ex vivo imaging studies at the end of acquisition of the in vivo images. Ex vivo images were acquired first by midline surgical laparotomy and then again by harvesting liver, spleen, stomach, small intestine, kidneys, urinary bladder, PC3-PIP and PC3-flu tumors and displaying them individually on plastic Petri dishes. Estimates of signal output were provided by drawing three circular regions of interest within each tumor and determining the average signal (arbitrary units)/area using the manufacturer's software.

FIG. 5A-FIG. 5O (mouse #1) depict the pharmacokinetic behavior of YC-27 in vivo. In this experiment 10 nmol of YC-27 was administered intravenously and the animal was imaged repeatedly over a three day period. Although difficult to quantify as these are planar images, one can see clearly increased uptake in the PSMA+ PC3-PIP tumor relative to the control (PSMA-negative) PC3-flu tumor at 18.5 h p.i. through 70.5 h p.i. (FIG. 5C through FIG. 5M). Using quantitative real time polymerase chain reaction (qRT-PCR) we measured the relative amounts of PSMA mRNA expression in extracts of the tumors in mice #1-3, and confirmed that PC3-PIP tumors (left flank) expressed PSMA mRNA at levels several million times higher than PC3-flu tumors (right flank) (data not shown). Panels 5L and 5M show emission from the intact, living, unshaven animal, while panels 5N and 5O are postmortem studies with organs exposed. Note that in 5L one can barely discern the kidneys, a known target site for PSMA (Tasch et al., Crit. Rev. Immunol., vol. 21, pp. 249-261, 2001; Pomper et al., Mol. Imaging, vol. 1, pp. 96-101, 2002; Kinoshita et al., World J. Surg., vol. 30, pp. 628-636, 2006), while the kidneys are clearly visible in 5O when exposed. A portion of that renal light emission may be due to clearance of this relatively hydrophilic compound. The estimated target-to-nontarget ratio (PC-3 PIP vs. PC-3 flu light output) was 10 when comparing the tumors from panel M (70.5 h p.i.).

The experiment in FIG. 6A-FIG. 6T was performed with 10-fold less YC-27 administered than in the previous experiment. Despite reducing the concentration of YC-27, PSMA+ PC3-PIP tumor could be seen clearly at one day p.i. (FIG. 6A-FIG. 6J, mouse #2, Left Panels). DCIBzL, a known, high-affinity PSMA inhibitor, was co-administered with YC-27 as a test of binding specificity (FIG. 6K-FIG. 6T, mouse #3, Right Panels). Nearly all of the light emission from target tumor, as well as kidneys, was blocked, demonstrating the specificity of this compound for PSMA in vivo. The estimated target-to-nontarget ratio (PC-3 PIP vs. PC-3 flu light output) was 26 when comparing the tumors from panel F (20.5 h p.i.). By administering 1 nmol to this ~25 g mouse, we have realized the high sensitivity of in vivo optical imaging, rivaling that of the radiopharmaceutical-based techniques. For example, 1 nmol converts to 1.6 μg injected. If we synthesized a similar compound labeled with $^{18}F$ or other radionuclide at 1,000 mCi/μmol (37 GBq/μmol), and administered a standard dose of 200 μCi (7.4 MBq) to a mouse, we would be injecting 0.3 μg.

Interestingly, in mouse #1, which received 10 nmol of YC-27, we observed a small degree of non-specific uptake at the 23 h time point, manifested as uptake within PSMA-negative PC3-flu tumors. That finding could be due to enhanced permeability and retention of YC-27. No non-specific uptake/retention was observed at a similar, 20.5 h, time point in mouse #2, which received a 10-fold lower dose. That finding suggests the need for further optimization of dose and timing for in vivo applications.

Discussion

A wide variety of low molecular weight PSMA-based imaging agents have been synthesized, including those using the urea scaffold (Banerjee et al., J. Med. Chem., vol. 51, pp. 4504-4517, 2008; Chen et al., J. Med. Chem., vol. 51, pp. 7933-7943, 2008; Zhou et al., Nat. Rev. Drug Discov., vol. 4, pp. 1015-1026, 2005; Pomper et al., Mol. Imaging, vol. 1, pp. 96-101, 2002; Foss et al., Clin. Cancer Res., vol. 11, pp. 4022-4028, 2005; Humblet et al., Mol. Imaging, vol. 4, pp. 448-462, 2005; Misra et al., J. Nucl. Med., vol. 48, pp. 1379-1389, 2007; Mease et al., Clin. Cancer Res., vol. 14, pp. 3036-3043, 2008; Liu et al., Prostate, vol. 68, pp. 955-964, 2008; Humblet et al., J. Med. Chem., vol. 52, pp. 544-550, 2009; Kularatne et al., Mol. Pharm., vol. 6, pp. 790-800, 2009; Hillier et al., Cancer Res., vol. 69, pp. 6932-6940, 2009). Those compounds have primarily been radiopharmaceuticals, but optical agents exist. In two separate studies Humblet et al. reported the synthesis of mono- and polyvalent NIR fluorescent phosphonate derivatives for imaging PSMA, but little accumulation in PSMA-expressing tumors was evident in the former study (Humblet et al., Mol. Imaging, vol. 4, pp. 448-462, 2005) while no in vivo results were reported in the latter (Humblet et al., J. Med. Chem., vol. 52, pp. 544-550, 2009). Liu et al have also synthesized fluorescent phosphonate derivatives and have demonstrated their PSMA-binding specificity and intracellular localization in vitro (Liu et al., Prostate, vol. 68, pp. 955-964, 2008). Recently Kularatne et al. have synthesized fluorescent (fluorescein and rhodamine) urea derivatives that demonstrate PSMA migration to endosomes (Kularatne et al., Mol. Pharm., vol. 6, pp. 790-800, 2009). We arrived at YC-27 based on structure-activity relationships developed for PSMA-binding ureas, which were focused on improving pharmacokinetics for use in vivo by optimization of the linker-chelate complex (Banerjee et al., J. Med. Chem., vol. 51, pp. 4504-4517, 2008). Calculated hydrophobicity values (Ghose et al., J. Phys. Chem. A, vol. 102, pp. 3762-3772, 1998) suggest that YC-27 should be considerably more hydrophobic (ALogD=5.96) than radiopharmaceuticals such as [$^{125}I$]DCIBzL (ALogD=1.19), perhaps accounting for its long tumor retention, which is desirable for an optical imaging agent intended for intraoperative use. We confirmed greater hydrophobicity of YC-27 relative to DCIBzL through reverse-phase HPLC (data not shown)

Synthesis of YC-VIII-36

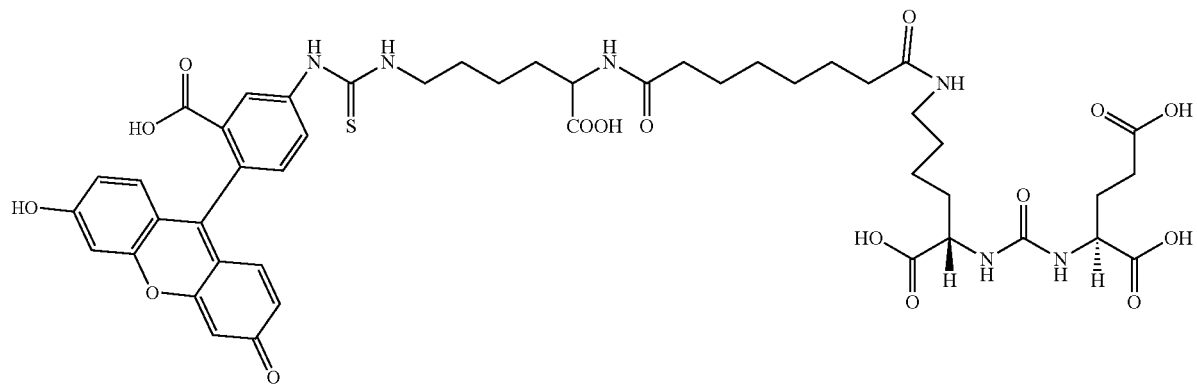

To a solution of YC-VIII-24 (prepared as described in Example 5) (1.5 mg, 0.21 μmol) in DMF (1 mL) was added triethylamine (0.005 mL, 35.9 μmol), followed by fluorescein isothiocyanate isomer 1 (1 mg, 2.57 μmol). After 2 hours at room temperature, the reaction mixture was purified by HPLC (column, Econosphere C18 5μ, 150×4.6 mm; retention time, 15 min; mobile phase, $H_2O/CH_3CN/TFA$=75/25/0.1; flow rate, 1 mL/min) to afford 1.5 mg (72%) of compound YC-VIII-36. ESI-Mass calcd for $C_{47}H_{57}N_6O_{16}S$ [M+H]$^+$ 993.4, found 992.8.

Cell Labeling

PSMA positive PIP cells, and PSMA negative FLU cells were treated with compound YC-VIII-36 (40 nM) and 4',6-diamidino-2-phenylindole (DAPI, blue). FIG. 7A-FIG. 7D show fluorescence of cells expressing PSMA (green fluorescence, top left). PIP and FLU cells were treated with both YC-VIII-36 and PSMA inhibitor PMPA (5 μM), showing inhibition of cellular fluorescence by PMPA (FIG. 7A-FIG. 7D, bottom).

FIG. 8A-FIG. 8H show PC3-PIP cells treated with DAPI (blue) and varying concentrations of YC-VIII-36 (green).

FIG. 9A-FIG. 9D show time dependent internalization of YC-VIII-36 into PC3-PIP cells treated with YC-VIII-36 (green) and DAPI (blue). The time dependent internalization study was done as described (Liu et al., Prostate vol. 68, pp. 955-964, 2008) with appropriate modifications. Briefly, PC3-PIP cells were seeded as above. The cells were first pre-chilled by incubating with ice cold complete growth media and then incubated with ice cold complete growth media containing 500 nM of compound YC-VIII-36 at 40 C for 1 hr. After 1 hr of incubation the excess compound was removed by washing the wells twice with ice-cold complete growth media and then the wells were replenished with pre-warmed complete growth media. The chamber slides containing cells were incubated for 10 min, 30 min, 60 min and 180 min at 37° C. in a humidified incubator.

In Vivo Imaging

FIG. 10A-FIG. 10F show titration and detection of varying amounts of YC-VIII-36 injected subcutaneously into a nude mouse. (IVIS spectrum with 10 second exposure followed by spectral unmixing).

FIG. 11A-FIG. 11H and FIG. 12A-FIG. 12E (top) show fluorescence images of a PSMA+ PC3-PIP and PSMA– PC3-flu tumor-bearing mouse injected intravenously with exemplary compound YC-VIII-36. Compound YC-VIII-36 (150 µg) was injected into the tail vein of a nude mouse. The excitation frequency was 465 nm with a 5 s exposure. Fluorescence emission was measured at 500, 520, 540, and 580 nm, followed by spectral unmixing.

FIG. 12A-FIG. 12E (bottom) show the biodistribution of compound YC-VII-36 (150 µg) 180 minutes after injection.

FACS and Cell Sorting

Flow cytometric analysis (FCA): Confluent flasks of PC3-PIP, PC3-flu and LNCap cells were trypsinized, washed with complete growth media (to neutralize trypsin) and counted. Approximately 5 million of each cell type in suspension was incubated with 1 mM of compound YC-VIII-36 for 30 min with occasional shaking at 37° C. in the humidified incubator with 5% $CO_2$. After incubation, the cells were washed twice with ice cold KRB buffer and fixed with 2% paraformaldehyde (ice cold). The samples were stored on ice and protected from light until the FCA was done. FCA was performed using a FACS Calibur flow cytometer (Becton Dickinson, San Jose, Calif.). For data acquisition, singlets were gated as the prominent cluster of cells identified from a plot of side scatter (SSC) width versus forward scatter (FSC) width to ensure that cell aggregates were excluded from analysis. 50,000 total events were counted to estimate the positively stained cells from a plot of Fl-1 (X-axis) versus Fl-2 (Y-axis). All data were analyzed using CellQuest version 3.3 software.

Flow sorting: PC3-PIP cells were labeled with 1 mM of compound YC-VIII-36 for 30 min at 37° C. in the humidified incubator with 5% $CO_2$. Cells were washed twice with ice cold KRB buffer and stored on ice. Flow sorting was performed using FACS Aria system (Becton Dickinson, San Jose, Calif.) within 10-15 minutes after completion of last wash. Both the stained (positive) and also the unstained (negative) subpopulations were collected in sterile tubes containing 3 ml of complete growth media. Following sorting, cells were centrifuged, resuspended in warm complete growth media, transferred to tissue culture flasks and incubated at 37° C. in the humidified incubator with 5% $CO_2$ for culture. The sorted subpopulations, "PIP-positive (PIP-pos)" and "PIP-negative (PIP-neg)" cells, were re-analyzed by FCA (as above) at passage 3 for further confirmation of their heterogeneity.

Determination of saturation dose in flow cytometry: Approximately 5 million cells each of PIP-pos (sorted) and PC3-flu were labeled as above with varying doses of compound #. The cells were washed twice with ice cold KRB buffer and fixed with 2% paraformaldehyde (ice cold). The samples were stored on ice and protected from light till the FCA was done. Singlets were gated as above in a plot of SSC vs. FSC to exclude the aggregates. Standard gating was used on X-axis (Fl-1) for analysis of stained cells in all the doses.

PC3-flu, PC3-PIP, and LNCaP cells were treated with compound YC-VIII-36, and analyzed using fluorescence activated cell sorting (FACS) to determine the percentage of cells expressing PSMA on the cell surface. FIG. 13A-FIG. 13C show FACS analysis showing the percent subpopulation of PSMA positive cells in PC3-flu, PC3-PIP, and LNCaP cells. As expected PC3-flu (PSMA–) cells (left) show a very small percentage, while PC3-PIP (PSMA+, center) and LNCaP (PSMA+ right) show greater percentages.

PC3-PIP (PSMA+) cells were sorted using FACS following treatment with compound YC-VIII-36. FIG. 14A-FIG. 14E show cell sorting of PC3-PIP cells, including initial percentage (top center), and after 3 passages of sorting (bottom). Region R2 indicates positive PSMA surface expression, as indicated by binding compound YC-VIII-36. The results show an increase in the percentage of PSMA expressing cells following three rounds of cell sorting.

Determination of detection limit (FIG. 15A-FIG. 15F): PIP-pos cells were mixed with 10 million of PC3-flu cells in triplicates in different ratios—1 in $10^6$, $10^5$, $10^4$, $10^3$ and $10^2$ respectively. All the tubes containing cell suspensions in complete growth media including controls [10 million PC3-flu cells with 0% PIP-pos cells and 10 million PIP-pos cells (100%)] were incubated with 100 nM of compound #YC-VIII-36 at 37° C. in the humidified incubator with 5% $CO_2$ as above, with occasional stirring. The cells were washed, fixed with 2% paraformaldehyde as above and analyzed with LSRII (Becton Dickinson, San Jose, Calif.) for the determination of detection limit. Singlets were gated as above in a plot of SSC vs. FSC to exclude the aggregates. 1 million total events were counted to estimate the positively stained cells from plot of Fl-1 (X-axis) versus Fl-2 (Y-axis). Two gates, P2 at higher intensity (103 and above) and P3 at lower intensity (102-103) on X-axis (Fl-1) was applied for analysis of positive cells. All the data were analyzed using DIVA 6.1.3 software.

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art. In case of a conflict between the specification and any of the incorporated references, the specification (including any amendments thereof, which may be based on an incorporated reference), shall control. Standard art-accepted meanings of terms are used herein unless indicated otherwise. Standard abbreviations for various terms are used herein.

Chen Y, Pullambhatla M, Banerjee S, Byun Y, Stathis M, Rojas C, Slusher B S, Mease R C, Pomper M G. Synthesis and biological evaluation of low molecular weight fluorescent imaging agents for the prostate-specific membrane antigen. Bioconjug Chem. 23: 2377-85 (2012);

Maresca K P, Hillier S M, Femia F J, Keith D, Barone C, Joyal J L, Zimmerman C N, Kozikowski A P, Barrett J A, Eckelman W C, Babic J W. A Series of Halogenated Heterodimeric Inhibitors of Prostate Specific Membrane Antigen (PSMA) as Radiolabeled Probes for Targeting Prostate Cancer J. Med. Chem. 52: 347-357 (2009);

Chen Y, Dhara S, Banerjee S, Byun Y, Pullambhatla M, Mease R C, Pomper M G. A low molecular weight PSMA-based fluorescent imaging agent for cancer. Biochem. Biophys Res. Commun. 390: 624-629 (2009);

Pomper, Martin G.; Mease, Ronnie C.; Ray, Sangeeta; Chen, Ying Psma-targeting compounds and uses thereof;

International PCT patent application publication no. WO2010/108125A2, for PSMA-TARGETING COMPOUNDS AND USES THEREOF, to Pomper et al., published Sep. 23, 2010.

Rowe, S P, Gorin M S, Hammers H J, Javadi M S, Hawasli H, Szabo Z, Cho S Y, Pomper M G, Allaf M E. Imaging of metastatic clear cell renal cell carcinoma with PSMA-targeted $^{18}$F-DCFPyL PET/CT. Ann. Nucl. Med. 29(10) 877-882 2015.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A compound having the structure:

[chemical structure]

wherein:
  Z is tetrazole or $CO_2Q$;
  each Q is independently selected from hydrogen or a protecting group;
  FG is a fluorescent dye moiety which emits in the visible or near infrared spectrum;
  each R is independently H or $C_1$-$C_4$ alkyl;
  V is —C(O)—;
  W is —NRC(O);
  Y is —C(O);
  a is 1, 2, 3, or 4;
  m is 1, 2, 3, 4, 5, or 6;
  n is 1, 2, 3, 4, 5 or 6;
  p is 0, 1, 2, or 3, and when p is 2 or 3, each $R^1$ may be the same or different;
  $R^1$ is H, $C_1$-$C_6$ alkyl, $C_6$-$C_{12}$ aryl, or alkylaryl having 1 to 3 separate or fused rings and from 6 to about 18 ring carbon atoms;
  $R^2$ and $R^3$ are independently H, $CO_2H$, or $CO_2R^4$, where $R^4$ is a $C_1$-$C_6$ alkyl, $C_6$-$C_{12}$ aryl, or alkylaryl having 1 to 3 separate or fused rings and from 6 to about 18 ring carbon atoms, wherein when one of $R^2$ and $R^3$ is $CO_2H$ or $CO_2R^4$, the other is H.

2. A compound according to claim 1 having the structure:

[chemical structure]

3. A compound according to claim 2 having the structure:

[chemical structure]

4. A compound according to claim 1, wherein $R^3$ is $CO_2H$ and $R^2$ is H or $R^2$ is $CO_2H$ and $R^3$ is H.

5. A compound according to claim 1, wherein $R^2$ is $CO_2R^4$ and $R^3$ is H or $R^3$ is $CO_2R^4$, and $R^2$ is H.

6. A compound according to claim 1, wherein $R^2$ is H, and $R^3$ is H.

7. A compound according to claim 1, wherein $R^4$ is $C_6$-$C_{12}$ aryl, or alkylaryl having 1 to 3 separate or fused rings and from 6 to about 18 ring carbon atoms.

8. A compound according to claim 1, wherein $R^1$ is $C_6$-$C_{12}$ aryl.

9. A compound according to claim 8 wherein $R^1$ is phenyl.

10. A compound according to claim 1, wherein FG is a fluorescent dye moiety which emits in the near infrared spectrum.

11. A compound according to claim 1, wherein FG is selected from the group consisting of a polymethine dye, a coumarin dye, a xanthene dye, and a boron-dipyrromethene dye.

12. A compound according to claim 1, wherein FG has a structure selected from the group consisting of:

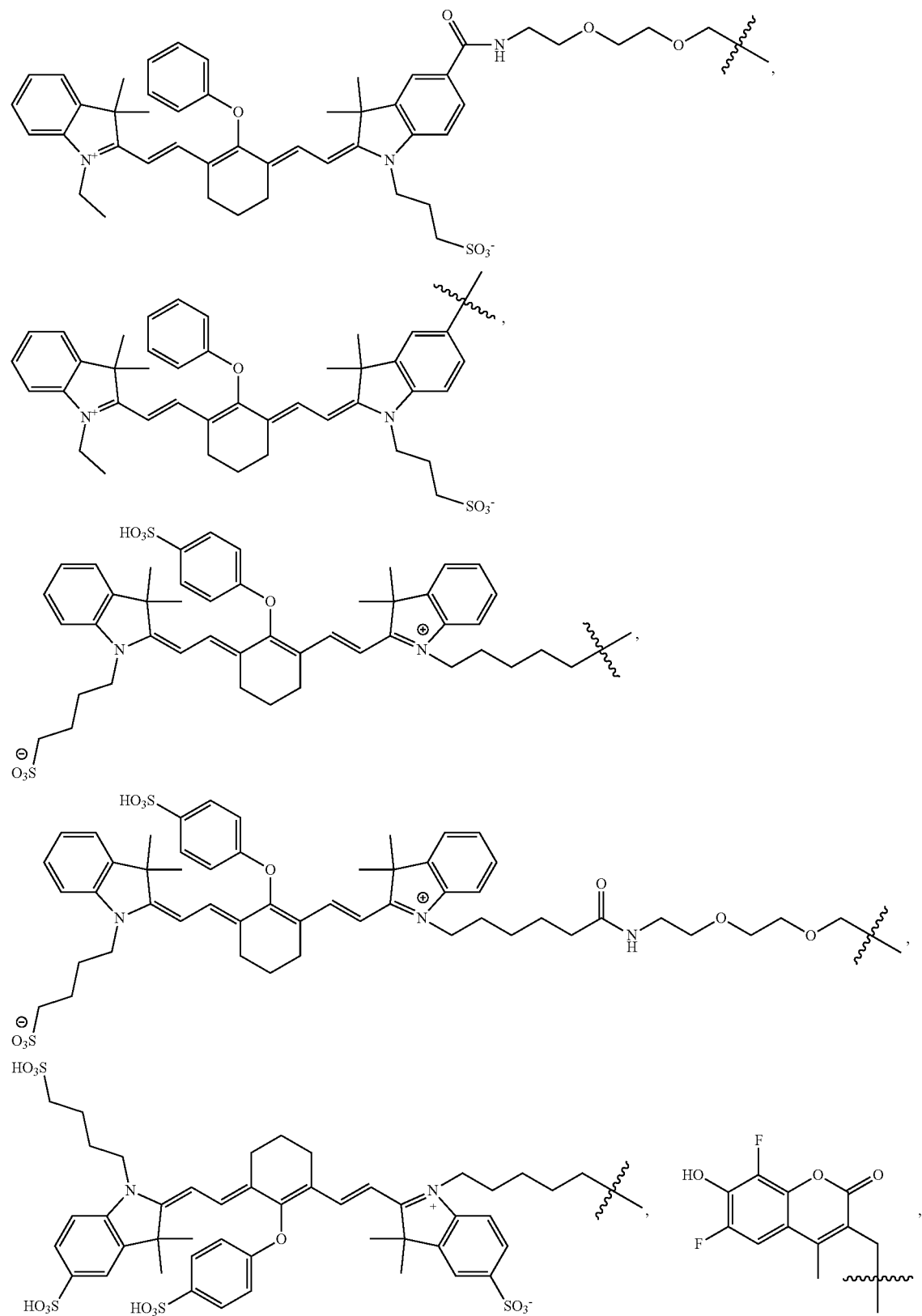

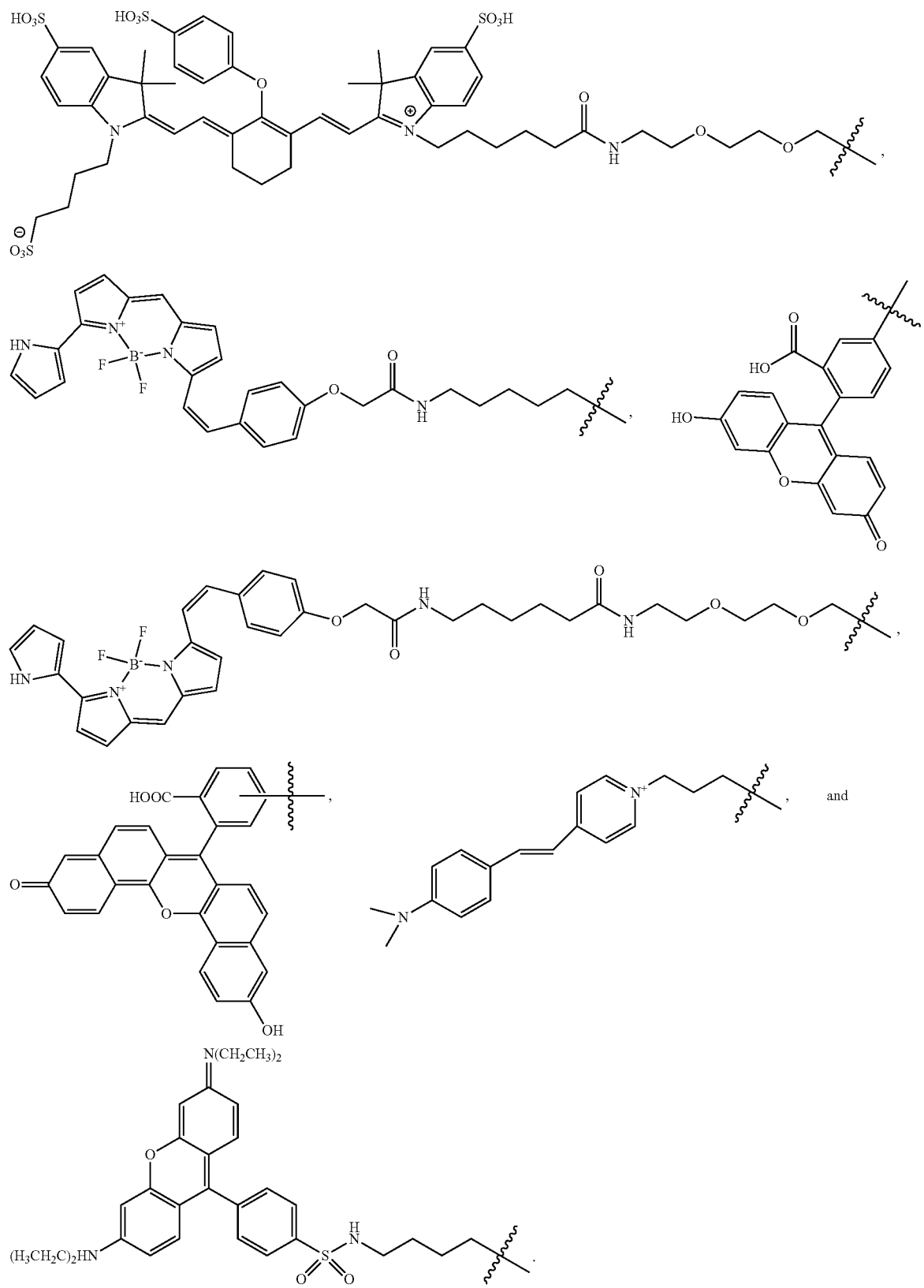

13. A compound according to claim 1 selected from the group consisting of:
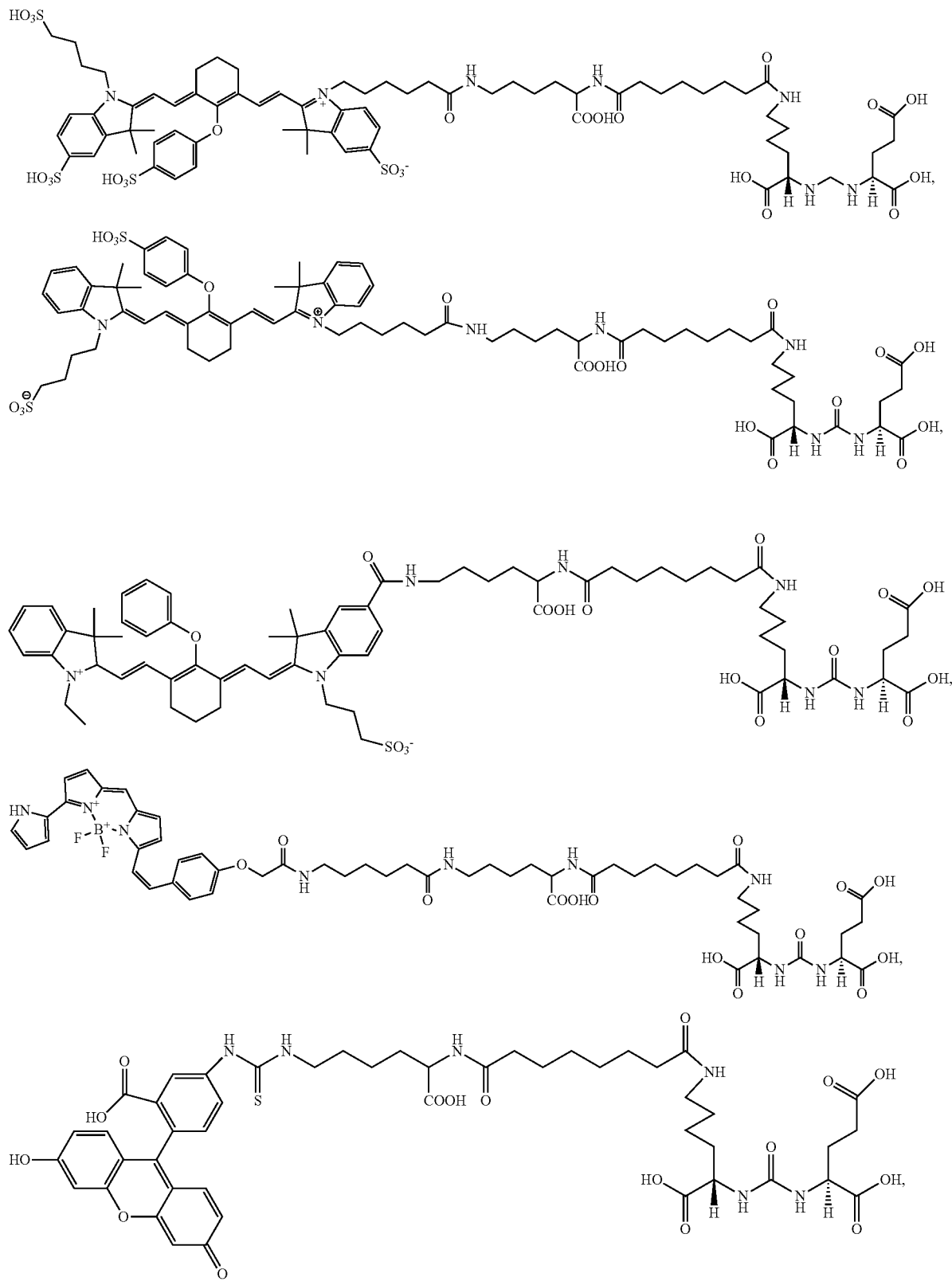

-continued

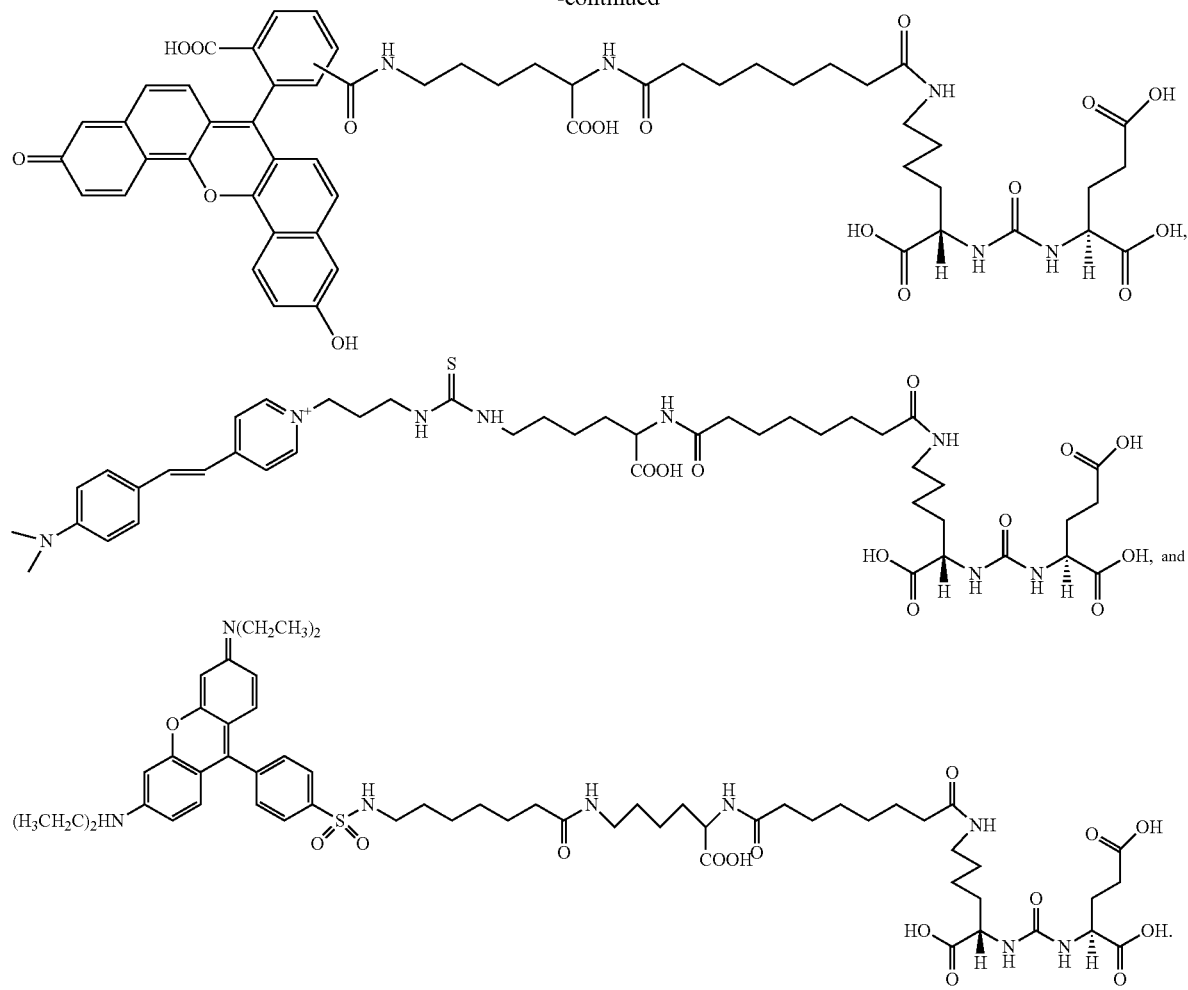

14. A method of imaging one or more cells, organs or tissues by exposing the cell to or administering to an organism an effective amount of a compound according to claim 1, where the compound includes a fluorescent dye moiety suitable for imaging.

15. A method for sorting cells by exposing the cells to a compound according to claim 1, where the compound includes a fluorescent dye moiety, followed by separating cells which bind the compound from cells which do not bind the compound.

16. A method for intraoperative tumor mapping comprising administering an effective amount of a compound according to claim 1, where the compound includes a fluorescent dye moiety.

17. A kit comprising a compound according to claim 1.

18. The compound according to claim 1, wherein the protecting group is selected from the group consisting of benzyl, p-methoxybenzyl, tertiary butyl, methoxymethyl, methoxyethoxymethyl, methylthiomethyl, tetrahydropyranyl, tetrahydrofuranyl, benzyloxymethyl, trimethylsilyl, triethylsilyl, t-butyldimethylsilyl, and triphenylmethyl.

19. The compound according to claim 11, wherein the polymethine dye is selected from the group consisting of a carbocyanine dye, a indocarbocyanine dye, an oxacarbocyanine dye, a thiacarbocyanine dye, and a merocyanine dye.

20. The compound according to claim 19, wherein the polymethine dye comprises an indocarbocyanine.

21. The compound according to claim 11, wherein the xanthene dye is selected from the group consisting of a fluorescein dye and a coumarin dye.

* * * * *